(12) United States Patent
Ajikumar et al.

(10) Patent No.: US 10,519,470 B2
(45) Date of Patent: *Dec. 31, 2019

(54) MICROBIAL ENGINEERING FOR THE PRODUCTION OF CHEMICAL AND PHARMACEUTICAL PRODUCTS FROM THE ISOPRENOID PATHWAY

(71) Applicants: Massachusetts Institute of Technology, Cambridge, MA (US); National University of Singapore, Singapore (SG)

(72) Inventors: Parayil K. Ajikumar, Cambridge, MA (US); Gregory Stephanopoulos, Winchester, MA (US); Heng Phon Too, Singapore (SG)

(73) Assignees: Massachusetts Institute of Technology, Cambridge, MA (US); National University of Singapore, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/924,700

(22) Filed: Mar. 19, 2018

(65) Prior Publication Data

US 2018/0282766 A1    Oct. 4, 2018

Related U.S. Application Data

(63) Continuation of application No. 15/208,099, filed on Jul. 12, 2016, now Pat. No. 9,957,527, which is a continuation of application No. 14/552,676, filed on Nov. 25, 2014, now Pat. No. 9,404,130, which is a continuation of application No. 13/249,388, filed on Sep. 30, 2011, now Pat. No. 8,927,241, which is a continuation-in-part of application No. 12/943,477, filed on Nov. 10, 2010, now Pat. No. 8,512,988.

(60) Provisional application No. 61/388,543, filed on Sep. 30, 2010, provisional application No. 61/280,877, filed on Nov. 10, 2009.

(51) Int. Cl.

| C12P 5/00 | (2006.01) |
|---|---|
| C12Q 1/689 | (2018.01) |
| C12P 9/00 | (2006.01) |
| C12N 15/70 | (2006.01) |
| C12P 19/56 | (2006.01) |
| C12P 7/42 | (2006.01) |
| C12P 23/00 | (2006.01) |
| C12P 17/02 | (2006.01) |
| C12P 15/00 | (2006.01) |

(52) U.S. Cl.
CPC ............ *C12P 5/007* (2013.01); *C12N 15/70* (2013.01); *C12P 7/42* (2013.01); *C12P 9/00* (2013.01); *C12P 15/00* (2013.01); *C12P 17/02* (2013.01); *C12P 19/56* (2013.01); *C12P 23/00* (2013.01); *C12Q 1/689* (2013.01); *C12Q 2600/158* (2013.01); *H05K 999/99* (2013.01)

(58) Field of Classification Search
CPC .......... C12P 15/00; C12P 17/02; C12P 23/00; C12P 5/007; C12P 7/42; C12P 9/00; C12P 19/56; H05K 999/99; C12N 15/70; C12Q 1/689; C12Q 2600/158
See application file for complete search history.

(56) References Cited

U.S. PATENT DOCUMENTS

| 7,659,097 B2* | 2/2010 | Renninger ............... C12P 5/007 435/157 |
|---|---|---|
| 8,257,957 B2 | 9/2012 | Keasling et al. |
| 8,512,988 B2* | 8/2013 | Ajikumar ................ C12P 15/00 435/166 |
| 8,927,241 B2 | 1/2015 | Ajikumar et al. |
| 9,284,570 B2 | 3/2016 | Stephanopoulos et al. |
| 9,359,624 B2* | 6/2016 | Ajikumar ................ C12P 15/00 |
| 9,404,130 B2 | 8/2016 | Ajikumar et al. |
| 9,796,980 B2 | 10/2017 | Ajikumar et al. |
| 9,957,527 B2 | 5/2018 | Ajikumar et al. |
| 2004/0072323 A1 | 4/2004 | Matsuda et al. |
| 2007/0026484 A1 | 2/2007 | Kinney et al. |
| 2008/0274523 A1 | 11/2008 | Renninger et al. |
| 2010/0297722 A1 | 11/2010 | Anterola et al. |
| 2012/0107893 A1 | 5/2012 | Ajikumar et al. |
| 2012/0164678 A1 | 6/2012 | Stephanopoulos et al. |
| 2013/0171328 A1 | 7/2013 | Kishore et al. |
| 2014/0024089 A1 | 1/2014 | Ajikumar et al. |
| 2015/0152446 A1 | 6/2015 | Ajikumar et al. |
| 2017/0002366 A1 | 1/2017 | Ajikumar et al. |
| 2017/0002382 A1 | 1/2017 | Ajikumar et al. |
| 2018/0080035 A1 | 3/2018 | Ajikumar et al. |
| 2019/0017077 A1 | 1/2019 | Ajikumar et al. |

FOREIGN PATENT DOCUMENTS

| WO | 1997/038571 A1 | 10/1997 |
|---|---|---|
| WO | 2008/128159 A1 | 10/2008 |

OTHER PUBLICATIONS

Patchoulol-Wikipedia: 3 (three) pages downloaded from https://en.wikipedia.org/wiki/Patchoulol on 01/04/209. (Year: 2019).*

(Continued)

*Primary Examiner* — Ganapathirama Raghu

(74) *Attorney, Agent, or Firm* — Wolf, Greenfield & Sacks, P.C.

(57) ABSTRACT

The invention relates to the production of one or more terpenoids through microbial engineering, and relates to the manufacture of products comprising terpenoids.

22 Claims, 24 Drawing Sheets

Specification includes a Sequence Listing.

(56) References Cited

OTHER PUBLICATIONS

[No Author Listed] Steviol. Wikipedia. Last accessed at https://en.wikipedia.org/wiki/Steviol on Dec. 1, 2015.
[No Author Listed] Steviol glycoside. Wikipedia. Last accessed at https://en.wikipedia.org/wiki/Steviol_glycoside on Dec. 1, 2015.
[No Author Listed] Valencene. Wikipedia. Last accessed at https://en.wikipedia.org/wiki/valencene on Jul. 12, 2017.
Ajikumar et al., Isoprenoid pathway optimization for Taxol precursor overproduction in Escherichia coli. Science. Oct. 1, 2010;330(6000):70-4.
Ajikumar et al., Terpenoids: opportunities for biosynthesis of natural product drugs using engineered microorganisms. Mol Pharm. Mar.-Apr. 2008;5(2):167-90. Epub Mar. 21, 2008.
Alper et al., Construction of lycopene-overproducing E. coli strains by combining systematic and combinatorial gene knockout targets. Nat Biotechnol. May 2005;23(5):612-6. Epub Apr. 10, 2005.
Balderas-Hernández et al., Metabolic engineering for improving anthranilate synthesis from glucose in Escherichia coli. Microb Cell Fact. Apr. 2, 2009 ;8:19. doi: 10.1186/1475-2859-819.
Behr et al., Myrcene as a natural base chemical in sustainable chemistry: a critical review. ChemSusChem. 2009;2(12):1072-95. doi: 10.1002/cssc.200900186.
Bohlmann et al., Monoterpene synthases from grand fir (Abies grandis). cDNA isolation, characterization, and functional expression of myrcene synthase, (-)-(4S)-limonene synthase, and (-)-(1S,5S)-pinene synthase. J Biol Chem. Aug. 29, 1997;272(35):21784-92.
Brandle et al., Steviol glycoside biosynthesis. Phytochemistry. Jul. 2007;68(14):1855-63. Epub Mar. 29, 2007.
Brosius et al., Spacing of the -10 and -35 regions in the tac promoter. Effect on its in vivo activity. J Biol Chem. Mar. 25, 1985;260(6):3539-41.
Broun et al., Catalytic plasticity of fatty acid modification enzymes underlying chemical diversity of plant lipids. Science. Nov. 13, 1998;282(5392):1315-7.
Brunner et al., Promoter recognition and promoter strength in the Escherichia coli system. Embo J. Oct. 1987;6(10):3139-44.
Burke et al., Geranyl diphosphate synthase from Abies grandis: cDNA isolation, functional expression, and characterization. Arch Biochem Biophys. Sep. 1, 2002;405(1):130-6.
Carakostas et al., Overview: the history, technical function and safety of rebaudioside A, a naturally occurring steviol glycoside, for use in food and beverages. Food Chem Toxicol. Jul. 2008;46 Suppl 7:S1-S10. doi: 10.1016/j.fct.2008.05.003. Epub May 16, 2008.
Chang et al., Engineering Escherichia coli for production of functionalized terpenoids using plant P450s. Nat Chem Biol. May 2007;3(5):274-7. Epub Apr. 15, 2007.
Chang et al., Gene expression profiling of Escherichia coli growth transitions: an expanded stringent response model. Mol Microbiol. Jul. 2002;45(2):289-306.
Chang et al., Production of isoprenoid pharmaceuticals by engineered microbes. Nat Chem Biol. Dec. 2006;2(12):674-81.
Chau et al., Taxol biosynthesis: Molecular cloning and characterization of a cytochrome P450 taxoid 7 beta-hydroxylase. Chem Biol. May 2004;11(5):663-72.
Chica et al., Semi-rational approaches to engineering enzyme activity: combining the benefits of directed evolution and rational design. Curr Opin Biotechnol. Aug. 2005;16(4):378-84.
Croteau et al., Natural Products (Secondary Metabolites). Biochem Mol Biol Plants. 2000. Chapter 24. 1250-318.
Croteau et al., Taxol biosynthesis and molecular genetics. Phytochem Rev. Feb. 2006;5(1):75-97.
Dagnino et al., Terpenoid indole alkaloid biosynthesis and enzyme activities in 2 cell lines of tabernaemontana divaricata. Phytochemistry. 1995;39(2):341-349.
Das et al., An update on microbial carotenoid production: application of recent metabolic engineering tools. Appl Microbiol Biotechnol. Dec. 2007;77(3):505-12. Epub Oct. 3, 2007.
Datsenko et al., One-step inactivation of chromosomal genes in Escherichia coli K-12 using PCR products. Proc Natl Acad Sci U S A. Jun. 6, 2000;97(12):6640-5.
Dejong et al., Genetic engineering of taxol biosynthetic genes in Saccharomyces cerevisiae. Biotechnol Bioeng. Feb. 2006 5;93(2):212-24.
Devos et al., Practical limits of function prediction. Proteins. Oct. 1, 2000;41(1):98-107.
Engels et al., Metabolic engineering of taxadiene biosynthesis in yeast as a first step towards Taxol (Paclitaxel) production. Metab Eng. May-Jul. 2008;10(3-4):201-6. doi: 10.1016/j.ymben.2008.03.001. Epub Mar. 26, 2008.
Farmer et al., Improving lycopene production in Escherichia coli by engineering metabolic control. Nat Biotechnol. May 2000;18(5):533-7.
Farmer et al., Precursor balancing for metabolic engineering of lycopene production in Escherichia coli. Biotechnol Prog. Jan.-Feb. 2001;17(1):57-61.
Frense, Taxanes: perspectives for biotechnological production. Appl Microbiol Biotechnol. Jan. 2007;73(6):1233-40. Epub Nov. 24, 2006.
Genbank Submission; NCBI, Accession No. AAB87091; Richman et al.; Mar. 22, 2000.
Genbank Submission; NCBI, Accession No. AAM53963; Ma et al.; Jun. 17, 2002.
Genbank Submission; NCBI, Accession No. AAN40684; Ma et al.; Oct. 14, 2002.
Genbank Submission; NCBI, Accession No. AAR06917; Richman et al.; Dec. 28, 2004.
Genbank Submission; NCBI, Accession No. AAR06920; Richman et al.; Dec. 28, 2004.
Genbank Submission; NCBI, Accession No. AAR06921; Richman et al.; Dec. 28, 2004.
Genbank Submission; NCBI, Accession No. ABA42921; Humphrey et al.; Jun. 21, 2006.
Genbank Submission; NCBI, Accession No. ABB88839; Kumar et al.; May 28, 2008.
Genbank Submission; NCBI, Accession No. ABD92926; Kumar et al.; Oct. 10, 2007.
Genbank Submission; NCBI, Accession No. ACD93722; Reeja et al.; Jun. 10, 2008.
Genbank Submission; NCBI, Accession No. ACE87855; Joseph et al.; Jun. 24, 2008.
Genbank Submission; NCBI, Accession No. AF081514; Hefner et al.; May 1, 2001.
Genbank Submission; NCBI, Accession No. AF097311_1; Richman et al.; Mar. 22, 2000.
Genbank Submission; NCBI, Accession No. AY571340; Jennewein et al.; Jan. 20, 2010.
Genbank Submission; NIH/NCBI, Accession No. AAN01134; Burke et al.; Aug. 29, 2002.
Genbank Submission; NIH/NCBI, Accession No. AF271259; Hosoi et al.; Feb. 3, 2005.
Genbank Submission; NIH/NCBI, Accession No. AY195608; Dudareva et al.; May 3, 2003.
Genbank Submission; NIH/NCBI, Accession No. U87908; Bohlmann et al.; Sep. 24, 1997.
Geuns, Steviol glycosides as food additive. Eustas. Sep. 26, 2007;1-20.
Geuns, Stevioside. Phytochemistry. Nov. 2003;64(5):913-21.
Gibson et al., Creation of a bacterial cell controlled by a chemically synthesized genome. Science. Jul. 2, 2010;329(5987):52-6. doi: 10.1126/science.1190719. Epub May 20, 2010.
Hefner et al., Cloning and functional expression of a cDNA encoding geranylgeranyl diphosphate synthase from Taxus canadensis and assessment of the role of this prenyltransferase in cells induced for taxol production. Arch Biochem Biophys. Dec. 1, 1998;360(1):62-74.
Heinig et al., Taxol: A complex diterpenoid natural product with an evolutionarily obscure origin. African J Biotechnol. 2009;8:1370-85.

(56) References Cited

OTHER PUBLICATIONS

Hoffmann et al., Metabolic adaptation of *Escherichia coli* during temperature-induced recombinant protein production: 1. Readjustment of metabolic enzyme synthesis. Biotechnol Bioeng. Nov. 5, 2002;80(3):313-9.

Hoffmann et al., Stress induced by recombinant protein production in *Escherichia coli*. Adv Biochem Eng Biotechnol. 2004;89:73-92.

Holton et al., First total synthesis of taxol. 2. Completion of the C and D rings. J. Am. Chem. Soc. Feb. 1994;116 (4):1599-1600.

Huang et al., Engineering *Escherichia coli* for the synthesis of taxadiene, a key intermediate in the biosynthesis of taxol. Bioorg Med Chem. Sep. 2001;9(9):2237-42.

Hughes et al., Metabolic engineering of the indole pathway in Catharanthus roseus hairy roots and increased accumulation of tryptamine and serpentine. Metab Eng. Oct. 2004;6(4):268-76.

Humphrey et al., Spatial organisation of four enzymes from Stevia rebaudiana that are involved in steviol glycoside synthesis. Plant Mol Biol. May 2006;61(1-2):47-62.

Jennewein et al., Coexpression in yeast of Taxus cytochrome P450 reductase with cytochrome P450 oxygenases involved in Taxol biosynthesis. Biotechnol Bioeng. Mar. 5, 2005;89(5):588-98.

Jennewein et al., Cytochrome p450 taxadiene 5alpha-hydroxylase, a mechanistically unusual monooxygenase catalyzing the first oxygenation step of taxol biosynthesis. Chem Biol. Mar. 2004;11(3):379-87.

Jennewein et al., Random sequencing of an induced Taxus cell cDNA library for identification of clones involved in Taxol biosynthesis. Proc Natl Acad Sci U S A. Jun. 15, 2004;101(24):9149-54. Epub Jun. 3, 2004.

Jennewein et al., Taxol: biosynthesis, molecular genetics, and biotechnological applications. Appl Microbiol Biotechnol. Oct. 2001;57(1-2):13-9.

Jin et al., Multi-dimensional gene target search for improving lycopene biosynthesis in *Escherichia coli*. Metab Eng. Jul. 2007;9(4):337-47. Epub Apr. 12, 2007.

Jones et al., Low-copy plasmids can perform as well as or better than high-copy plasmids for metabolic engineering of bacteria. Metab Eng. Oct. 2000;2(4):328-38.

Kaspera et al., Cytochrome P450 oxygenases of Taxol biosynthesis. Phytochem Rev. Jun. 2006; 5(2-3): 433-444. doi: 10.1007/s11101-006-9006-4.

Khosla et al., Metabolic engineering for drug discovery and development. Nat Rev Drug Discov. Dec. 2003;2(12):1019-25.

Kim et al., Metabolic engineering of the nonmevalonate isopentenyl diphosphate synthesis pathway in *Escherichia coli* enhances lycopene production. Biotechnol Bioeng. Feb. 20, 2001;72(4):408-15.

Kimchi-Sarfaty et al., a "silent" polymorphism in the MDR1 gene changes substrate specificity. Science. Jan. 26, 2007;315(5811):525-8. Epub Dec. 21, 2006. Erratum in: Science. Oct. 7, 2011;334(6052):39. Science. Nov. 30, 2007;318(5855):1382-3.

Kingston, The shape of things to come: structural and synthetic studies of taxol and related compounds. Phytochemistry. Jul. 2007;68(14):1844-54. Epub Dec. 20, 2006.

Kirby et al., Biosynthesis of plant isoprenoids: perspectives for microbial engineering. Annu Rev Plant Biol. 2009;60:335-55.

Kisselev, Polypeptide release factors in prokaryotes and eukaryotes: same function, different structure. Structure. Jan. 2002;10(1):8-9.

Klein-Marcuschamer et al., Engineering microbial cell factories for biosynthesis of isoprenoid molecules: beyond lycopene. Trends Biotechnol. Sep. 2007;25(9):417-24. Epub Aug. 2, 2007.

Kodumal et al., Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.

Leonard et al., Combining metabolic and protein engineering of a terpenoid biosynthetic pathway for overproduction and selectivity control. Proc Natl Acad Sci U S A. Aug. 3, 2010;107(31):13654-9. Epub Jul. 19, 2010.

Leonard et al., Engineering of artificial plant cytochrome P450 enzymes for synthesis of isoflavones by *Escherichia coli*. Appl Environ Microbiol. Nov. 2007;73(22):7246-51. Epub Sep. 28, 2007.

Liao, Molecular biology of the biosynthetic pathways of taxol precursors and metabolic engineering of anti-tumor terpenoid indole alkaloids. Dissertation. 1-156. Fudan University. May 2004.

Martin et al., Engineering a mevalonate pathway in *Escherichia coli* for production of terpenoids. Nat Biotechnol. Jul. 2003;21(7):796-802. Epub Jun. 1, 2003.

Mishra et al., Stevia Rebaudiana—A Magical Sweetener. Global J Biotech & Biochem. 2010 5(1):62-74.

Moreno et al., Effects of elicitation on different metabolic pathways in catharanthus roseus (L)g.don cell suspension cultures. Enzyme Microb Technol. 1996;18:99-107.

Morrone et al., Increasing diterpene yield with a modular metabolic engineering system in *E. coli*: comparison of MEV and MEP isoprenoid precursor pathway engineering. Appl Microbiol Biotechnol. Feb. 2010;85(6):1893-906. doi: 10.1007/s00253-009-2219-x. Epub Sep. 24, 2009.

Nackley et al., Human catechol-O-methyltransferase haplotypes modulate protein expression by altering mRNA secondary structure. Science. Dec. 22, 2006;314(5807):1930-3.

Nelson, Cytochrome P450 and the individuality of species. Arch Biochem Biophys. Sep. 1, 1999;369(1):1-10.

Nicolaou, et al. Total synthesis of taxol. Nature. Feb. 17, 1994;367(6464):630-4.

Nishizaki et al., Metabolic Engineering of Carotenoid Biosynthesis in *Escherichia coli* by Ordered Gene Assembly in Bacillus subtilis. Appl Environ Microbiol. Feb. 2007; 73(4): 1355-1361.

Richman et al., Diterpene synthesis in Stevia rebaudiana: recruitment and up-regulation of key enzymes from the gibberellin biosynthetic pathway. Plant J. Aug. 1999;19(4):411-21.

Richman et al., Functional genomics uncovers three glucosyltransferases involved in the synthesis of the major sweet glucosides of Stevia rebaudiana. Plant J. Jan. 2005;41(1):56-67.

Roberts, Production and engineering of terpenoids in plant cell culture. Nat Chem Biol. Jul. 2007;3(7):387-95.

Rontein et al., CYP725A4 from yew catalyzes complex structural rearrangement of taxa-4(5),11(12)-diene into the cyclic ether 5(12)-oxa-3(11)-cyclotaxane. J Biol Chem. Mar. 7, 2008;283(10):6067-75. doi: 10.1074/jbc.M708950200. Epub Dec. 31, 2007.

Rost et al., The PredictProtein server. Nucleic Acids Res. Jul. 1, 2004;32(Web Server issue):W321-6.

Sandmann, Combinatorial biosynthesis of carotenoids in a heterologous host: a powerful approach for the biosynthesis of novel structures. Chembiochem. Jul. 2, 2002;3(7):629-35.

Sauna et al., Silent polymorphisms speak: how they affect pharmacogenomics and the treatment of cancer. Cancer Res. Oct. 15, 2007;67(20):9609-12.

Schuler et al., Functional genomics of P450s. Annu Rev Plant Biol. 2003;54:629-67.

Seffernick et al., Melamine deaminase and atrazine chlorohydrolase: 98 percent identical but functionally different. J Bacteriol. Apr. 2001;183(8):2405-10.

Sen et al., Developments in directed evolution for improving enzyme functions. Appl Biochem Biotechnol. Dec. 2007;143(3):212-23.

Shalel-Levanon et al., Effect of ArcA and FNR on the expression of genes related to the oxygen regulation and the glycolysis pathway in *Escherichia coli* under microaerobic growth conditions. Biotechnol Bioeng. Oct. 20, 2005;92(2):147-59.

Sharma et al., Chemistry and in vivo profile of ent-kaurene glycosides of Stevia rebaudiana Bertoni—An overview. Natural Product Radiance. 2009;8(2):181-189.

Shigemori et al., Biological activity and chemistry of taxoids from the Japanese yew, Taxus cuspidata. J Nat Prod. Feb. 2004;67(2):245-56.

Singh et al., Stevia: The herbal sugar of 21st century. Sugar Tech. Mar. 2005;7(1):17-24.

Sørensen et al., Advanced genetic strategies for recombinant protein expression in *Escherichia coli*. J Biotechnol. Jan. 26, 2005;115(2):113-28.

(56) References Cited

OTHER PUBLICATIONS

Stephanopoulos, Bioreaction network analysis: A central component of microbe and metabolic engineering. Annual AIChE Meeting—2009. Session honoring Professor James Wei. Nashville, TN. Nov. 9, 2009.

Stephanopoulos, Engineering microbes for biofuel production. TMFB Tailor Made Fuels from Biomass, 2$^{nd}$ International Workshop. RW Technical University. Jun. 24-25, 2009.

Stewart, A chemist's perspective on the use of genetically engineered microbes as reagents for organic synthesis. Biotechnol Genet Eng Rev. 1997;14:67-143.

Trapp et al., Genomic organization of plant terpene synthases and molecular evolutionary implications. Genetics. Jun. 2001;158(2):811 32.

Tyo et al., Expanding the metabolic engineering toolbox: more options to engineer cells. Trends Biotechnol. Mar. 2007;25(3):132-7. Epub Jan. 24, 2007.

Tyo et al., Stabilized gene duplication enables long-term selection-free heterologous pathway expression. Nat Biotechnol. Aug. 2009;27(8):760-5. doi: 10.1038/nbt.1555. Epub Jul. 26, 2009.

Ulbricht et al., An evidence-based systematic review of stevia by the Natural Standard Research Collaboration. Cardiovasc Hematol Agents Med Chem. Apr. 2010;8(2):113-27.

Veau et al., Cloning and expression of cDNAs encoding two enzymes of the MEP pathway in *Catharanthus roseus*. Biochim Biophys Acta. Dec. 15, 2000;1517(1):159-63.

Verpoorte et al., Biotechnology for the production of plant secondary metabolites. Phytochem Rev. 2002;1(1):13-25.

Verpoorte et al., Plant cell biotechnology for the production of secondary metabolites. Pure & Appl. Chem. 1994:66:2307-2310.

Walji et al., Strategies to Bypass the Taxol Problem: Enantioselective Cascade Catalysis, A New Approach for the Efficient Construction of Molecular Complexity. Synlett. 2007;10:1477-1489.

Walker et al., Taxol biosynthetic genes. Phytochemistry. Sep. 2001;58(1):1-7.

Wang et al., Programming cells by multiplex genome engineering and accelerated evolution. Nature. Aug. 2009;460:894-898.

Wani et al., Plant antitumor agents. VI. The isolation and structure of taxol, a novel antileukemic and antitumor agent from Taxus brevifolia. J Am Chem Soc. May 5, 1971;93(9):2325-7.

Whisstock et al., Prediction of protein function from protein sequence and structure. Q Rev Biophys. Aug. 2003;36(3):307-40.

Whitmer et al., Influence of Precursor Availability on Alkaloid Accumulation by Transgenic Cell Line of *Catharanthus roseus*. Plant Physiol. Feb. 1, 1998;116(2):853-7.

Wildung et al., A cDNA clone for taxadiene synthase, the diterpene cyclase that catalyzes the committed step of taxol biosynthesis. J Biol Chem. Apr. 19, 1996;271(16):9201-4.

Williams et al., Heterologous expression and characterization of a "Pseudomature" form of taxadiene synthase involved in paclitaxel (Taxol) biosynthesis and evaluation of a potential intermediate and inhibitors of the multistep diterpene cyclization reaction. Arch Biochem Biophys. Jul. 1, 2000;379(1):137-46.

Wishart et al., A single mutation converts a novel phosphotyrosine binding domain into a dual-specificity phosphatase. J Biol Chem. Nov. 10, 1995;270(45):26782-5.

Witkowski et al., Conversion of a beta-ketoacyl synthase to a malonyl decarboxylase by replacement of the active-site cysteine with glutamine. Biochemistry. Sep. 7, 1999;38(36):11643-50.

Xu et al., Strain improvement and optimization of the media of taxol-producing fungus Fusarium maire. Biochem Engineer J. Aug. 2006;31(1):67-73.

Yang et al., Metabolic engineering of *Escherichia coli* for the biosynthesis of alpha-pinene. Biotechnol Biofuels. Apr. 30, 2013;6(1):60. doi: 10.1186/1754-6834-6-60.

Yuan et al., Chromosomal promoter replacement of the isoprenoid pathway for enhancing carotenoid production in *E. coli*. Metab Eng. Jan. 2006;8(1):79-90. Epub Oct. 28, 2005.

\* cited by examiner

1. Ep20TrcGT
2. ECh1TrcMEPp20GT
3. Ep5TrcMEPp20TrcGT
4. Ep10TrcMEPp20TrcGT
5. Ep20TrcTG
6. Ep20T5GT
7. Ep20T5GTTrcT
8. ECh1TrcMEPp20TrcTG
9. ECh1TrcMEPp20T5GT
10. ECh1TrcMEPp20T5GTTrcT
11. Ep5TrcMEPp20TrcTG
12. Ep5TrcMEPp20T5GT
13. Ep5TrcMEPp20T5GTTrct
14. Ep10TrcMEPp20TrcTG
15. Ep10TrcMEPp20T5GT
16. Ep10TrcMEPp20T5GTTrcT
17. EDE3p10TrcMEPp5T7TG
18. EDE3p20TrcMEPp5T7TG
19. EDE3p20T5MEPp5T7TG
20. EDE3p20T7MEPp5T7TG
21. EDE3p5TrcMEPp10T7TG
22. EDE3p20TrcMEPp10T7TG
23. EDE3p20T5MEPp10T7TG
24. EDE3p20T7MEPp10T7TG
25. EDE3p5T7TG
26. EDE3Ch1TrcMEPp5T7TG
27. EDE3Ch1T5MEPp5T7TG
28. EDE3Ch1T7MEPp5T7TG
29. EDE3p10T7TG
30. EDE3Ch1TrcMEPp10T7TG
31. EDE3Ch1T5MEPp10T7TG
32. EDE3Ch1T7MEPp10T7TG

Fig. 2E

A ▨ Predicted 42AA TM Region in T5αOH
B ▨ Predicted 74AA TM Region in TCPR
◐ One Amino Acid Substituted Bovine 17α Hydroxylase N-terminal 8 Residue Peptide MALLLAVF Fused With 8, 24 and 42AA Truncated from the TM Region in T5αOH
∿ GSTGS Peptide Linker Between TM Engineered T5αOH and 74AA Truncated TCPR

MICROBIAL ENGINEERING FOR THE PRODUCTION OF CHEMICAL AND PHARMACEUTICAL PRODUCTS FROM THE ISOPRENOID PATHWAY

RELATED APPLICATIONS

This application is a continuation application of U.S. application Ser. No. 15/208,099, filed on Jul. 12, 2016, and issued as U.S. Pat. No. 9,957,527, which is a continuation of U.S. application Ser. No. 14/552,676, filed on Nov. 25, 2014 and issued as U.S. Pat. No. 9,404,130, which is a continuation application of U.S. application Ser. No. 13/249,388, filed on Sep. 30, 2011 and issued as U.S. Pat. No. 8,927,241, which is a continuation-in-part of U.S. application Ser. No. 12/943,477, filed on Nov. 10, 2010, and issued as U.S. Pat. No. 8,512,988, which claims the benefit under 35 U.S.C. § 119(e) of U.S. Provisional Application Ser. No. 61/280,877, filed on Nov. 10, 2009 and U.S. Provisional Application Ser. No. 61/388,543, filed on Sep. 30, 2010, the entire disclosures of which are incorporated by reference herein in their entireties.

GOVERNMENT INTEREST

This invention was made with Government support under Grant No. R01-GM085323 awarded by the National Institutes of Health. The Government has certain rights in the invention.

FIELD OF THE INVENTION

The invention relates to the production of one or more terpenoids through microbial engineering.

BACKGROUND OF THE INVENTION

Terpenoids are a class of compounds with diverse uses, including in fragrances, cosmetics, food products, pharmaceuticals, and other products. Thus, methods for their efficient and cost effective production are needed.

For example, Taxol and its structural analogs have been recognized as the most potent and commercially successful anticancer drugs introduced in the last decade.[1] Taxol was first isolated from the bark of the Pacific Yew tree,[2] and early stage production methods required sacrificing two to four fully grown trees to supply sufficient dosage for one patient.[3] Taxol's structural complexity necessitated a complex chemical synthesis route requiring 35-51 steps with highest yield of 0.4%.[4,5,6] However, a semi-synthetic route was devised whereby the biosynthetic intermediate baccatin III was first isolated from plant sources and was subsequently converted to Taxol.[7] While this approach and subsequent plant cell culture-based production efforts have decreased the need for harvesting the yew tree, production still depends on plant-based processes[8] with accompanying limitations of productivity and scalability, and constraints on the number of Taxol derivatives that can be synthesized in search for more efficacious drugs.[9,10]

Methods for the production of terpenoids and derivatives of these compounds, and methods of making products that comprise such compounds, are needed.

SUMMARY OF THE INVENTION

Recent developments in metabolic engineering and synthetic biology offer new possibilities for the overproduction of complex natural products through more technically amenable microbial hosts.[11,12] Although exciting progress has been made in the elucidation of the biosynthetic mechanism of Taxol in *Taxus*,[13-16] commercially relevant Taxol-producing strains have eluded prior attempts aiming at the transfer of this complex biosynthetic machinery into a microbial host.[17,18] Yet, as with other natural products, microbial production through metabolically engineered strains, offers attractive economics and great potential for synthesizing a diverse array of new compounds with anti-cancer and other pharmaceutical activity.[19,20]

The metabolic pathway for Taxol and its analogs consists of an upstream isoprenoid pathway that is native to *E. coli*, and a heterologous downstream terpenoid pathway (FIG. 6). The upstream mevalonic acid (MVA) or methylerythritol phosphate (MEP) pathways can produce the two common building blocks, isopentenyl pyrophosphate (IPP) and dimethylallyl pyrophosphate (DMAPP), from which Taxol and other isoprenoid compounds are formed.[12] Recent studies have highlighted the engineering of the above upstream pathways to support biosynthesis of heterologous isoprenoids such as lycopene and artemisinic acid.[21-23] The downstream taxadiene pathway has been reconstructed in *E. coli*, but, to-date, titers have not exceeded 1.3 mg/L.[24]

The above rational metabolic engineering approaches focused on either the upstream (MVA or MEP) or the downstream terpenoid pathway, implicitly assuming that modifications are additive, i.e. a linear behavior.[25-27] While this approach can yield moderate increases in flux, it generally ignores non-specific effects, such as toxicity of intermediate metabolites, cellular effects of the vectors used for expression, and hidden unknown pathways that may compete with the main pathway and divert flux away from the desired target. Combinatorial approaches can avoid such problems as they offer the opportunity to adequately sample the parameter space and elucidate these complex non-linear interactions.[21,28,29,30] However, they require a high throughput screen, which is often not available for many desirable natural products.[31] Yet another class of pathway optimization methods has explored the combinatorial space of different sources of the heterologous genes comprising the pathway of interest.[32] Still dependent on a high throughput assay, these methods generally ignore the need for determining an optimal level of expression for the individual pathway genes and, as such, have proven less effective in structuring an optimal pathway.

In the present work, as an example of aspects of the invention, we focus on the optimal balancing between the upstream, IPP-forming pathway with the downstream terpenoid pathway of taxadiene synthesis. This is achieved by grouping the nine-enzyme pathway into two modules—a four-gene, upstream, native (MEP) pathway module and a two-gene, downstream, heterologous pathway to taxadiene (FIG. 1). Using this basic configuration, parameters such as the effect of plasmid copy number on cell physiology, gene order and promoter strength in an expression cassette, and chromosomal integration are evaluated with respect to their effect on taxadiene production. This modular and multivariable combinatorial approach allows us to efficiently sample the main parameters affecting pathway flux without the need for a high throughput screen. The multivariate search across multiple promoters and copy numbers for each pathway module reveals a highly non-linear taxadiene flux landscape with a global maximum exhibiting a 15,000 fold increase in taxadiene production over the control, yielding 300 mg/L production of taxadiene in small-scale fermentations. Further, we have engineered the P450 based oxidation chemistry in Taxol biosynthesis in *E. coli*, with our engineered strains improving the taxadien-5α-ol production 2400-fold over the state of the art. These improvements unlock the potential for the large scale production of thousands of valuable terpenoids by well-established microbial systems.

Aspects of the invention relate to methods involving recombinantly expressing a taxadiene synthase enzyme and a geranylgeranyl diphosphate synthase (GGPPS) enzyme in a cell that overexpresses one or more components of the non-mevalonate (MEP) pathway. In some embodiments the cell is a bacterial cell such as an *Escherichia coli* cell. In some embodiments, the bacterial cell is a Gram-positive cell such as a *Bacillus* cell. In some embodiments, the cell is a yeast cell such as a *Saccharomyces* cell or a *Yarrowia* cell. In some embodiments, the cell is an algal cell or a plant cell.

In some embodiments, the taxadiene synthase enzyme is a *Taxus* enzyme such as a *Taxus brevifolia* enzyme. In some embodiments, the GGPPS enzyme is a *Taxus* enzyme such as a *Taxus canadenis* enzyme. In some embodiments, the gene encoding for the taxadiene synthase enzyme and/or the gene encoding for the GGPPS enzyme and/or the genes encoding for the one or more components of the MEP pathway is expressed from one or more plasmids. In some embodiments, the gene encoding for the taxadiene synthase enzyme and/or the gene encoding for the GGPPS enzyme and/or the genes encoding for the one or more components of the MEP is incorporated into the genome of the cell.

In some embodiments, one or more components of the non-mevalonate (MEP) pathway are selected from the group consisting of dxs, ispC, ispD, ispE, ispF, ispG, ispH, idi, ispA and ispB. In certain embodiments, dxs, idi, ispD and ispF are overexpressed. For example, dxs, idi, ispD and ispF can be overexpressed on the operon dxs-idi-idpDF. In some embodiments, the gene encoding for the taxadiene synthase enzyme and the gene encoding for the GGPPS enzyme are expressed together on an operon.

In some embodiments, the cell further expresses a taxadiene 5α-hydroxylase (T5αOH) or a catalytically active portion thereof. In certain embodiments, the T5αOH enzyme or a catalytically active portion thereof is fused to a cytochrome P450 reductase enzyme or a catalytically active portion thereof. For example, the T5αOH enzyme can be At24T5αOH-tTCPR.

The expression of the taxadiene synthase enzyme, the GGPPS enzyme and the one or more components of the MEP pathway can be balanced to maximize production of the taxadiene. Methods associated with the invention can further encompass culturing a cell to produce taxadiene or taxadiene-5α-ol. In some embodiments, at least 10 mg $L^{-1}$ of taxadiene is produced. In certain embodiments, at least 250 mg $L^{-1}$ of taxadiene is produced. In some embodiments, at least 10 mg $L^{-1}$ of taxadiene-5α-ol is produced. In certain embodiments, at least 50 mg $L^{-1}$ of taxadiene-5α-ol is produced. In some embodiments, the percentage of taxadiene conversion to taxadiene-5α-ol and the byproduct 5(12)-Oxa-3(11)-cyclotaxane is at least 50%, at least 75% or at least 95%.

Methods associated with the invention can further comprise recovering the taxadiene or taxadiene-5α-ol from the cell culture. In some embodiments, the taxadiene or taxadiene-5α-ol is recovered from the gas phase while in other embodiments, an organic layer is added to the cell culture, and the taxadiene or taxadiene-5α-ol is recovered from the organic layer.

Aspects of the invention relate to cells that overexpress one or more components of the non-mevalonate (MEP) pathway, and that recombinantly expresses a taxadiene synthase enzyme and a geranylgeranyl diphosphate synthase (GGPPS) enzyme. In some embodiments the cell is a bacterial cell such as an *Escherichia coli* cell. In some embodiments, the bacterial cell is a Gram-positive cell such as a *Bacillus* cell. In some embodiments, the cell is a yeast cell such as a *Saccharomyces* cell or a *Yarrowia* cell. In some embodiments, the cell is an algal cell or a plant cell.

In some embodiments, the taxadiene synthase enzyme is a *Taxus* enzyme such as a *Taxus brevifolia* enzyme. In some embodiments, the GGPPS enzyme is a *Taxus* enzyme such as a *Taxus canadenis* enzyme. In some embodiments, the gene encoding for the taxadiene synthase enzyme and/or the gene encoding for the GGPPS enzyme and/or the genes encoding for the one or more components of the MEP pathway is expressed from one or more plasmids. In some embodiments, the gene encoding for the taxadiene synthase enzyme and/or the gene encoding for the GGPPS enzyme and/or the genes encoding for the one or more components of the MEP is incorporated into the genome of the cell.

In some embodiments, the one or more components of the non-mevalonate (MEP) pathway is selected from the group consisting of dxs, ispC, ispD, ispE, ispF, ispG, ispH, idi, ispA and ispB. In certain embodiments, dxs, idi, ispD and ispF are overexpressed. For example, dxs, idi, ispD and ispF can be overexpressed on the operon dxs-idi-idpDF. In some embodiments, the gene encoding for the taxadiene synthase enzyme and the gene encoding for the GGPPS enzyme are expressed together on an operon. In some embodiments, the expression of the taxadiene synthase enzyme, the GGPPS enzyme and the one or more components of the MEP pathway are balanced to maximize production of the taxadiene.

In some embodiments, the cell further expresses a taxadiene 5α-hydroxylase (T5αOH) or a catalytically active portion thereof. In certain embodiments, the T5αOH enzyme or a catalytically active portion thereof is fused to a cytochrome P450 reductase enzyme or a catalytically active portion thereof. For example, the T5αOH enzyme can be At24T5αOH-tTCPR. In some embodiments, the cell produces taxadiene and/or taxadiene-5α-ol.

Aspects of the invention relate to methods for selecting a cell that exhibits enhanced production of a terpenoid, including creating or obtaining a cell that overexpresses one or more components of the non-mevalonate (MEP) pathway, producing terpenoid from the cell, comparing the amount of terpenoid produced from the cell to the amount of terpenoid produced in a control cell, and selecting a first improved cell that produces a higher amount of terpenoid than a control cell, wherein a first improved cell that produces a higher amount of terpenoid than the control cell is a cell that exhibits enhanced production of terpenoid.

In some embodiments, the cell recombinantly expresses a terpenoid synthase enzyme and/or a geranylgeranyl diphosphate synthase (GGPPS) enzyme. Methods can further comprise altering the level of expression of one or more of the components of the non-mevalonate (MEP) pathway, the terpenoid synthase enzyme and/or the geranylgeranyl diphosphate synthase (GGPPS) enzyme in the first improved cell to produce a second improved cell, and comparing the amount of terpenoid produced from the second improved cell to the amount of terpenoid produced in the first improved cell, wherein a second improved cell that produces a higher amount of terpenoid than the first improved cell is a cell that exhibits enhanced production of terpenoid. In some embodiments, the terpenoid synthase enzyme is a taxadiene synthase enzyme. The cell can further recombinantly express any of the polypeptides associated with the invention.

Aspects of the invention relate to isolated polypeptides comprising a taxadiene 5α-hydroxylase (T5αOH) enzyme or a catalytically active portion thereof fused to a cytochrome P450 reductase enzyme or a catalytically active portion thereof. In some embodiments, the cytochrome P450 reductase enzyme is a *Taxus cytochrome* P450 reductase (TCPR). In certain embodiments, the taxadiene 5α-hydroxylase and TCPR are joined by a linker such as GSTGS (SEQ ID NO:50). In some embodiments, the taxadiene 5α-hydroxylase and/or TCPR are truncated to remove all or part of the transmembrane region. In certain embodiments, 8, 24, or 42 N-terminal amino acids of taxadiene 5α-hydroxylase are truncated. In certain embodiments, 74 amino acids of TCPR are truncated. In some embodiments, an additional peptide is fused to taxadiene 5α-hydroxylase. In certain embodiments, the additional peptide is from bovine 17α hydroxylase. In certain embodiments, the peptide is MALLLAVF (SEQ ID NO:51). In certain embodiments, the isolated polypeptide is At24T5αOH-tTCPR. Aspects of the invention also encompass nucleic acid molecules that encode for any of the polypeptides associated with the invention and cells that recombinantly express any of the polypeptides associated with the invention.

Aspects of the invention relate to methods for increasing terpenoid production in a cell that produces one or more terpenoids. The methods include controlling the accumulation of indole in the cell or in a culture of the cells, thereby increasing terpenoid production in a cell. Any of the cells described herein can be used in the methods, including bacterial cells, such as *Escherichia coli* cells; Gram-positive cells, such as *Bacillus* cells; yeast cells, such as *Saccharomyces* cells or *Yarrowia* cells; algal cells; plant cell; and any of the engineered cells described herein.

In some embodiments, the step of controlling the accumulation of indole in the cell or in a culture of the cells includes balancing the upstream non-mevalonate isoprenoid pathway with the downstream product synthesis pathways and/or modifying or regulating the indole pathway. In other embodiments, the step of controlling the accumulation of indole in the cell or in a culture of the cells includes or further includes removing the accumulated indole from the fermentation through chemical methods, such as by using absorbents or scavengers.

The one or more terpenoids produced by the cell(s) or in the culture can be a monoterpenoid, a sesquiterpenoid, a diterpenoid, a triterpenoid or a tetraterpenoid. In certain embodiments, the terpenoids is taxadiene or any taxol precursor.

Aspects of the invention relate to methods that include measuring the amount or concentration of indole in a cell that produces one or more terpenoids or in a culture of the cells that produce one or more terpenoids. The methods can include measuring the amount or concentration of indole two or more times. In some embodiments, the measured amount or concentration of indole is used to guide a process of producing one or more terpenoids. In some embodiments, the measured amount or concentration of indole is used to guide strain construction.

Thus, in some aspects the invention provides a method for making a product containing a terpenoid or terpenoid derivative. The method according to this aspect comprises increasing terpenoid production in a cell that produces one or more terpenoids by controlling the accumulation of indole in the cell or in a culture of the cells. The terpenoid, or a derivative of the terpenoid prepared through one or more chemical or enzymatic steps, is incorporated into a product to thereby make the product containing a terpenoid or terpenoid derivative. According to this aspect, the cell expresses components of the MEP pathway, and may be a bacterial cell such as *E. coli* or *B. subtilis*. In various embodiments, the accumulation of indole in the cell or in a culture of the cells is controlled at least in part by balancing an upstream non-mevalonate isoprenoid pathway with a downstream heterologous terpenoid synthesis pathway.

In some embodiments, the product is a food product, food additive, beverage, chewing gum, candy, or oral care product. In such embodiments, the terpenoid or derivative may be a flavor enhancer or sweetener. In some embodiments, the product is a food preservative.

In various embodiments, the product is a fragrance product, a cosmetic, a cleaning product, or a soap. In such embodiments, the terpenoid or derivative may be a fragrance.

In still other embodiments, the product is a vitamin or nutritional supplement.

In some embodiments, the product is a solvent, cleaning product, lubricant, or surfactant.

In some embodiments, the product is a pharmaceutical, and the terpenoid or derivative is an active pharmaceutical ingredient.

In some embodiments, the terpenoid or derivative is polymerized, and the resulting polymer may be elastomeric.

In some embodiments, the product is an insecticide, pesticide or pest control agent, and the terpenoid or derivative is an active ingredient.

In some embodiments, the product is a cosmetic or personal care product, and the terpenoid or derivative is not a fragrance.

These and other aspects of the invention, as well as various embodiments thereof, will become more apparent in reference to the drawings and detailed description of the invention.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A presents a schematic of the two modules, the native upstream MEP isoprenoid pathway (left) and synthetic taxadiene pathway (right). In *E. coli* biosynthetic network, the MEP isoprenoid pathway is initiated by the condensation of the precursors glyceraldehydes-3 phosphate (G3P) and pyruvate (PYR) from glycolysis. The Taxol pathway bifurcation starts from the universal isoprenoid precursors IPP and DMAPP to form first the "linear" precursor Geranylgeranyl diphosphate, and then the "cyclic" taxadiene, a committed and key intermediate to Taxol. The cyclic olefin taxadiene undergoes multiple rounds of stereospecific oxidations, acylations, benzoylation with side chain assembly to, ultimately, form Taxol. FIG. 1B presents a schematic of the multivariate-modular isoprenoid pathway engineering approach for probing the non-linear response in terpenoid accumulation from upstream and downstream pathway engineered cells. Expression of upstream and downstream pathways is modulated by varying the promoter strength (Trc, T5 and T7) or increasing the copy number using different plasmids. Variation of upstream and downstream pathway expression gives different maxima in taxadiene accumulation.

FIGS. 2A-2E. Optimization of taxadiene production by regulating the expression of the up- and down-stream modular pathways. FIG. 2A demonstrates response in taxadiene accumulation to the increase in upstream pathway strengths for constant values of the downstream pathway. FIG. 2B demonstrates the dependence on the downstream pathway for constant increases in the upstream pathway strength. Observed multiple local maxima in taxadiene response depends on the increase in the pathway expression strength upstream or downstream. FIG. 2C demonstrates taxadiene response from strains engineered (17-24) with high upstream pathway overexpressions (20-100) with two different downstream expressions (~30 and ~60) to identify taxadiene response with balanced expressions. Expression of downstream pathway from the low copy plasmid (p5 and p10) under strong promoter T7TG operon was used to modulate these expressions. Note that both upstream and downstream pathway expressed from different plasmids with different promoters can impose plasmid born metabolic burden. FIG. 2D demonstrates modulating the upstream pathway with increasing promoter strength from chromosome with two different downstream expressions (~30 and ~60) to identify the missing search space with reduced toxic effects (strains 25-32). FIG. 2E demonstrates genetic details of the taxadiene producing strains. The numbers corresponding to different strains and its corresponding genotype, E-*E. coli* K12mG1655 ΔrecAΔendA, EDE3-*E. coli* K12mG1655 ΔrecAΔendA with T7 RNA polymerase DE3 construct in the chromosome, MEP-dxs-idi-ispDF operon, GT-GPPS-TS operon, TG-TS-GPPS operon, Ch1-1 copy in chromosome, Trc-Trc promoter, T5-T5 promoter, T7-T7 promoter, p5, p10, p20-~5 (SC101), ~10 (p15), and ~20 (pBR322) copy plasmid.

FIG. 3 demonstrates mass spectrum of metabolite that was detected to correlate inversely with taxadiene production in the strain constructs of FIG. 2. The observed characteristic peaks of the metabolite are 233, 207, 178, 117, 89 and 62. FIG. 3B demonstrates correlation between the isoprenoid byproduct of FIG. 3A and taxadiene. Strains 26-29 and 30-32, all with chromosomally integrated upstream pathway expression, were chosen for consistent comparison. In strains 26-29 and 30-32, upstream expression increased by changing the promoters from Trc, to T5 and T7 respectively. The two sets of strains differ only in the expression of the downstream pathway with the second set (30-32) having twice the level of expression of the first. With the first set, optimal balancing is achieved with strain 26, which uses the Trc promoter for upstream pathway expression and also shows the lowest metabolite accumulation. With strains 30-32, strain 31 shows the lowest accumulation of metabolite and highest production of taxadiene. The data demonstrate the inverse correlation observed between the unknown metabolite and taxadiene production.

FIG. 4A demonstrates relative transcript level DXS gene expression quantified from different upstream expressions modulated using promoters and plasmids under two different downstream expressions. FIG. 4B demonstrates relative transcript level TS gene expression quantified from two different downstream expression modulated using p5T7 and p10T7 plasmids under different upstream expressions. Our gene expression analysis directly supported the hypothesis, with increase in plasmid copy number (5, 10 and 20) and promoter strength (Trc, T5 and T7) the expression of the upstream and downstream pathways can be modulated. FIG. 4C demonstrates cell growth of the engineered strains 25-29. The growth phenotype was affected from activation of isoprenoid metabolism (strain 26), recombinant protein expression (strain 25) and plasmid born metabolic burden (control vs engineered strains). FIG. 4D demonstrates growth phenotypes of strains 17, 22, 25-32. The black color lines are the taxadiene producing engineered strains and the gray color lines are control strains without downstream expression carrying an empty plasmid with promoter and multi cloning sites. The growth was correlated to the activation of the terpenoid metabolism, plasmid born metabolic burden as well the recombinant protein expression.

FIG. 5A demonstrates a schematic of the conversion of taxadiene to taxadiene 5α-ol to Taxol. FIG. 5B demonstrates transmembrane engineering and construction of one-component chimera protein from taxadiene 5α-ol hydroxylsase (T5αOH) and *Taxus* cytochrome p450 reductase (TCPR). 1 and 2 represents the full length proteins of T5αOH and TCPR identified with 42 and 74 amino acid TM regions respectively, 3-chimera enzymes generated from the three different TM engineered T5αOH constructs, (At8T5αOH, At24T5αOH and At42T5αOH constructed by fusing 8 residue synthetic peptide (A) to 8, 24 and 42 AA truncated T5αOH) through a translational fusion with 74 AA truncated TCPR (tTCPR) using 5 residue GSTGS linker peptide. FIG. 5C demonstrates functional activity of At8T5αOH-tTCPR, At24T5αOH-tTCPR and At42T5αOH-tTCPR constructs transformed into taxadiene producing strain 18. FIG. 5D demonstrates a time course profile of taxadien-5α-ol accumulation and growth profile of the strain 18-At24T5αOH-tTCPR fermented in a 1 L bioreactor.

FIG. 8B presents a representative GC-profile from the strains 26-28 to demonstrate the change in taxadiene and metabolite accumulation. Numbers in the chromatogram 1 and 2 corresponding to metabolite and taxadiene peak respectively. FIG. 8C presents a GC-MS profile of metabolite (1) and taxadiene (2) respectively. The observed characteristic peaks of the metabolite are 233, 207, 178, 117, 89 and 62. Taxa-4(20),11,12-diene characteristic ion m/z 272($P^+$), 257 ($P^+$—CH3), 229 ($P^+$—$C_3H_7$); 121, 122, 123 (C-ring fragment cluster).[60] The peak marked with a star is the internal standard caryophylene.

FIG. 9A presents a GC profile of the hexane:ether (8:2) extract from three constructs (A-At8T5αOH-tTCPR, t24T5αOH-tTCPR and At42T5αOH-tTCPR) transferred to strain 26 and fermented for 5 days. 1, 2 and 3 labels in the peaks corresponding to the taxadiene, taxadien-5α-ol and 5(12)-Oxa-3(11)-cyclotaxane (OCT) respectively. FIG. 9B demonstrates the production of taxa-4(20),11,12-dien-5α-ol and OCT quantified from the three strains. FIGS. 9C and 9D demonstrate GC-MS profile of taxa-4(20),11,12-dien-5α-ol and OCT and the peaks corresponding to the fragmentation was compared with the authentic standards and previous reports[42,47] GC-MS analysis confirmed the mass spectrum identity to authentic taxa-4(20),11,12-dien-5α-ol with characteristic ion m/z 288($P^+$), 273 ($P^+$—$H_2O$), 255 ($P^+$—$H_2O$—CH3).

FIG. 14A demonstrates relative expression of idi, ispD and ispF genes with increasing upstream pathway strength and downstream strength at 31 arbitrary units, and FIG. 14B demonstrates relative expression of idi, ispD and ispF genes with increasing upstream pathway strength and downstream strength at 61 arbitrary units. As expected the gene expression increased as the upstream pathway strength increased. The corresponding strain numbers are indicated in the bar graph. The relative expression was quantified using the expression of the housekeeping rrsA gene. Data are mean +/−SD for four replicates.

FIG. 15A demonstrates an inverse correlation between taxadiene and Indole. Strains 26 to 28 and 30 to 32, all with chromosomally integrated upstream pathway expression, were chosen for consistent comparison. The two sets of strains differ only in the expression of the downstream pathway with the second set (30 to 32) having twice the level of expression of the first. In strains 26 to 28 and 30 to 32, upstream expression increased by changing the promoters from Trc, to T5 and T7, respectively. With the first set, optimal balancing is achieved with strain 26, which uses the Trc promoter for upstream pathway expression and also shows the lowest indole accumulation. With strains 30 to 32, strain 31 shows the lowest accumulation of indole and highest production of taxadiene. The fold improvements are relative to strain 25 and 29, respectively, for the two sets. FIG. 15B demonstrates the effect of externally-introduced indole on taxadiene production for the high-producing strain 26. Different concentrations of indole were introduced into cultures of cells cultured in minimal media with 0.5% yeast extract. Taxadiene production was significantly reduced as indole concentration increased from 50 mg/L to 100 mg/L. FIG. 15C demonstrates the effect of externally-introduced indole on cell growth for engineered strains of E. coli. Data are mean +/−SD for three replicates. Strains devoid of the downstream pathway and with different strengths of the upstream pathway (1, 2, 6, 21, 40 and 100) were selected. Strain 26, the high taxadiene producer, exhibits the strongest inhibition.

FIGS. 16A and 16C demonstrate a gas chromatogram and mass spectrum of the unknown metabolite extracted using hexane from cell culture. FIGS. 16B and 16D correspond to the gas chromatogram and mass spectrum of pure indole dissolved in hexane. Further to confirm the chemical identity, the metabolite was extracted from the fermentation broth using hexane extraction and purified by silica column chromatography using hexane:ethylacetate (8:2) as eluent. The purity of the compound was confirmed by TLC and GC-MS. $^1$HNMR and $^{13}$CNMR spectra confirmed the chemical identity of the metabolite as indole. FIG. 16E demonstrates $^1$HNMR spectrum of indole extracted from cell culture (CDCl3, 400 MHz) δ: 6.56 (d, 1H, Ar C—H), 7.16 (m, 3H, Ar C—H), 7.38 (d, 1H, Ar C—H), 7.66 (d, 1H, Ar C—H), 8.05 (b, 1H, Indole NH). FIG. 16F demonstrates $^{13}$CNMR δ: 135.7, 127.8, 124.2, 122, 120.7, 119.8, 111, 102.6. FIG. 16G demonstrates is the $^1$HNMR spectrum of pure indole.

FIG. 17A demonstrates time courses of taxadiene accumulation. FIG. 17B demonstrates time courses of cell growth. FIG. 17C demonstrates time courses of acetic acid accumulation and FIG. 17D demonstrates time courses of total substrate (glycerol) addition for strains 22, 17 and 26 during 5 days of fed batch bioreactor cultivation in 1 L-bioreactor vessels under controlled pH and oxygen conditions with minimal media and 0.5% yeast extract. After glycerol depletes to ~0.5 to 1 g/L in the fermentor, 3 g/L of glycerol was introduced into the bioreactor during the fermentation. Data are mean of two replicate bioreactors.

DETAILED DESCRIPTION OF THE INVENTION

Figure 1A:
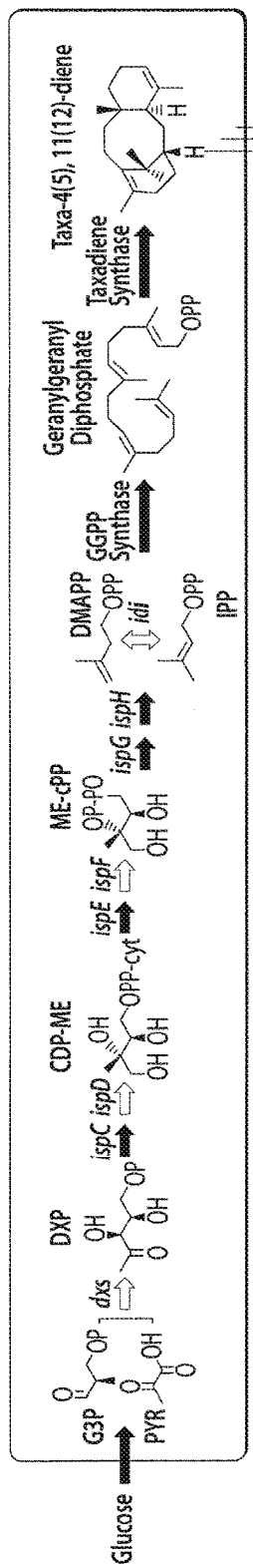
FIGS. 1A and 1B. Multivariate-modular isoprenoid pathway engineering reveals strong non-linear response in terpenoid accumulation. To increase the flux through the upstream MEP pathway, we targeted reported bottleneck enzymatic steps (dxs, idi, ispD and ispF) for overexpression by an operon (dxs-idi-ispDF).[28] To channel the overflow flux from the universal isoprenoid precursors, IPP and DMAPP, towards Taxol biosynthesis, a synthetic operon of downstream genes GGPP synthase (G) and Taxadiene synthase (T)[16] was constructed. The upstream isoprenoid and downstream synthetic taxadiene pathways were placed under the control of inducible promoters to control their relative gene expression.

Taxol is a potent anticancer drug first isolated as a natural product from the *Taxus brevifolia* Pacific yew tree. However, reliable and cost-efficient production of Taxol or Taxol analogs by traditional production routes from plant extracts is limited. Here, we report a multivariate-modular approach to metabolic pathway engineering to amplify by ~15000 fold the production of taxadiene in an engineered *Escherichia coli*. Taxadiene, the first committed Taxol intermediate, is the biosynthetic product of the non-mevalonate pathway in *E. coli* comprising two modules: the native upstream pathway forming Isopentenyl Pyrophosphate (IPP) and a heterologous downstream terpenoid-forming pathway. Systematic multivariate search identified conditions that optimally balance the two pathway modules to minimize accumulation of inhibitory intermediates and flux diversion to side products. We also engineered the next step, after taxadiene, in Taxol biosynthesis, a P450-based oxidation step, that yielded >98% substrate conversion and present the first example of in vivo production of any functionalized Taxol intermediates in *E. coli*. The modular pathway engineering approach not only highlights the complexity of multi-step pathways, but also allowed accumulation of high taxadiene and taxadien-5α-ol titers (~300 mg/L and 60 mg/L, respectively) in small-scale fermentations, thus exemplifying the potential of microbial production of Taxol and its derivatives.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Microbial production of terpenoids such as taxadiene is demonstrated herein. When expressed at satisfactory levels, microbial routes reduce dramatically the cost of production of such compounds. Additionally, they utilize cheap, abundant and renewable feedstocks (such as sugars and other carbohydrates) and can be the source for the synthesis of numerous derivatives that may exhibit far superior properties than the original compound. A key element in the cost-competitive production of compounds of the isoprenoid pathway using a microbial route is the amplification of this pathway in order to allow the overproduction of these molecules. Described herein are methods that enhance or amplify the flux towards terpenoid production in *Escherichia coli* (*E. coli*). Specifically, methods are provided to amplify the metabolic flux to the synthesis of isopentenyl pyrophosphate (IPP) (a key intermediate for the production of isoprenoid compounds), dimethylallyl pyrophosphate (DMAPP), geranyl diphosphate (GPP), farnesyl diphosphate (FPP), geranylgeranyl diphosphate (GGPP), and farnesyl geranyl diphosphate (FGPP), paclitaxel (Taxol), ginkolides, geraniol, farnesol, geranylgeraniol, linalool, isoprene, monoterpenoids such as menthol, carotenoids such as lycopene, polyisoprenoids such as polyisoprene or natural rubber, diterpenoids such as eleutherobin, and sesquiterpenoids such as artemisinin.

Aspects of the invention relate to the production of terpenoids. As used herein, a terpenoid, also referred to as an isoprenoid, is an organic chemical derived from a five-carbon isoprene unit. Several non-limiting examples of terpenoids, classified based on the number of isoprene units that they contain, include: hemiterpenoids (1 isoprene unit), monoterpenoids (2 isoprene units), sesquiterpenoids (3 isoprene units), diterpenoids (4 isoprene units), sesterterpenoids (5 isoprene units), triterpenoids (6 isoprene units), tetraterpenoids (8 isoprene units), and polyterpenoids with a larger number of isoprene units. In some embodiments, the terpenoid that is produced is taxadiene. In some embodiments, the terpenoid that is produced is Citronellol, Cubebol, Nootkatone, Cineol, Limonene, Eleutherobin, Sarcodictyin, Pseudopterosins, Ginkgolides, Stevioside, Rebaudioside A, sclareol, labdenediol, levopimaradiene, sandracopimaradiene or isopemaradiene.

Described herein are methods and compositions for optimizing production of terpenoids in cells by controlling expression of genes or proteins participating in an upstream pathway and a downstream pathway. The upstream pathway involves production of isopentenyl pyrophosphate (IPP) and dimethylallyl pyrophosphate (DMAPP), which can be achieved by two different metabolic pathways: the mevalonic acid (MVA) pathway and the MEP (2-C-methyl-D-erythritol 4-phosphate) pathway, also called the MEP/DOXP (2-C-methyl-D-erythritol 4-phosphate/1-deoxy-D-xylulose 5-phosphate) pathway, the non-mevalonate pathway or the mevalonic acid-independent pathway.

The downstream pathway is a synthetic pathway that leads to production of a terpenoids and involves recombinant gene expression of a terpenoid synthase (also referred to as terpene cyclase) enzyme, and a geranylgeranyl diphosphate synthase (GGPPS) enzyme. In some embodiments, a terpenoid synthase enzyme is a diterpenoid synthase enzyme. Several non-limiting examples of diterpenoid synthase enzymes include casbene synthase, taxadiene synthase, levopimaradiene synthase, abietadiene synthase, isopimaradiene synthase, ent-copalyl diphosphate synthase, syn-stemar-13-ene synthase, syn-stemod-13(17)-ene synthase, syn-pimara-7,15-diene synthase, ent-sandaracopimaradiene synthase, ent-cassa-12,15-diene synthase, ent-pimara-8(14), 15-diene synthase, ent-kaur-15-ene synthase, ent-kaur-16-ene synthase, aphidicolan-16β-ol synthase, phyllocladan-16α-ol synthase, fusicocca-2,10(14)-diene synthase, and terpentetriene cyclase.

Surprisingly, as demonstrated in the Examples section, optimization of terpenoid synthesis by manipulation of the upstream and downstream pathways described herein, was not a simple linear or additive process. Rather, through complex combinatorial analysis, optimization was achieved through balancing components of the upstream and downstream pathways. Unexpectedly, as demonstrated in FIGS. 1 and 2, taxadiene accumulation exhibited a strong non-linear dependence on the relative strengths of the upstream MEP and downstream synthetic taxadiene pathways.

Aspects of the invention relate to controlling the expression of genes and proteins in the MEP pathway for optimized production of a terpenoid such as taxadiene. Optimized production of a terpenoid refers to producing a higher amount of a terpenoid following pursuit of an optimization strategy than would be achieved in the absence of such a strategy. It should be appreciated that any gene and/or protein within the MEP pathway is encompassed by methods and compositions described herein. In some embodiments, a gene within the MEP pathway is one of the following: dxs, ispC, ispD, ispE, ispF, ispG, ispH, idi, ispA or ispB. Expression of one or more genes and/or proteins within the MEP pathway can be upregulated and/or downregulated. In certain embodiments, upregulation of one or more genes and/or proteins within the MEP pathway can be combined with downregulation of one or more genes and/or proteins within the MEP pathway.

It should be appreciated that genes and/or proteins can be regulated alone or in combination. For example, the expression of dxs can be upregulated or downregulated alone or in combination with upregulation or downregulation of expression of one or more of ispC, ispD, ispE, ispF, ispG, ispH, idi, ispA and ispB. The expression of ispC can be upregulated or downregulated alone or in combination with upregulation or downregulation of expression of one or more of dxs, ispD, ispE, ispF, ispG, ispH, idi, ispA and ispB. The expression of ispD can be upregulated or downregulated alone or in combination with upregulation or downregulation of expression of one or more of dxs, ispC, ispE, ispF, ispG, ispH, idi, ispA and ispB. The expression of ispE can be upregulated or downregulated alone or in combination with upregulation or downregulation of expression of one or more of dxs, ispC, ispD, ispF, ispG, ispH, idi, ispA and ispB. The expression of ispF can be upregulated or downregulated alone or in combination with upregulation or downregulation of expression of one or more of dxs, ispC, ispD, ispE, ispG, ispH, idi, ispA and ispB. The expression of ispG can be upregulated or downregulated alone or in combination with upregulation or downregulation of expression of one or more of dxs, ispC, ispD, ispE, ispF, ispH, idi, ispA and ispB. The expression of ispH can be upregulated or downregulated alone or in combination with upregulation or downregulation of expression of one or more of dxs, ispC, ispD, ispE, ispF, ispG, idi, ispA and ispB. The expression of idi can be upregulated or downregulated alone or in combination with upregulation or downregulation of expression of one or more of dxs, ispC, ispD, ispE, ispF, ispG, ispH, ispA and ispB. The expression of ispA can be upregulated or downregulated alone or in combination with upregulation or downregulation of expression of one or more of dxs, ispC, ispD, ispE, ispF, ispG, ispH, idi and ispB. The expression of ispB can be upregulated or downregulated alone or in combination with upregulation or downregulation of expression of one or more of dxs, ispC, ispD, ispE, ispF, ispG, ispH, idi and ispA. In some embodiments, expression of the gene and/or protein of one or more of dxs, ispC, ispD, ispE, ispF, ispG, ispH, and idi is upregulated while expression of the gene and/or protein of ispA and/or ispB is downregulated.

Expression of genes within the MEP pathway can be regulated in a modular method. As used herein, regulation by a modular method refers to regulation of multiple genes together. For example, in some embodiments, multiple genes within the MEP pathway are recombinantly expressed on a contiguous region of DNA, such as an operon. It should be appreciated that a cell that expresses such a module can also express one or more other genes within the MEP pathway either recombinantly or endogenously.

A non-limiting example of a module of genes within the MEP pathway is a module containing the genes dxs, idi, ispD and ispF, as presented in the Examples section, and referred to herein as dxs-idi-ispDF. It should be appreciated that modules of genes within the MEP pathway, consistent with aspects of the invention, can contain any of the genes within the MEP pathway, in any order.

Expression of genes and proteins within the downstream synthetic terpenoid synthesis pathway can also be regulated in order to optimize terpenoid production. The synthetic downstream terpenoid synthesis pathway involves recombinant expression of a terpenoid synthase enzyme and a GGPPS enzyme. Any terpenoid synthase enzyme, as discussed above, can be expressed with GGPPS depending on the downstream product to be produced. For example, taxadiene synthase is used for the production of taxadiene. Recombinant expression of the taxadiene synthase enzyme and the GGPPS enzyme can be regulated independently or together. In some embodiments the two enzymes are regulated together in a modular fashion. For example the two enzymes can be expressed in an operon in either order (GGPPS-TS, referred to as "GT," or TS-GGPPS, referred to as "TG").

Manipulation of the expression of genes and/or proteins, including modules such as the dxs-idi-ispDF operon, and the TS-GGPPS operon, can be achieved through methods known to one of ordinary skill in the art. For example, expression of the genes or operons can be regulated through selection of promoters, such as inducible promoters, with different strengths. Several non-limiting examples of promoters include Trc, T5 and T7. Additionally, expression of genes or operons can be regulated through manipulation of the copy number of the gene or operon in the cell. For example, in certain embodiments, a strain containing an additional copy of the dxs-idi-ispDF operon on its chromosome under Trc promoter control produces an increased amount of taxadiene relative to one overexpressing only the synthetic downstream pathway. In some embodiments, expression of genes or operons can be regulated through manipulating the order of the genes within a module. For example, in certain embodiments, changing the order of the genes in a downstream synthetic operon from GT to TG results in a 2-3 fold increase in taxadiene production. In some embodiments, expression of genes or operons is regulated through integration of one or more genes or operons into a chromosome. For example, in certain embodiments, integration of the upstream dxs-idi-ispDF operon into the chromosome of a cell results in increased taxadiene production.

It should be appreciated that the genes associated with the invention can be obtained from a variety of sources. In some embodiments, the genes within the MEP pathway are bacterial genes such as *Escherichia coli* genes. In some embodiments, the gene encoding for GGPPS is a plant gene. For example, the gene encoding for GGPPS can be from a species of *Taxus* such as *Taxus canadensis* (*T. canadensis*). In some embodiments, the gene encoding for taxadiene synthase is a plant gene. For example, the gene encoding for taxadiene synthase can be from a species of *Taxus* such as *Taxus brevifolia* (*T. brevifolia*). Representative GenBank Accession numbers for *T. canadensis* GGPPS and *T. brevifolia* taxadiene synthase are provided by AF081514 and U48796, the sequences of which are incorporated by reference herein in their entireties.

As one of ordinary skill in the art would be aware, homologous genes for use in methods associated with the invention can be obtained from other species and can be identified by homology searches, for example through a protein BLAST search, available at the National Center for Biotechnology Information (NCBI) internet site (www.ncbi.nlm.nih.gov). Genes and/or operons associated with the invention can be cloned, for example by PCR amplification and/or restriction digestion, from DNA from any source of DNA which contains the given gene. In some embodiments, a gene and/or operon associated with the invention is synthetic. Any means of obtaining a gene and/or operon associated with the invention is compatible with the instant invention.

In some embodiments, further optimization of terpenoid production is achieved by modifying a gene before it is recombinantly expressed in a cell. In some embodiments, the GGPPS enzyme has one or more of the follow mutations: A162V, G140C, L182M, F218Y, D160G, C184S, K367R, A151T, M185I, D264Y, E368D, C184R, L331I, G262V, R365S, A14D, S239C, G295D, I276V, K343N, P183S, I172T, D267G, I149V, T234I, E153D and T259A. In some embodiments, the GGPPS enzyme has a mutation in residue S239 and/or residue G295. In certain embodiments, the GGPPS enzyme has the mutation S239C and/or G295D.

In some embodiments, modification of a gene before it is recombinantly expressed in a cell involves codon optimization for expression in a bacterial cell. Codon usages for a variety of organisms can be accessed in the Codon Usage Database (www.kazusa.or.jp/codon/). Codon optimization, including identification of optimal codons for a variety of organisms, and methods for achieving codon optimization, are familiar to one of ordinary skill in the art, and can be achieved using standard methods.

In some embodiments, modifying a gene before it is recombinantly expressed in a cell involves making one or more mutations in the gene before it is recombinantly expressed in a cell. For example, a mutation can involve a substitution or deletion of a single nucleotide or multiple nucleotides. In some embodiments, a mutation of one or more nucleotides in a gene will result in a mutation in the protein produced from the gene, such as a substitution or deletion of one or more amino acids.

In some embodiments, it may be advantageous to use a cell that has been optimized for production of a terpenoid. For example, in some embodiments, a cell that overexpresses one or more components of the non-mevalonate (MEP) pathway is used, at least in part, to amplify isopentenyl diphosphate (IPP) and dimethylallyl diphosphate (DMAPP), substrates of GGPPS. In some embodiments, overexpression of one or more components of the non-mevalonate (MEP) pathway is achieved by increasing the copy number of one or more components of the non-mevalonate (MEP) pathway. For example, copy numbers of components at rate-limiting steps in the MEP pathway such as (dxs, ispD, ispF, idi) can be amplified, such as by additional episomal expression.

In some embodiments "rational design" is involved in constructing specific mutations in proteins such as enzymes. As used herein, "rational design" refers to incorporating knowledge of the enzyme, or related enzymes, such as its three dimensional structure, its active site(s), its substrate(s) and/or the interaction between the enzyme and substrate, into the design of the specific mutation. Based on a rational design approach, mutations can be created in an enzyme which can then be screened for increased production of a terpenoid relative to control levels. In some embodiments, mutations can be rationally designed based on homology modeling. As used herein, "homology modeling" refers to the process of constructing an atomic resolution model of one protein from its amino acid sequence and a three-dimensional structure of a related homologous protein.

In some embodiments, random mutations can be made in a gene, such as a gene encoding for an enzyme, and these mutations can be screened for increased production of a terpenoid relative to control levels. For example, screening for mutations in components of the MEP pathway, or components of other pathways, that lead to enhanced production of a terpenoid may be conducted through a random mutagenesis screen, or through screening of known mutations. In some embodiments, shotgun cloning of genomic fragments could be used to identify genomic regions that lead to an increase in production of a terpenoid, through screening cells or organisms that have these fragments for increased production of a terpenoid. In some cases one or more mutations may be combined in the same cell or organism.

In some embodiments, production of a terpenoid in a cell can be increased through manipulation of enzymes that act in the same pathway as the enzymes associated with the invention. For example, in some embodiments it may be advantageous to increase expression of an enzyme or other factor that acts upstream of a target enzyme such as an enzyme associated with the invention. This could be achieved by over-expressing the upstream factor using any standard method.

Optimization of protein expression can also be achieved through selection of appropriate promoters and ribosome binding sites. In some embodiments, this may include the selection of high-copy number plasmids, or low or medium-copy number plasmids. The step of transcription termination can also be targeted for regulation of gene expression, through the introduction or elimination of structures such as stem-loops.

Aspects of the invention relate to expression of recombinant genes in cells. The invention encompasses any type of cell that recombinantly expresses genes associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. Preferably the yeast strain is a *S. cerevisiae* strain or a *Yarrowia* spp. strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell. It should be appreciated that some cells compatible with the invention may express an endogenous copy of one or more of the genes associated with the invention as well as a recombinant copy. In some embodiments, if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of a terpenoid.

Further aspects of the invention relate to screening for bacterial cells or strains that exhibit optimized terpenoid production. As described above, methods associated with the invention involve generating cells that overexpress one or more genes in the MEP pathway. Terpenoid production from culturing of such cells can be measured and compared to a control cell wherein a cell that exhibits a higher amount of a terpenoid production relative to a control cell is selected as a first improved cell. The cell can be further modified by recombinant expression of a terpenoid synthase enzyme and a GGPPS enzyme. The level of expression of one or more of the components of the non-mevalonate (MEP) pathway, the terpenoid synthase enzyme and/or the GGPPS enzyme in the cell can then be manipulated and terpenoid production can be measured again, leading to selection of a second improved cell that produces greater amounts of a terpenoid than the first improved cell. In some embodiments, the terpenoid synthase enzyme is a taxadiene synthase enzyme.

Figure 3A:
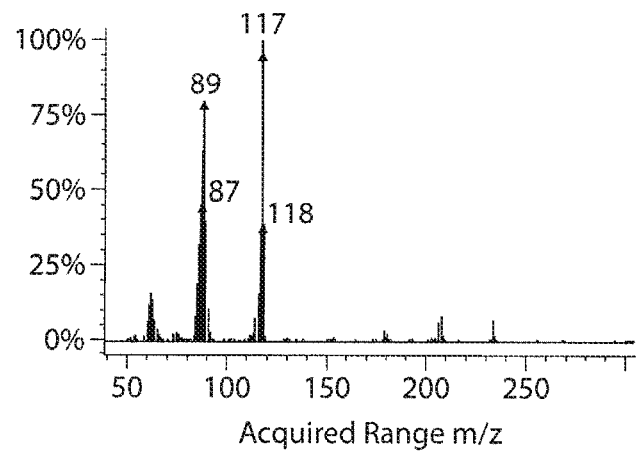
FIGS. 3A and 3B. Metabolite inversely correlates with taxadiene production.
Figure 3B:
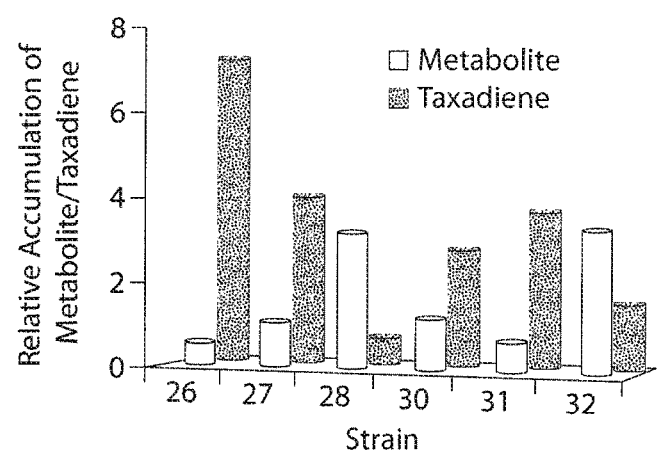
Figure 6:
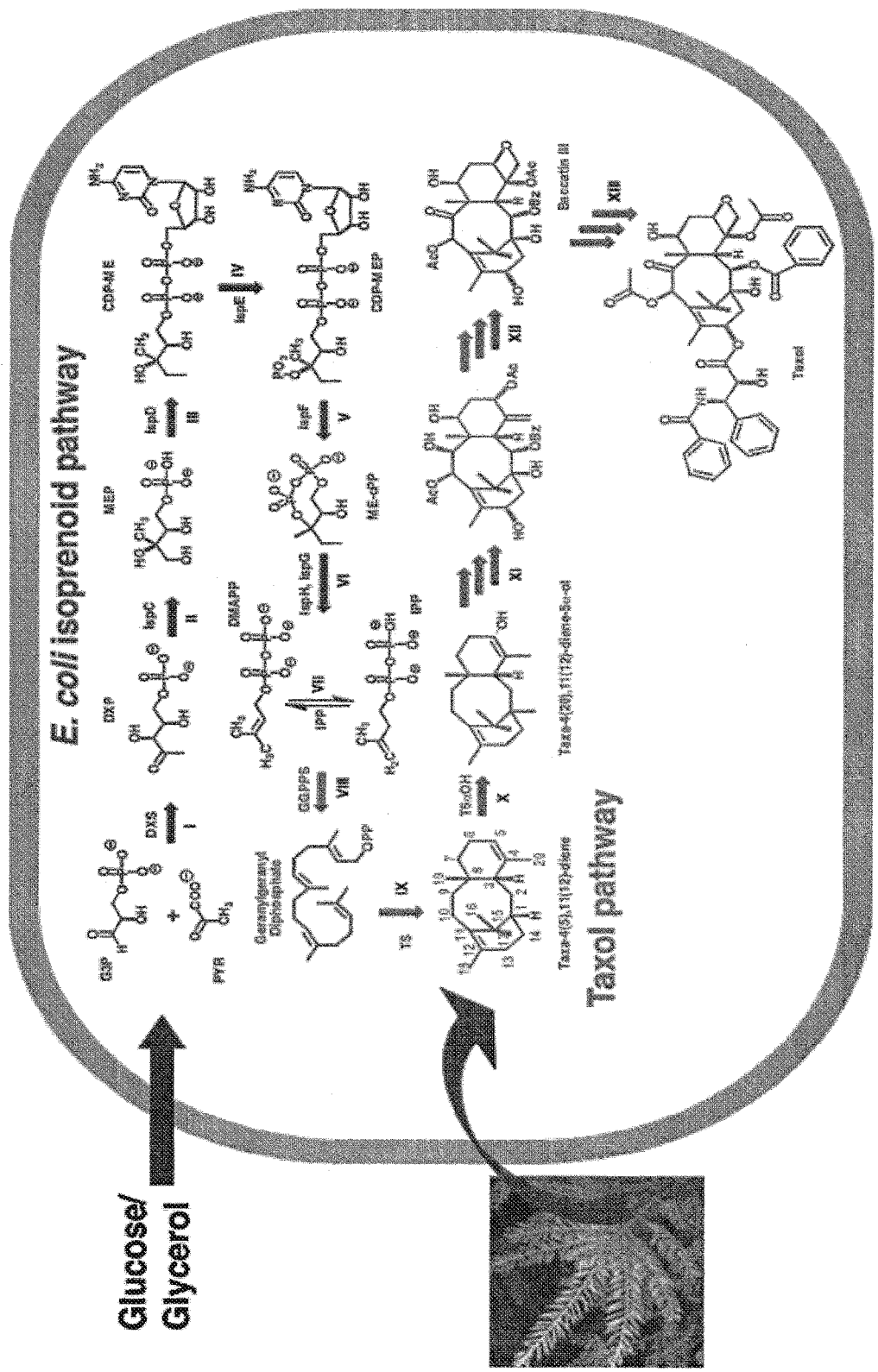
FIG. 6. Biosynthetic scheme for taxol production in *E. coli*. Schematics of the two modules, native upstream isoprenoid pathway (left) and synthetic Taxol pathway (right). In *E. coli* biosynthetic network, divergence of MEP isoprenoid pathway initiates from the precursors glyceraldehyde-3 phosphate (G3P) and Pyruvate (PYR) from glycolysis (I-V). The Taxol pathway bifurcation starts from the *E. coli* isoprenoid precursor IPP and DMAPP to "linear" precursor Geranylgeranyl diphosphate (VIII), "cyclic" taxadiene (IX), "oxidized" taxadiene 5α-ol (X) to multiple rounds of stereospecific oxidations, acylations, benzoylations and epoxidation for early precursor Baccatin III (XII) and finally with side chain assembly to Taxol (XIII) DXP-1-deoxy-D-xylulose-5-phosphate, MEP-2C-methyl-D-erythritol-4-phosphate, CDP-ME-4-diphosphocytidyl-2Cmethyl-D-erythritol, CDP-MEP-4-diphosphocytidyl-2C-methyl-D-erythritol-2-phosphate, ME-cPP-2C-methyl-D-erythritol-2, 4-cyclodiphosphate, IPP-isopentenyl diphosphate, DMAPP-dimethylallyl diphosphate. The genes involved biosynthetic pathways from G3P and PYR to Taxol. DXS-1-deoxy-D-xylulose-5-phosphate synthase, ispC-1-Deoxy-D-xylulose-5-phosphate reductoisomerase, IspD-4-diphosphocytidyl-2C-methyl-D-erythritol synthase, IspE-4-diphosphocytidyl-2-C-methyl-D-erythritol kinase, IspF-2C-Methyl-D-erythritol-2,4-cyclodiphosphate Synthase, IspG-1-hydroxy-2-methyl-2-(E)-butenyl-4-diphosphate synthase, IspH-4-hydroxy-3-methyl-2-(E)-butenyl-4-diphosphate reductase IDI-isopentenyl-diphosphate isomerase, GGPPS-geranyl geranyldiphosphate synthase, Taxadiene synthase, Taxoid 5α-hydroxylase, Taxoid-5α-O-acetyltransferase, Taxoid 13α-hydroxylase, Taxoid 10β-hydroxylase, Taxoid 2α-hydroxylase, Taxoid 2-O-benzoyltransferase, Taxoid 7β-hydroxylase, Taxoid 10-O-acetyltransferase, Taxoid 1β-hydroxylase*, Taxoid 9α-hydroxylase, Taxoid 9-keto-oxidase*, Taxoid C4,C20-β-epoxidase*, Phenylalanine aminomutase, Side chain CoA-ligase*, Taxoid 13 O-phenylpropanoyltransferase, Taxoid 2'-hydroxylase*, Taxoid 3'-N-benzoyltransferase.[216,219] marked genes are yet to be identified or characterized.
Figure 15A:
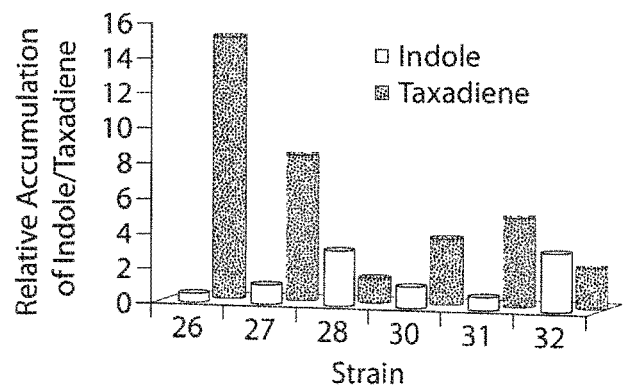
FIGS. 15A-15C. Impact of metabolite byproduct Indole accumulation on taxadiene production and growth.

Further aspects of the invention relate to the identification and characterization (via GC-MS) of a previously unknown metabolite in bacterial E. coli cells (FIGS. 3 and 6). The level of accumulation of the newly identified metabolite, indole, can be controlled by genetically manipulating the microbial pathway by the overexpression, down regulation or mutation of the isoprenoid pathway genes. The metabolite indole anti-correlates as a direct variable to the taxadiene production in engineered strains (FIGS. 3, 6 and 15). Further controlling the accumulation of indole for improving the flux towards terpenoid biosynthesis in bacterial systems (specifically in cells, such as E. coli cells) or other cells, can be achieved by balancing the upstream non-mevalonate isoprenoid pathway with the downstream product synthesis pathways or by modifications to or regulation of the indole pathway. In so doing, the skilled person can reduce or control the accumulation of indole and thereby reduce the inhibitory effect of indole on the production of taxadiene, and other terpenoids derived from the described pathways, such as: monoterpenoids, sesquiterpenoids (including amorphadiene), diterpenoids (including levopimaradiene), triterpenes, and tetraterpenes. Other methods for reducing or controlling the accumulation of indole include removing the accumulated indole from the fermentation through chemical methods such as by using absorbents, scavengers, etc.

In other embodiments, methods are provided that include measuring the amount or concentration of indole in a cell that produces one or more terpenoids or in a culture of the cells that produce one or more terpenoids. The amount or concentration of indole can be measured once, or two or more times, as suitable, using methods known in the art and as described herein. Such methods can be used to guide processes of producing one or more terpenoids, e.g., in process improvement. Such methods can be used to guide strain construction, e.g., for strain improvement.

The identification of the means to achieve this balancing yielded a 15000 fold improvement in the overproduction of terpenoids such as taxadiene, compared to wild type bacterial cells, expressed with a heterologous taxadiene biosynthetic pathway. The production was further increased through modified fermentation methods that yielded concentrations of approximately 2 g/L, which is 1500 fold higher compared to any prior reported taxadiene production. As demonstrated herein, by genetically engineering the non-mevalonate isoprenoid pathway in E. coli the accumulation of this metabolite can now be controlled which regulates the flux towards the isoprenoid biosynthesis in bacterial E. coli cells. Also demonstrated herein is further channeling of the taxadiene production into the next key precursor to Taxol, taxadien-5α-ol, achieved through engineering the oxidation chemistry for Taxol biosynthesis. Example 5 presents the first successful extension of the synthetic pathway from taxadiene to taxadien-5α-ol. Similar to the majority of other terpenoids, the Taxol biosynthesis follows the unified fashion of "two phase" biosynthetic process, (i) the "cyclase phase" of linear coupling of the prenyl precursors (IPP and DMAPP) to GGPP followed by the molecular cyclization and rearrangement for the committed precursor taxadiene (FIG. 6, VIII-IX).[57, 58] After the committed precursor, (ii) the "oxidation phase", the cyclic olefin taxadiene core structure is then functionalized by seven cytochrome P450 oxygenases together with its redox partners, decorated with two acetate groups and a benzoate group by acyl and aroyl CoA-dependent transferases, keto group by keto-oxidase, and epoxide group by epoxidase lead to the late intermediate baccatin III, to which the C13 side chain is attached for Taxol ((FIG. 6, X-XIII)[15] Although a rough sequential order of the early oxidation phase reactions are predicted, the precise timing/order of some of the hydroxylations, acylations and benzoylation reactions are uncertain. However it is clear that the early bifurcation starts from the cytochrome p450 mediated hydroxylation of taxadiene core at C5 position followed the downstream hydroxylations using a homologous family of cytochrome p450 enzymes with high deduced similarity to each other (>70%) but with limited resemblance (<30%) to other plant p450's.[41,59] In addition, the structural and functional diversity with the possible evolutionary analysis implicit that the taxadiene-5α-ol gene can be the parental sequence from which the other hydroxylase genes in the Taxol biosynthetic pathway evolved, reflecting the order of hydroxylations.[15]

Further aspects of the invention relate to chimeric P450 enzymes. Functional expression of plant cytochrome P450 has been considered challenging due to the inherent limitations of bacterial platforms, such as the absence of electron transfer machinery, cytochrome P450 reductases, and translational incompatibility of the membrane signal modules of P450 enzymes due to the lack of an endoplasmic reticulum.

Figure 5A:
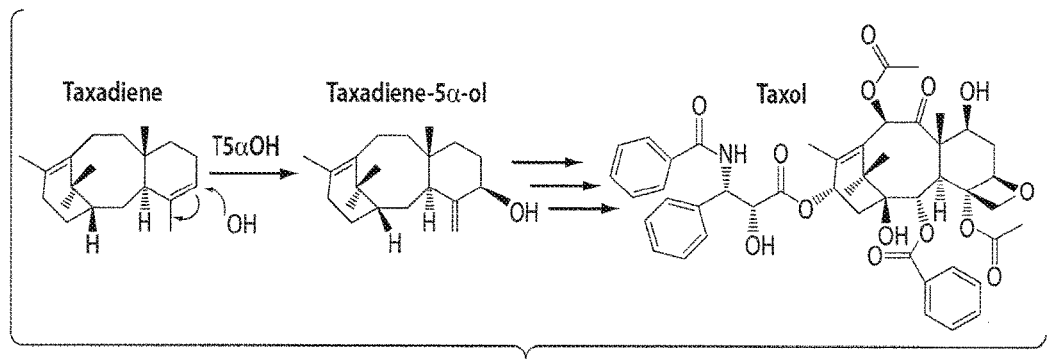
FIGS. 5A-5D. Engineering Taxol p450 oxidation chemistry in *E. coli*.
Figure 5B:
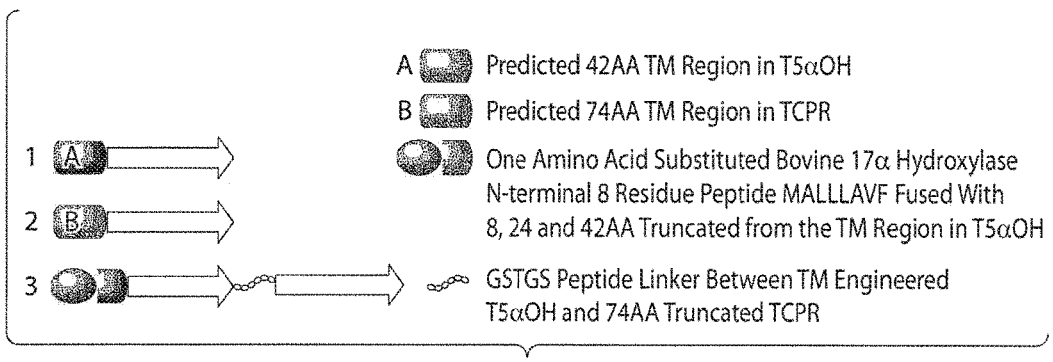
Figure 5C:
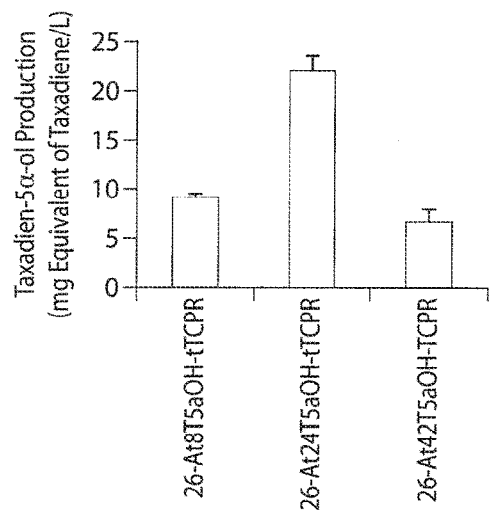

In some embodiments, the taxadiene-5a-hydroxylase associated with methods of the invention is optimized through N-terminal transmembrane engineering and/or the generation of chimeric enzymes through translational fusion with a CPR redox partner. In some embodiments, the CPR redox partner is a Taxus cytochrome P450 reductase (TCPR; FIG. 5b). In certain embodiments, cytochrome P450 taxadiene-5α-hydroxylase (T5αOH) is obtained from Taxus cuspidate (GenBank Accession number AY289209, the sequence of which is incorporated by reference herein). In some embodiments, NADPH:cytochrome P450 reductase (TCPR) is obtained from Taxus cuspidate (GenBank Accession number AY571340, the sequence of which is incorporated by reference herein).

The taxadiene 5α-hydroxylase and TCPR can be joined by a linker such as GSTGS (SEQ ID NO:50). In some embodiments, taxadiene 5α-hydroxylase and/or TCPR are truncated to remove all or part of the transmembrane region of one or both proteins. For example, taxadiene 5α-hydroxylase in some embodiments is truncated to remove 8, 24, or 42 N-terminal amino acids. In some embodiments, the N-terminal 74 amino acids of TCPR are truncated. An additional peptide can also be fused to taxadiene 5α-hydroxylase. For example, one or more amino acids from bovine 17α hydroxylase can be added to taxadiene 5α-hydroxylase. In certain embodiments, the peptide MALLLAVF (SEQ ID NO:51) is added to taxadiene 5α-hydroxylase. A non-limiting example of polypeptide comprising taxadiene 5α-hydroxylase fused to TCPR is At24T5αOH-tTCPR.

In some embodiments, the chimeric enzyme is able to carry out the first oxidation step with more than 10% taxadiene conversion to taxadiene-5α-ol and the byproduct 5(12)-Oxa-3(11)-cyclotaxane. For example, the percent taxadiene conversion to taxadiene-5α-ol and the byproduct 5(12)-Oxa-3(11)-cyclotaxane can be at least 20%, at least 30%, at least 40%, at least 50%, at least 60%, at least 70%, at least 80%, at least 90%, at least 95%, at least 98%, approximately 99% or approximately 100%.

Figure 9A:
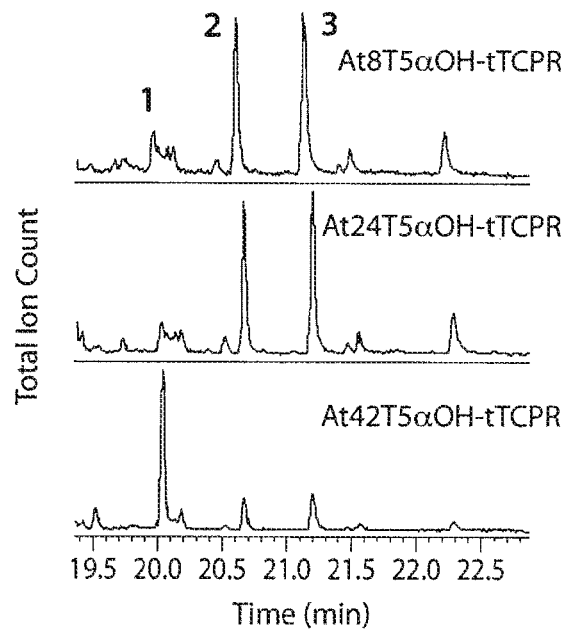
FIGS. 9A-9D. GC-MS profiles and taxadiene/taxadien-5α-ol production from artificial chimera enzyme engineered in strain 26.
Figure 9B:
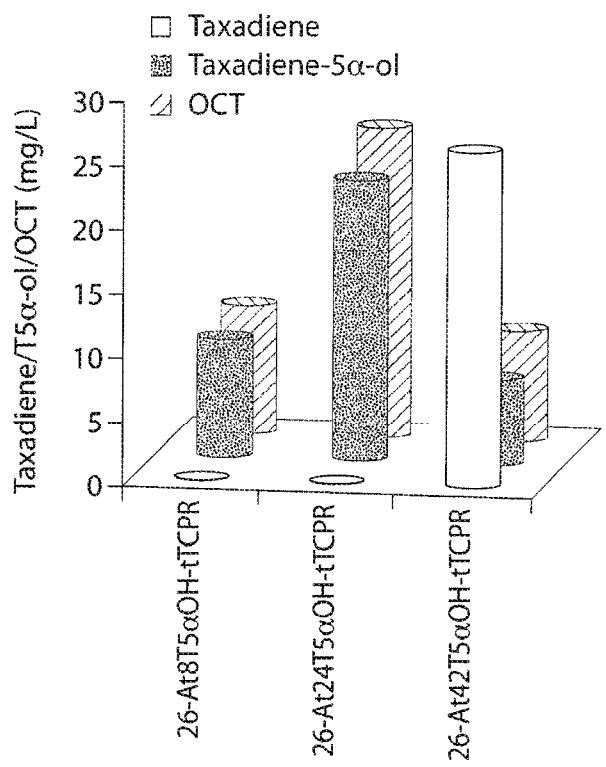
Figure 9C:
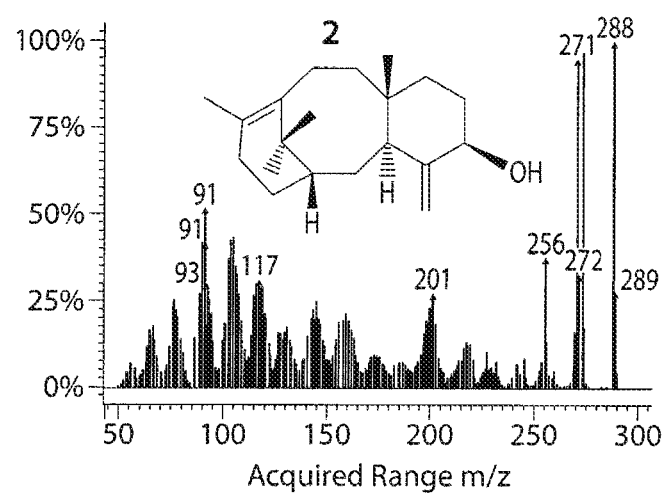
Figure 9D:
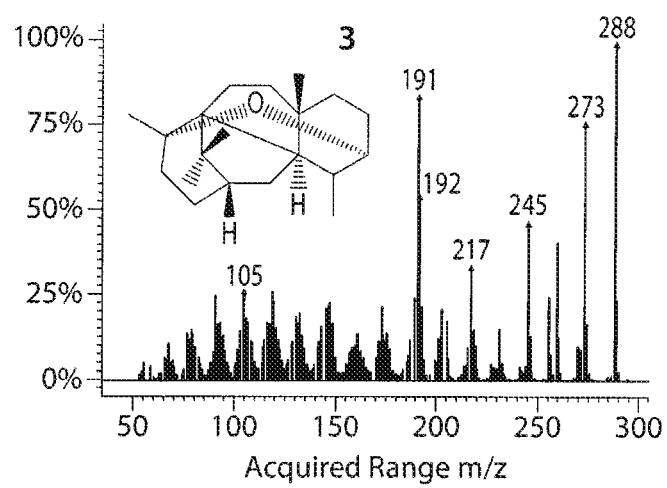
Figure 10:
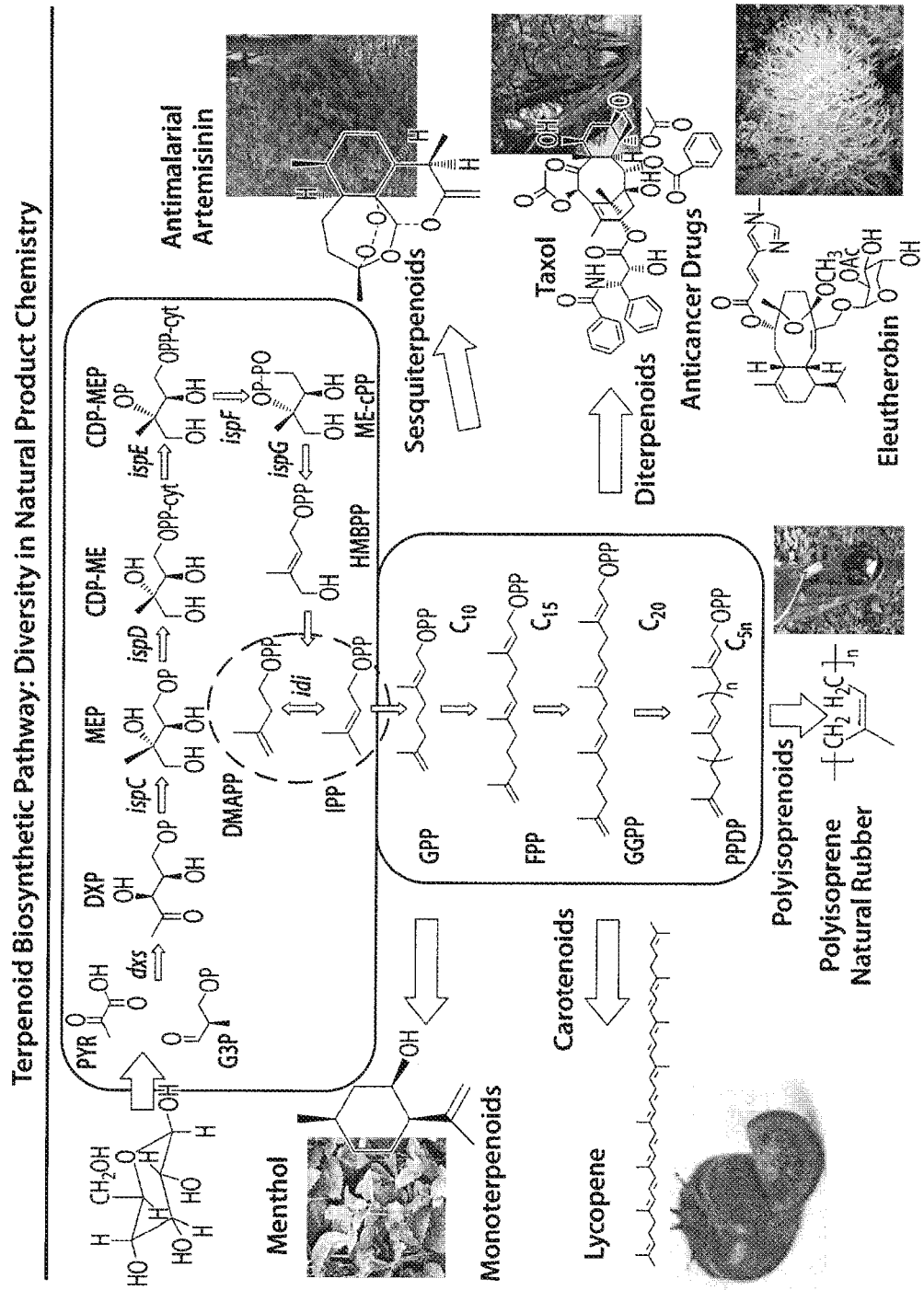
FIG. 10 presents a schematic depicting the terpenoid biosynthetic pathway and natural products produced by this pathway.
Figure 11:
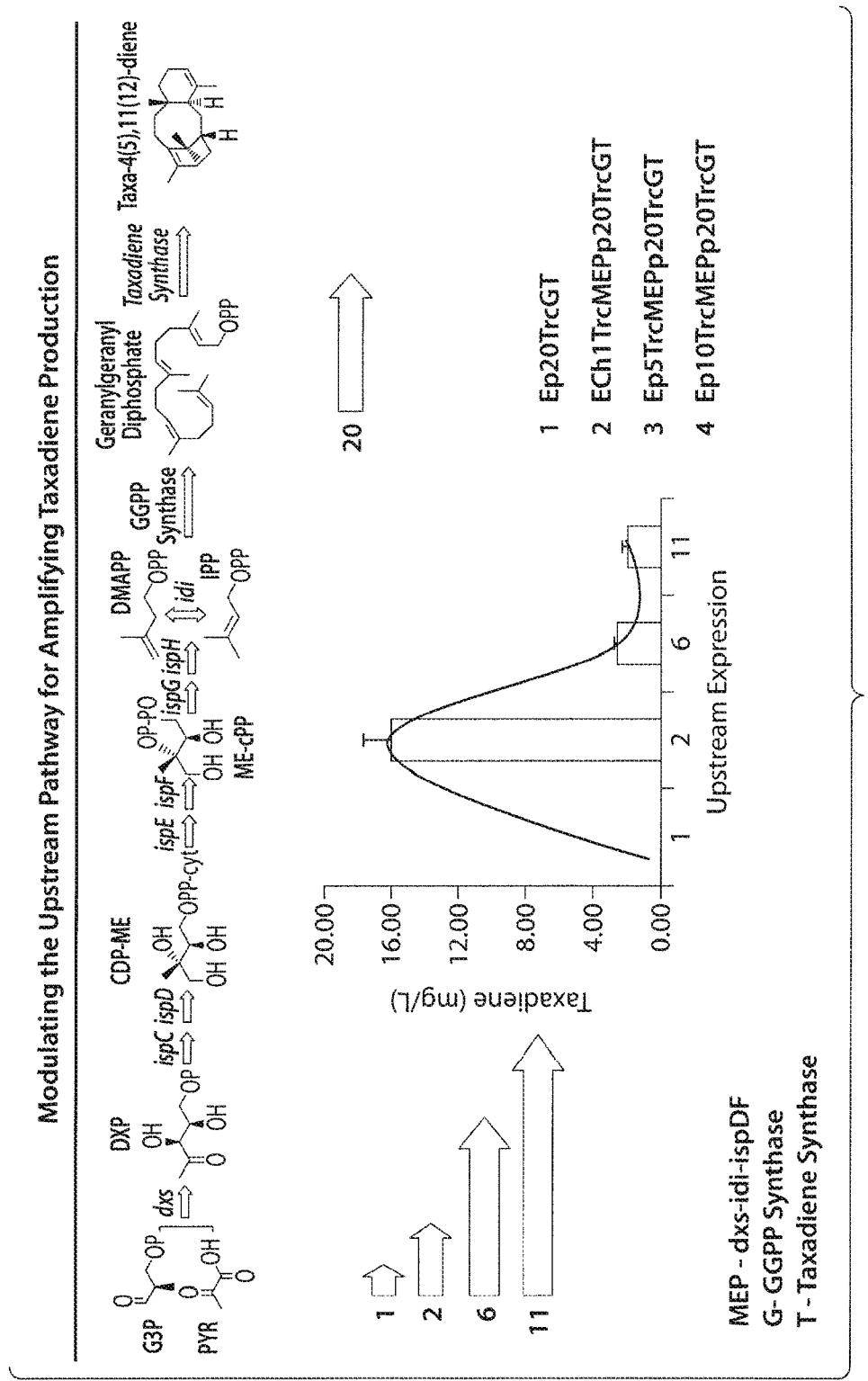
FIG. 11 presents a schematic depicting modulation of the upstream pathway for amplifying taxadiene production.
Figure 12:
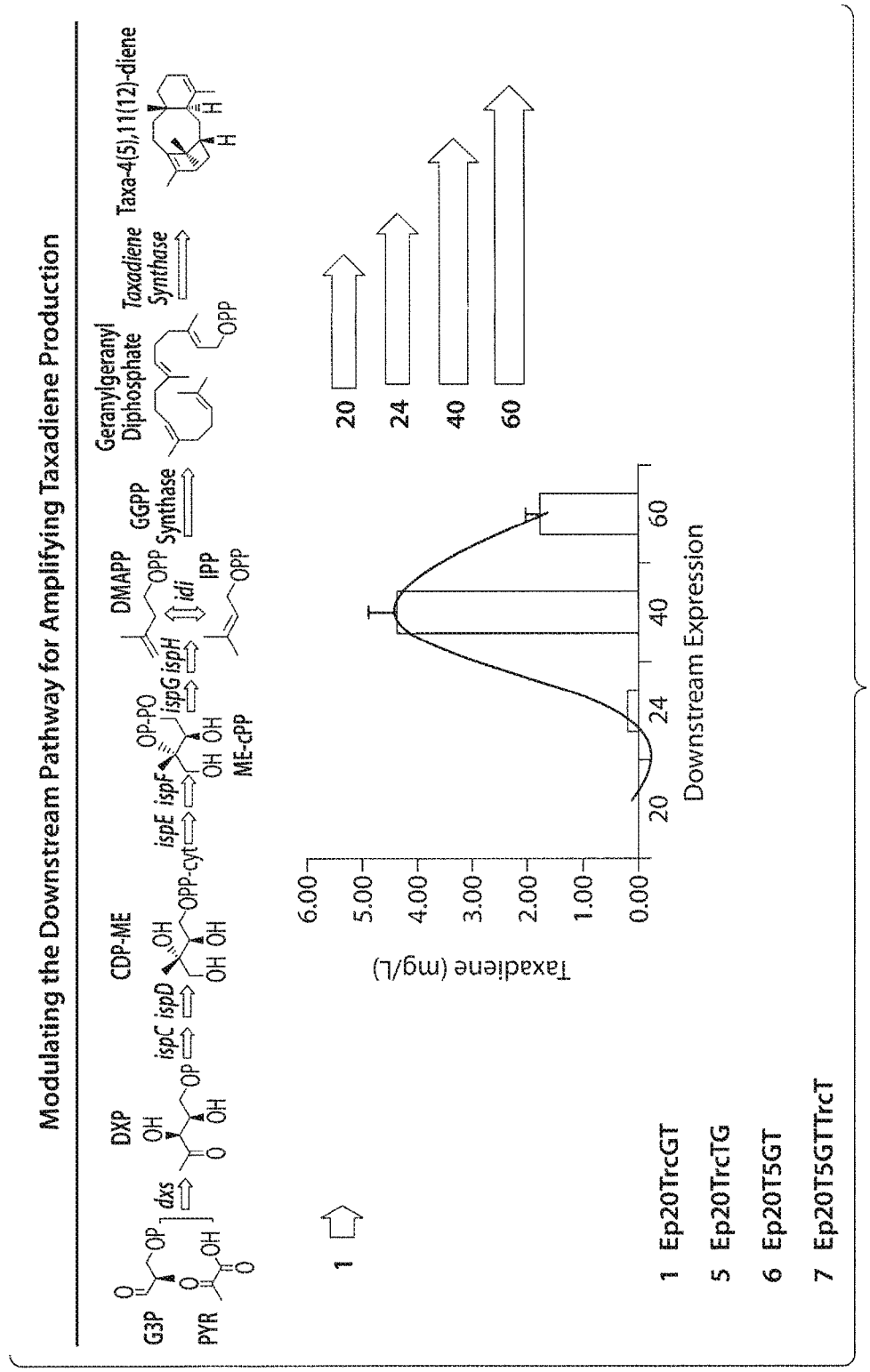
FIG. 12 presents a schematic depicting modulation of the downstream pathway for amplifying taxadiene production.
Figure 13:
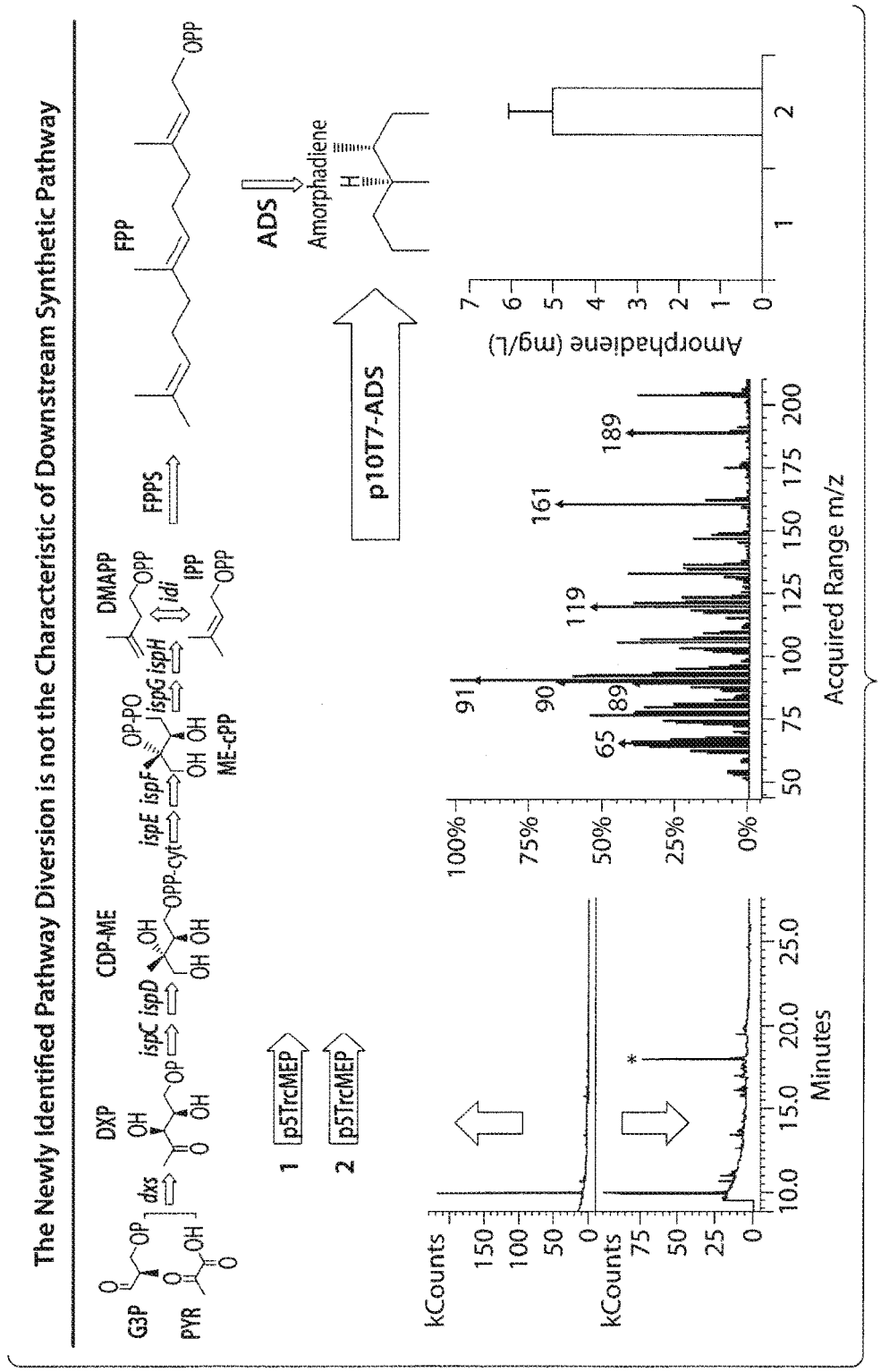
FIG. 13 presents a schematic indicating that the newly identified pathway diversion is not the characteristic of downstream synthetic pathway.

In certain embodiments, the chimeric enzyme is At245αOH-tTCPR, which was found to be capable of carrying out the first oxidation step with more than 98% taxadiene conversion to taxadiene-5α-ol and the byproduct 5(12)-Oxa-3(11)-cyclotaxane (OCT; FIG. 9a). Engineering of the step of taxadiene-5α-ol production is critical in the production of Taxol and was found to be limiting in previous efforts to construct this pathway in yeast. The engineered construct developed herein demonstrated greater than 98% conversion of taxadiene in vivo with a 2400 fold improvement over previous heterologous expression in yeast. Thus, in addition to synthesizing significantly greater amounts of key Taxol intermediates, this study also provides the basis for the synthesis of subsequent metabolites in the pathway by similar P450 chemistry.

As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

The invention also encompasses nucleic acids that encode for any of the polypeptides described herein, libraries that contain any of the nucleic acids and/or polypeptides described herein, and compositions that contain any of the nucleic acids and/or polypeptides described herein.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression.

The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production of a terpenoid, such as taxadiene, is demonstrated in the Examples section using *E. coli*. The novel method for producing terpenoids can also be expressed in other bacterial cells, fungi (including yeast cells), plant cells, etc.

A nucleic acid molecule that encodes an enzyme associated with the invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. As would be understood by one of ordinary skill in the art, routine optimization would allow for use of a variety of types of media. The selected medium can be supplemented with various additional components.

Some non-limiting examples of supplemental components include glucose, antibiotics, IPTG for gene induction, ATCC Trace Mineral Supplement, and glycolate. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of terpenoids, such as taxadiene. In some embodiments the concentration and amount of a supplemental component may be optimized. In some embodiments, how often the media is supplemented with one or more supplemental components, and the amount of time that the media is cultured before harvesting a terpenoid, such as taxadiene, is optimized.

According to aspects of the invention, high titers of a terpenoid (such as but not limited to taxadiene), are produced through the recombinant expression of genes as described herein, in a cell expressing components of the MEP pathway, and one or more downstream genes for the production of a terpenoid (or related compounds) from the products of the MEP pathway. As used herein "high titer" refers to a titer in the milligrams per liter (mg $L^{-1}$) scale. The titer produced for a given product will be influenced by multiple factors including choice of media. In some embodiments, the total titer of a terpenoid or derivative is at least 1 mg $L^{-1}$. In some embodiments, the total terpenoid or derivative titer is at least 10 mg $L^{-1}$. In some embodiments, the total terpenoid or derivative titer is at least 250 mg $L^{-1}$. For example, the total terpenoid or derivative titer can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900 or more than 900 mg $L^{-1}$ including any intermediate values. In some embodiments, the total terpenoid or derivative titer can be at least 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or more than 5.0 g $L^{-1}$ including any intermediate values.

In some embodiments, the total taxadiene 5α-ol titer is at least 1 mg $L^{-1}$. In some embodiments, the total taxadiene 5α-ol titer is at least 10 mg $L^{-1}$. In some embodiments, the total taxadiene 5α-ol titer is at least 50 mg $L^{-1}$. For example, the total taxadiene 5α-ol titer can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or more than 70 mg $L^{-1}$ including any intermediate values.

The liquid cultures used to grow cells associated with the invention can be housed in any of the culture vessels known and used in the art. In some embodiments large scale production in an aerated reaction vessel such as a stirred tank reactor can be used to produce large quantities of terpenoids, such as taxadiene, that can be recovered from the cell culture. In some embodiments, the terpenoid is recovered from the gas phase of the cell culture, for example by adding an organic layer such as dodecane to the cell culture and recovering the terpenoid from the organic layer.

Terpenoids, such as taxadiene, produced through methods described herein have widespread applications including pharmaceuticals such as paclitaxel (Taxol), artemisinin, ginkolides, eleutherobin and pseudopterosins, and many other potential pharmaceutical compounds. Further applications include compounds used in flavors and cosmetics such as geraniol, farnesol, geranlygeraniol, linalool, limonene, pinene, cineol and isoprene. Further applications include compounds for use as biofuels such as alcohols of 5, 10, and 15 carbon atom length. It is noted that the above compounds are presently produced as extracts of various plants. Plant extract-based methods are tedious, yield very small amounts and are limited as to the actual molecules that can be so obtained, namely, they do not allow the easy production of derivatives that may possess far superior properties than the original compounds.

In one aspect, the invention provides a method for making a product containing a terpenoid or terpenoid derivative. The method according to this aspect comprises increasing terpenoid production in a cell that produces one or more terpenoids by controlling the accumulation of indole in the cell or in a culture of the cells. The terpenoid, or a derivative of the terpenoid prepared through one or more chemical or enzymatic steps, is incorporated into a product to thereby make the product containing a terpenoid or terpenoid derivative. According to this aspect, the cell expressed components of the MEP pathway, and may be a bacterial cell such as *E. coli* or *B. subtilis*. In various embodiments, the accumulation of indole in the cell or in a culture of the cells is controlled at least in part by balancing an upstream non-mevalonate isoprenoid pathway with a downstream heterologous terpenoid synthesis pathway. For example, the upstream non-mevalonate isoprenoid pathway may be balanced with respect to the downstream heterologous terpenoid synthesis pathway by one or more of:

(1) increasing gene copy number for one or more upstream or downstream pathway enzymes,
(2) increasing or decreasing the expression level of the upstream and downstream pathway, as individual genes or as an operon, using promoters with different strengths,
(3) increasing or decreasing the expression level of the upstream and downstream pathways, as individual genes or as an operon, using modifications to ribosomal binding sites,
(4) replacing native genes in the MEP pathway with heterologous genes coding for homologous enzymes,
(5) codon-optimization of one or more heterologous enzymes in the upstream or downstream pathway,
(6) mutation of amino acids in one or more genes of the downstream and/or upstream pathway, or
(7) modifying the order of upstream and downstream pathway genes in a heterologous operon.

In some embodiments, the cell comprises at least one additional copy of at least one of dxs, idi, ispD, and ispF. For example, the cell may comprise a heterologous dxs-idi-ispDF operon.

According to embodiments of this aspect, indole accumulates in the culture at less than 100 mg/L, or in certain embodiments, at less than 50 mg/L, at less than 10 mg/L, or at less than 1 mg/L, or less than 0.5 mg/L, or less than 0.1 mg/L. As an alternative, or in addition to balancing the upstream and downstream pathways, the accumulation of indole in the cell or in a culture of the cells may comprise modifying or regulating the cell's indole pathway. In still other embodiments, the step of controlling the accumulation of indole in the cell or in a culture of the cells may comprise or may further comprise removing the accumulated indole from the cell culture through chemical methods, which may include using one or more absorbents or scavengers. In some embodiments, the level of indole in the culture or in the cells in monitored, or example, by continuously or intermittently measuring the amount of indole in the culture.

The invention according to this aspect can involve the manufacture of a product containing one or more terpenoids, such as one or more terpenoids selected from a hemiterpenoid, a monoterpenoid, a sesquiterpenoid, a diterpenoid, a triterpenoid or a tetraterpenoid.

In some embodiments, the product is a food product, food additive, beverage, chewing gum, candy, or oral care product. In such embodiments, the terpenoid or derivative may be a flavor enhancer or sweetener. For example, the terpenoid or derivative may include one or more of alpha-sinensal; beta-Thujone; Camphor; Carveol; Carvone; Cineole; Citral; Citronellal; Cubebol; Limonene; Menthol; Menthone; myrcene; Nootkatone; Piperitone; Sabinene hydrate; Steviol; Steviol glycosides; Thymol; Valencene; or a derivative of one or more of such compounds. In other embodiments, the terpenoid or derivative is one or more of alpha, beta and y-humulene; isopinocamphone; (−)-alpha-phellandrene; (+)-1-terpinene-4-ol; (+)-borneol; (+)-verbenone; 1,3,8-menthatriene; 3-carene; 3-Oxo-alpha-Ionone; 4-Oxo-beta-ionone; alpha-sinensal; alpha-terpinolene; alpha-thujene; Ascaridole; Camphene; Carvacrol; Cembrene; E)-4-decenal; Farnesol; Fenchone; gamma-Terpinene; Geraniol; hotrienol; Isoborneol; Limonene; myrcene; nerolidol; ocimene; p-cymene; perillaldehyde; Pulegone; Sabinene; Sabinene hydrate; tagetone; Verbenone; or a derivative of one or more of such compounds.

Downstream enzymes for the production of such terpenoids and derivatives are known.

For example, the terpenoid may be alpha-sinensal, and which may be synthesized through a pathway comprising one or more of farnesyl diphosphate synthase (e.g., AAK63847.1) and valencene synthase (e.g., AF441124_1).

In other embodiments, the terpenoid is beta-Thujone, and which may be synthesized through a pathway comprising one or more of Geranyl pyrophosphate synthase (e.g., AAN01134.1, ACA21458.2) and (+)-sabinene synthase (e.g., AF051901.1).

In other embodiments, the terpenoid is Camphor, which may be synthesized through a pathway comprising one or more of Geranyl pyrophosphate synthase (e.g., AAN01134.1, ACA21458.2), (−)-borneol dehydrogenase (e.g., GU253890.1), and bornyl pyrophosphate synthase (e.g., AF051900).

In certain embodiments, the one or more terpenoids include Carveol or Carvone, which may be synthesized through a pathway comprising one or more of Geranyl pyrophosphate synthase (e.g., AAN01134.1, ACA21458.2), 4S-limonene synthase (e.g., AAC37366.1), limonene-6-hydroxylase (e.g., AAQ18706.1, AAD44150.1), and carveol dehydrogenase (e.g., AAU20370.1, ABR15424.1).

In some embodiments, the one or more terpenoids comprise Cineole, which may be synthesized through a pathway comprising one or more of Geranyl pyrophosphate synthase (e.g., AAN01134.1, ACA21458.2) and 1,8-cineole synthase (e.g., AF051899).

In some embodiments, the one or more terpenoids includes Citral, which may be synthesized through a pathway comprising one or more of Geranyl pyrophosphate synthase (e.g., AAN01134.1, ACA21458.2), geraniol synthase (e.g., HM807399, GU136162, AY362553), and geraniol dehydrogenase (e.g., AY879284).

In still other embodiments, the one or more terpenoids includes Cubebol, which is synthesized through a pathway comprising one or more of farnesyl diphosphate synthase (e.g., AAK63847.1), and cubebol synthase (e.g., CQ813505.1).

The one or more terpenoids may include Limonene, and which may be synthesized through a pathway comprising one or more of Geranyl pyrophosphate synthase (e.g., AAN01134.1, ACA21458.2), and limonene synthase (e.g., EF426463, JN388566, HQ636425).

The one or more terpenoids may include Menthone or Menthol, which may be synthesized through a pathway comprising one or more of Geranyl pyrophosphate synthase (e.g., AAN01134.1, ACA21458.2), limonene synthase (e.g., EF426463, JN388566, HQ636425), (−)-limonene-3-hydroxylase (e.g., EF426464, AY622319), (−)-isopiperitenol dehydrogenase (e.g., EF426465), (−)-isopiperitenone reductase (e.g., EF426466), (+)-cis-isopulegone isomerase, (−)-menthone reductase (e.g., EF426467), and for Menthol (−)-menthol reductase (e.g., EF426468).

In some embodiments, the one or more terpenoids comprise myrcene, which may be synthesized through a pathway comprising one or more of Geranyl pyrophosphate synthase (e.g., AAN01134.1, ACA21458.2) and myrcene synthase (e.g., U87908, AY195608, AF271259).

The one or more terpenoids may include Nootkatone, which may be synthesized through a pathway comprising one or more of farnesyl diphosphate synthase (e.g., AAK63847.1), and Valancene synthase (e.g., CQ813508, AF441124_1).

The one or more terpenoids may include Sabinene hydrate, which may be synthesized through a pathway comprising one or more of Geranyl pyrophosphate synthase (e.g., AAN01134.1, ACA21458.2), and sabinene synthase (e.g., O81193.1).

The one or more terpenoids may include Steviol or steviol glycoside, and which may be synthesized through a pathway comprising one or more of geranylgeranylpyrophosphate synthase (e.g., AF081514), ent-copalyl diphosphate synthase (e.g., AF034545.1), ent-kaurene synthase (e.g., AF097311.1), ent-kaurene oxidase (e.g., DQ200952.1), and kaurenoic acid 13-hydroxylase (e.g., EU722415.1). For steviol glycoside, the pathway may further include UDP-glycosyltransferases (UGTs) (e.g., AF515727.1, AY345983.1, AY345982.1, AY345979.1, AAN40684.1, ACE87855.1).

The one or more terpenoids may include Thymol, which may be synthesized through a pathway comprising one or more of Geranyl pyrophosphate synthase (e.g., AAN01134.1, ACA21458.2), limonene synthase (e.g., EF426463, JN388566, HQ636425), (−)-limonene-3-hydroxylase (e.g., EF426464, AY622319), (−)-isopiperitenol dehydrogenase (e.g., EF426465), and (−)-isopiperitenone reductase (e.g., EF426466).

The one or more terpenoids may include Valencene, which may be synthesized through a pathway comprising one or more of farnesyl diphosphate synthase (e.g., AAK63847.1), and Valancene synthase (e.g., CQ813508, AF441124_1).

In some embodiments, the one or more terpenoids includes one or more of alpha, beta and γ-humulene, which may be synthesized through a pathway comprising one or more of farnesyl diphosphate synthase (e.g., AAK63847.1), and humulene synthase (e.g., U92267.1).

In some embodiments, the one or more terpenoids includes (+)-borneol, which may be synthesized through a pathway comprising one or more of Geranyl pyrophosphate synthase (e.g., AAN01134.1, ACA21458.2), and bornyl pyrophosphate synthase (e.g., AF051900).

The one or more terpenoids may comprise 3-carene, which may be synthesized through a pathway comprising one or more of Geranyl pyrophosphate synthase (e.g., AAN01134.1, ACA21458.2), and 3-carene synthase (e.g., HQ336800).

In some embodiments, the one or more terpenoids include 3-Oxo-alpha-Ionone or 4-oxo-beta-ionone, which may be synthesized through a pathway comprising carotenoid cleavage dioxygenase (e.g., ABY60886.1, BAJ05401.1).

In some embodiments, the one or more terpenoids include alpha-terpinolene, which may be synthesized through a pathway comprising one or more of Geranyl pyrophosphate synthase (e.g., AAN01134.1, ACA21458.2), and alpha-terpineol synthase (e.g., AF543529).

In some embodiments, the one or more terpenoids include alpha-thujene, which may be synthesized through a pathway comprising one or more of Geranyl pyrophosphate synthase (e.g., AAN01134.1, ACA21458.2), and alpha-thujene synthase (e.g., AEJ91555.1).

In some embodiments, the one or more terpenoids include Farnesol, which may be synthesized through a pathway comprising one or more of farnesyl diphosphate synthase (e.g., AAK63847.1), and Farnesol synthase (e.g., AF529266.1, DQ872159.1).

In some embodiments, the one or more terpenoids include Fenchone, which may be synthesized through a pathway comprising one or more of Geranyl pyrophosphate synthase (e.g., AAN01134.1, ACA21458.2), and (−)-endo-fenchol cyclase (e.g., AY693648).

In some embodiments, the one or more terpenoids include gamma-Terpinene, which may be synthesized through a pathway comprising one or more of Geranyl pyrophosphate synthase (e.g., AAN01134.1, ACA21458.2), and terpinene synthase (e.g., AB110639).

In some embodiments, the one or more terpenoids include Geraniol, which may be synthesized through a pathway comprising one or more of Geranyl pyrophosphate synthase (e.g., AAN01134.1, ACA21458.2), and geraniol synthase (e.g. HM807399, GU136162, AY362553).

In still other embodiments, the one or more terpenoids include ocimene, which may be synthesized through a pathway comprising one or more of Geranyl pyrophosphate synthase (e.g., AAN01134.1, ACA21458.2), and beta-ocimene synthase (e.g., EU194553.1).

In certain embodiments, the one or more terpenoids include Pulegone, which may be synthesized through a pathway comprising one or more of Geranyl pyrophosphate synthase (e.g., AAN01134.1, ACA21458.2), and pinene synthase (e.g., HQ636424, AF543527, U87909).

In certain embodiments, the one or more terpenoids includes Sabinene, which may be synthesized through a pathway comprising one or more of Geranyl pyrophosphate synthase (e.g., AAN01134.1, ACA21458.2), and sabinene synthase (e.g., HQ336804, AF051901, DQ785794).

In various embodiments, the product is a fragrance product, a cosmetic, a cleaning product, or a soap. In such embodiments, the terpenoid or derivative may be a fragrance. For example, the one or more terpenoid or derivative may include one or more of Linalool; alpha-Pinene; Carvone; Citronellal; Citronellol; Citral; S abinene; Limonene; Verbenone; Geraniol; Cineole; myrcene; Germacrene D; farnesene; Valencene; Nootkatone; patchouli alcohol; Farnesol; beta-Ylangene; β-Santalol; β-Santalene; a-S antalene; α-Santalol; β-vetivone; a-vetivone; khusimol; Sclarene; sclareol; beta-Damascone; beta-Damascenone; or a derivative thereof. In these or other embodiments, the one or more terpenoid or derivative compounds includes one or more of Camphene; Pulegone; Fenchone; Fenchol; Sabinene hydrate; Menthone; Piperitone; Carveol; gamma-Terpinene; beta-Thujone; dihydro-myrcene; alpha-thujene; alpha-terpineol; ocimene; nerol; nerolidol; E)-4-decenal; 3-carene; (−)-alpha-phellandrene; hotrienol; alpha-terpinolene; (+)-1-terpinene-4-ol; perillaldehyde; (+)-verbenone; isopinocamphone; tagetone; trans-myrtanal; alpha-sinensal; 1,3,8-menthatriene; (−)-cis-rose oxide; (+)-borneol; (+)-verbenone; Germacrene A; Germacrene B; Germacrene; Germacrene E; (+)-beta-cadinene; epi-cedrol; alpha, beta and y-humulene; alpha-bisabolene; beta-aryophyllene; Longifolene; alpha-sinensal; alpha-bisabolol; (−)-β-Copaene; (−)-α-Copaene; 4(Z),7(Z)-ecadienal; cedrol; cedrene; muuroladiene; isopatchoul-3-ene; isopatchoula-3,5-diene; cedrol; guaiol; (−)-6,9-guaiadiene; bulnesol; guaiol; ledene; ledol; lindestrene; alpha-bergamotene; maaliol; isovalencenol; muurolol T; beta-Ionone; alpha-Ionone; Oxo-Edulan I; Oxo-Edulan II; Theaspirone; Dihydroactinodiolide; 4-Oxoisophorone; Safranal; beta-Cyclocitral; (−)-cis-gamma-irone; (−)-cis-alpha-irone; or a derivative thereof. Such terpenoids and derivatives may be synthesized according to a pathway described above.

In some embodiments, the one or more terpenoids include Linalool, which may be synthesized through a pathway comprising one or more of Geranyl pyrophosphate synthase (e.g., AAN01134.1, ACA21458.2), and linalool synthase (e.g., FJ644544, GQ338154, FJ644548).

In some embodiments, the one or more terpenoids include alpha-Pinene, which may be synthesized through a pathway comprising one or more of Geranyl pyrophosphate synthase (e.g., AAN01134.1, ACA21458.2), and pinene synthase (e.g., HQ636424, AF543527, U87909).

In some embodiments, the one or more terpenoids includes Germacrene D, which may be synthesized through a pathway comprising one or more of farnesyl diphosphate synthase (e.g., AAK63847.1), and germacrene synthase (e.g., AAS66357.1, AAX40665.1, HQ652871).

In some embodiments, the one or more terpenoids include farnesene, which may be synthesized through a pathway comprising one or more of farnesyl diphosphate synthase (e.g., AAK63847.1), and farnesene synthase (e.g., AAT70237.1, AAS68019.1, AY182241).

In some embodiments, the one or more terpenoids comprises patchouli alcohol, which may be synthesized through a pathway comprising one or more of farnesyl diphosphate synthase (e.g., AAK63847.1), and Patchoulol synthase (e.g., AY508730.1).

In some embodiments, the one or more terpenoids comprises β-Santalol, which may be synthesized through a pathway comprising one or more of farnesyl diphosphate synthase (e.g., AAK63847.1), beta santalene synthase (e.g., HQ259029.1, HQ343278.1, HQ343277.1).

In some embodiments, the one or more terpenoids include β-Santalene, which may be synthesized through a pathway comprising one or more of farnesyl diphosphate synthase (e.g., AAK63847.1), and beta santalene synthase (e.g., HQ259029.1, HQ343278.1, HQ343277.1).

In some embodiments, the one or more terpenoids include α-Santalene or α-Santalol, which may be synthesized through a pathway comprising one or more of farnesyl diphosphate synthase (e.g., AAK63847.1), and Santalene synthase (e.g., HQ343282.1).

In other embodiments, the one or more terpenoids include sclareol, which may be synthesized through a pathway comprising one or more of geranylgeranylpyrophosphate synthase (e.g., AF081514), and sclareol synthase (e.g., HB976923.1).

In certain embodiments, the one or more terpenoids include beta-Damascone or beta-Damacenone, which may be synthesized through a pathway comprising one or more of carotenoid cleavage dioxygenase (e.g., ABY60886.1, BAJ05401.1).

In some embodiments, the one or more terpenoids include Fenchol, which may be synthesized through a pathway comprising one or more of Geranyl pyrophosphate synthase (e.g., AAN01134.1, ACA21458.2), and (−)-endo-fenchol cyclase (e.g., AY693648).

In some embodiments, the one or more terpenoids include alpha-terpineol, which may be synthesized through a pathway comprising one or more of Geranyl pyrophosphate synthase (e.g., AAN01134.1, ACA21458.2), alpha-terpineol synthase (e.g., AF543529).

In some embodiments, the one or more terpenoids include Germacrene A, which may be synthesized through a pathway comprising one or more of farnesyl diphosphate synthase (e.g., AAK63847.1), and Germacrene synthase (e.g., AEM05858.1, ABE03980.1, AAM11626.1). In other embodiments, the one or more terpenoids include Germacrene B, which may be synthesized through a pathway comprising one or more of farnesyl diphosphate synthase (e.g., AAK63847.1), and Germacrene synthase (e.g., ACF94469.1). Alternatively or in addition, the one or more terpenoids include Germacrene C, which may be synthesized through a pathway comprising one or more of farnesyl diphosphate synthase (e.g., AAK63847.1), and Germacrene synthase (e.g., AAC39432.1).

In still other embodiments, the one or more terpenoids include (+)-beta-cadinene, which may be synthesized through a pathway comprising one or more of farnesyl diphosphate synthase (e.g., AAK63847.1), cadinene synthases (e.g., U88318.1).

In some embodiments, the one or more terpenoids include epi-cedrol, which may be synthesized through a pathway comprising one or more of farnesyl diphosphate synthase (e.g., AAK63847.1), and epicedrol synthase (e.g., AF157059.1).

In other embodiments, the one or more terpenoids include alpha-bisabolene, which may be synthesized through a pathway comprising one or more of farnesyl diphosphate synthase (e.g., AAK63847.1), and bisabolene synthase (e.g., HQ343280.1, HQ343279.1).

In some embodiments, the one or more terpenoids include beta-caryophyllene, which may be synthesized through a pathway comprising one or more of farnesyl diphosphate synthase (e.g., AAK63847.1), and Caryophyllene synthase (e.g., AF472361).

The one or more terpenoids may include Longifolene, which may be synthesized through a pathway comprising one or more of farnesyl diphosphate synthase (e.g., AAK63847.1), and longifolene synthase (e.g., AY473625.1).

The one or more terpenoids may include alpha-bisabolol, which may be synthesized through a pathway comprising one or more of farnesyl diphosphate synthase (e.g., AAK63847.1), and bisabolol synthase (e.g., AD087004.1).

In some embodiments, the one or more terpenoids include (−)-β-Copaene, which may be synthesized through a pathway comprising one or more of farnesyl diphosphate synthase (e.g., AAK63847.1), and Copaene synthase (e.g., EU158098). Alternatively, or in addition, the one or more terpenoids include (−)-α-Copaene, which may be synthesized through a pathway comprising one or more of farnesyl diphosphate synthase (e.g., AAK63847.1), and Copaene synthase (e.g., AJ001539.1).

The one or more terpenoids may include cedrol or cedrene, which may be synthesized through a pathway comprising one or more of farnesyl diphosphate synthase (e.g., AAK63847.1), and cedrol synthase (e.g., AJ001539.1).

The one or more terpenoids may include muuroladiene, which may be synthesized through a pathway comprising one or more of farnesyl diphosphate synthase (e.g., AAK63847.1), and muuroladiene synthase (e.g., AJ786641.1).

The one or more terpenoids may include alpha-bergamotene, which may be synthesized through a pathway comprising one or more of farnesyl diphosphate synthase (e.g., AAK63847.1), and alpha-bergamotene synthase (e.g., HQ259029.1).

The one or more terpenoids may include alpha and/or beta-Ionone, which may be synthesized through a pathway comprising one or more of carotenoid cleavage dioxygenase (e.g., ABY60886.1, BAJ05401.1).

In some embodiments of this aspect of the invention, the product is a vitamin or nutritional supplement, and the terpenoid or derivative may be Zexanthin; β-carotene; lycopene; Astaxanthin; CoQ10; Vitamin K; Vitamin E; Labdane; Gibberellins; α-carotene; or a derivative thereof. Enzymes and encoding genes for synthesizing such terpenoids or derivatives thereof from products of the MEP pathway are known, and some are described above.

For example, the one or more terpenoids may include Zexanthin, which may be synthesized through a pathway comprising one or more of geranylgeranylpyrophosphate synthase (e.g., AF081514), phytoene synthase (e.g., AAA64982.1), phytoene desaturase (e.g., AAA21263.1, ACI04664.1), lycopene beta cyclase (e.g., AAA64980.1), and beta-carotene hydroxylase (e.g., AAA64983.1).

In other embodiments, the one or more terpenoids include α- and/or β-carotene, which may be synthesized through a pathway comprising one or more of geranylgeranylpyrophosphate synthase (e.g., AF081514), phytoene synthase (e.g., AAA64982.1, phytoene desaturase (e.g., AAA21263.1, ACI04664.1), lycopene beta cyclase (e.g., AAA64980.1,), and lycopene beta cyclase (e.g., NM_001084662.1, AAA64980.1).

In some embodiments, the one or more terpenoids include lycopene, which may be synthesized through a pathway comprising one or more of geranylgeranylpyrophosphate synthase (e.g., AF081514), phytoene synthase (e.g., AAA64982.1), phytoene desaturase (e.g., AAA21263.1, ACI04664.1), and lycopene beta cyclase (e.g., AAA64980.1).

In some embodiments, the one or more terpenoids include Astaxanthin, which may be synthesized through a pathway comprising one or more of geranylgeranylpyrophosphate synthase (e.g., AF081514), phytoene synthase (e.g., AAA64982.1), phytoene desaturase (e.g., AAA21263.1, ACI04664.1), lycopene beta cyclase (e.g., AAA64980.1), beta-carotene hydroxylase (e.g., AAA64983.1), and beta-carotene ketolase (e.g., ABL09497.1).

In still other embodiments, the one or more terpenoids include Vitamin E, which may be synthesized through a pathway comprising one or more of geranylgeranylpyrophosphate synthase (e.g., AF081514), geranylgeranylpyrophosphate reductase (e.g., BA000022), homogentisate phytyltransferase (e.g., BA000022), tocopherol-cyclase (e.g., BA000022), and copalyl pyrophosphate synthase (e.g., AAB87091).

In some embodiments of this aspect of the invention, the product is a solvent or cleaning product. For example, the terpenoid or derivative may be alpha-Pinene; beta-Pinene; Limonene; myrcene; Linalool; Geraniol; Cineole; or a derivative thereof. Some enzymes and encoding genes for synthesizing such terpenoids or derivatives thereof from products of the MEP pathway are known, and some are described above.

In some embodiments, the one or more terpenoids include beta-Pinene, which may be synthesized through a pathway comprising one or more of Geranyl pyrophosphate synthase (e.g., AAN01134.1, ACA21458.2), and pinene synthase (e.g., HQ636424, AF543527, U87909).

In some embodiments of this aspect of the invention, the product is a pharmaceutical, and the terpenoid or derivative is an active pharmaceutical ingredient. For example, the terpenoid or derivative may be Artemisinin; Taxol; Taxadiene; levopimaradiene; Gingkolides; Abietadiene; Abietic acid; beta-amyrin; Retinol; or a derivative thereof. In still other embodiments, the terpenoid or derivative is Thymoquinone; Ascaridole; beta-selinene; 5-epi-aristolochene; vetispiradiene; epi-cedrol; alpha, beta and y-humulene; a-cubebene; beta-elemene; Gossypol; Zingiberene; Periplanone B; Capsidiol; Capnellene; illudin; Isocomene; cyperene; Pseudoterosins; Crotophorbolone; Englerin; Psiguadial; Stemodinone; Maritimol; Cyclopamine; Veratramine; Aplyviolene; macfarlandin E; Betulinic acid; Oleanolic acid; Ursoloic acid; Pimaradiene; neo-abietadiene; Squalene; Dolichol; Lupeol; Euphol; Kaurene; Gibberellins; Cassaic acid; Erythroxydiol; Trisporic acid; Podocarpic acid; Retene; Dehydroleucodine; Phorbol; Cafestol; kahweol; Tetrahydrocannabinol; androstenol; or a derivative thereof. Enzymes and encoding genes for synthesizing such terpenoids or derivatives thereof from products of the MEP pathway are known, and some are described above.

For example, in some embodiments, the one or more terpenoids include Artemisinin, which may be synthesized through a pathway comprising one or more of farnesyl diphosphate synthase (e.g., AAK63847.1), Amorphadiene Synthase (e.g., AAF98444.1), amorpha-4,11-diene monooxygenase (e.g., DQ315671), and artemisinic aldehyde delta-11(13) reductase (e.g., ACH61780.1).

In other embodiments, the one or more terpenoids include Taxadiene, which may be synthesized through a pathway comprising one or more of geranylgeranylpyrophosphate synthase (e.g., AF081514), and taxadiene synthase (e.g., U48796.1, AF081514). In some embodiments, the terpenoid or derivative is Taxol, which may be synthesized through a pathway comprising one or more of geranylgeranylpyrophosphate synthase (e.g., AF081514), taxadiene synthase (e.g., U48796.1, AF081514), *Taxus cuspidata* taxadiene 5-alpha hydroxylase (e.g., AY289209.2), *Taxus cuspidata* 5-alpha-taxadieno1-10-beta-hydroxylase (e.g., AF318211.1), *Taxus cuspidata* taxoid 10-beta hydroxylase (e.g., AY563635.1), *Taxus cuspidata* taxane 13-alpha-hydroxylase (e.g., AY056019.1), *Taxus cuspidata* taxane 14b-hydroxylase (e.g., AY188177.1), *Taxus cuspidata* taxoid 7-beta-hydroxylase (e.g., AY307951.1).

In still other embodiments, the one or more terpenoids or derivatives include levopimaradiene, which may be synthesized through a pathway comprising one or more of geranylgeranylpyrophosphate synthase (e.g., AF081514), and levopimaradiene synthase (e.g., AAS89668.1).

In some embodiments, the one or more terpenoids include Gingkolides, which may be synthesized through a pathway comprising one or more of geranylgeranylpyrophosphate synthase (e.g., AF081514), and levopimaradiene synthase (e.g., AAS89668.1).

In some embodiments, the one or more terpenoids or derivatives may include Abietadiene or Abietic acid, which may be synthesized through a pathway comprising one or more of geranylgeranylpyrophosphate synthase (e.g., AF081514), and abietadiene synthase (e.g., AAK83563.1).

The one or more terpenoids or derivatives may include beta-amyrin, which may be synthesized through a pathway comprising one or more of geranylgeranylpyrophosphate synthase (e.g., AF081514), and beta-Amyrin Synthase (e.g., ACO24697.1).

The one or more terpenoids or derivatives may include beta-selinene, which may be synthesized through a pathway comprising one or more of farnesyl diphosphate synthase (e.g., AAK63847.1), and selinene synthase (e.g., O64404.1).

In still other embodiments, the one or more terpenoids or derivatives include 5-epi-aristolochene, which may be synthesized through a pathway comprising one or more of farnesyl diphosphate synthase (e.g., AAK63847.1), and 5-epi-aristolochene synthase (e.g., AF542544.1).

In some embodiments, the one or more terpenoids or derivatives include vetispiradiene, which may be synthesized through a pathway comprising one or more of farnesyl diphosphate synthase (e.g., AAK63847.1), and vetispiradiene synthases (e.g., BD227667).

In some embodiments, the one or more terpenoids or derivatives include epi-cedrol, which may be synthesized through a pathway comprising one or more of farnesyl diphosphate synthase (e.g., AAK63847.1), and epicedrol synthase (e.g., AF157059.1).

The one or more terpenoids or derivatives may include beta-elemene, which may be synthesized through a pathway comprising one or more of farnesyl diphosphate synthase (e.g., AAK63847.1), and elemene synthase (e.g., DQ872158.1).

In still other embodiments, the terpenoid or derivative is Gossypol, which may be synthesized through a pathway comprising one or more of farnesyl diphosphate synthase (e.g., AAK63847.1), and (+) delta cadinene synthase (e.g., U88318.1).

In some embodiments, the terpenoid or derivative is Zingiberene, which may be synthesized through a pathway comprising one or more of farnesyl diphosphate synthase (e.g., AAK63847.1), and Zingiberene synthase (e.g., Q5SBP4.1).

In still other embodiments, the one or more terpenoids or derivatives include Capsidiol, which may be synthesized through a pathway comprising one or more of farnesyl diphosphate synthase (e.g., AAK63847.1), and epi-aristolochene synthase (e.g., Q40577.3).

The one or more terpenoids or derivatives may include Pimaradiene, which may be synthesized through a pathway comprising one or more of geranylgeranylpyrophosphate synthase (e.g., AF081514), ent-pimara-8(14),15-diene synthase (e.g., Q6Z5J6.1), and syn-pimara-7,15-diene synthase (e.g., AAU05906.1).

The one or more terpenoids or derivatives may include neo-abietadiene, which may be synthesized through a pathway comprising one or more of geranylgeranylpyrophosphate synthase (e.g., AF081514), and levopimaradiene synthase (e.g., AAS89668.1).

The one or more terpenoids or derivatives may include Squalene, which may be synthesized through a pathway comprising one or more of farnesyl diphosphate synthase (e.g., AAK63847.1), and squalene synthase (e.g., AEE86403.1).

The one or more terpenoids or derivatives may include Lupeol, which may be synthesized through a pathway comprising one or more of geranylgeranylpyrophosphate synthase (e.g., AF081514), and lupeol synthase (e.g., AAD05032.1).

The one or more terpenoids or derivatives may include Kaurene, which may be synthesized through a pathway comprising one or more of geranylgeranylpyrophosphate synthase (e.g., AF081514), ent-copalyl diphosphate synthase (e.g., AF034545.1), and ent-kaurene synthase (e.g., AF097311.1).

In some embodiments of this aspect of the invention, the product is a food preservative. In such embodiments, the terpenoid or derivative may be Carvacrol; Carvone; or a derivative thereof. For example, the Carvone may be synthesized through a pathway comprising one or more of Geranyl pyrophosphate synthase (e.g., AAN01134.1, ACA21458.2), 4S-limonene synthase (e.g., AAC37366.1), limonene-6-hydroxylase (e.g., AAQ18706.1, AAD44150.1), and carveol dehydrogenase (e.g., AAU20370.1, ABR15424.1).

In some embodiments of this aspect, the product is a lubricant or surfactant. The terpenoid or derivative may be, for example, one or more of alpha-Pinene; beta-Pinene; Limonene; myrcene; farnesene; Squalene; or a derivative thereof. Enzymes and encoding genes for synthesizing such terpenoids or derivatives thereof from products of the MEP pathway are known, and some are described above.

The one or more terpenoids may include farnesene, which may be synthesized through a pathway comprising one or more of farnesyl diphosphate synthase (e.g., AAK63847.1), and farnesene synthase (e.g., AAT70237.1, AAS68019.1, AY182241).

The one or more terpenoids may include Squalene, which may be synthesized through a pathway comprising one or more of farnesyl diphosphate synthase (e.g., AAK63847.1), and squalene synthase (e.g., AEE86403.1).

In some embodiments, the terpenoid or derivative is polymerized, and the resulting polymer may be elastomeric. In some such embodiments, the terpenoid or derivative may be alpha-Pinene; beta-Pinene; Limonene; myrcene; farnesene; Squalene; isoprene; or a derivative thereof. Enzymes and encoding genes for synthesizing such terpenoids or derivatives thereof from products of the MEP pathway are known, and some are described above. In some embodiments, the one or more terpenoids include isoprene, which may be synthesized through a pathway comprising one or more of Isoprene synthase (e.g., HQ684728.1).

In some embodiments of this aspect of the invention, the product is an insecticide, pesticide or pest control agent, and the terpenoid or derivative is an active ingredient. For example, the one or more terpenoid or derivative may include one or more Carvone; Citronellol; Citral; Cineole; Germacrene C; (+)-beta-cadinene; or a derivative thereof. In other embodiments, the one or more terpenoid or derivative is Thymol; Limonene; Geraniol; Isoborneol; beta-Thujone; myrcene; (+)-verbenone; dimethyl-nonatriene; Germacrene A; Germacrene B; Germacrene D; patchouli alcohol; Guaiazulene; muuroladiene; cedrol; alpha-cadinol; d-occidol; Azadirachtin A; Kaurene; or a derivative thereof. Enzymes and encoding genes for synthesizing such terpenoids or derivatives thereof from products of the MEP pathway are known, and some are described above.

For example, the one or more terpenoids may include Germacrene D, which may be synthesized through a pathway comprising one or more of farnesyl diphosphate synthase (e.g., AAK63847.1), and Germacrene synthase (e.g., AAS66357.1, AAX40665.1, HQ652871).

In some embodiments, the product is a cosmetic or personal care product, and the terpenoid or derivative is not a fragrance. For example, one or more terpenoid or derivative is Camphor; Linalool; Carvone; myrcene; farnesene; patchouli alcohol; alpha-bisabolene; alpha-bisabolol; beta-Ylangene; β-Santalol; β-Santalene; a-Santalene; α-Santalol; or aderivative thereof. In some embodiments, the terpenoid or derivative is Camphene; Carvacrol; alpha-terpineol; (Z)-beta-ocimene; nerol; (E)-4-decenal; perillaldehyde; (−)-cis-rose oxide; Copaene; 4(Z),7(Z)-decadienal; isopatchoulenone; (−)-6,9-guaiadiene; Retinol; betulin; (−)-cis-gamma-irone; (−)-cis-alpha-irone; Phytoene; Phytofluene; or a derivative thereof. In some embodiments, the one or more terpenoids may include alpha-bisabolene, which may be synthesized through a pathway comprising one or more of farnesyl diphosphate synthase (e.g., AAK63847.1), and bisabolene synthase (HQ343280.1, HQ343279.1).

In some embodiments, the one or more terpenoids or derivatives include (Z)-beta-ocimene, which may be synthesized through a pathway comprising one or more of Geranyl pyrophosphate synthase (e.g., AAN01134.1, ACA21458.2), and beta-ocimene synthase (e.g., NM_117775).

In some embodiments, the one or more terpenoids or derivatives include Copaene, which may be synthesized through a pathway comprising one or more of farnesyl diphosphate synthase (e.g., AAK63847.1), and Copaene synthase (e.g., EU158098).

In other embodiments, the terpenoid or derivative is (−)-cis-gamma-irone or (−)-cis-alpha-irone, which may be synthesized through a pathway comprising one or more of carotenoid cleavage dioxygenase (e.g., ABY60886.1, BAJ05401.1).

In still other embodiments, the one or more terpenoids include Phytoene or Phytofluene, which may be synthesized through a pathway comprising one or more of geranylgeranylpyrophosphate synthase (e.g., AF081514), phytoene synthase (e.g., AAA64982.1, and phytoene desaturase (e.g., AAA21263.1, ACI04664.1).

EXAMPLES

Methods

Strains, Plasmids, Oligonucleotides and Genes

E. coli K12 MG1655 strain was used as the host strain of all the taxadiene strain construction. E. coli K12MG1655 Δ(recA,endA) and E. coli K12MG1655Δ(recA,endA)ED3 strains were provided by Professor Kristala Prather's lab at MIT (Cambridge, Mass.). Detail of all the plasmids constructed for the study is shown in Table 2. All oligonucleotides used in this study are contained in Table 3.

The sequences of geranylgeranyl pyrophosphate synthase (GGPPS),[50] Taxadiene synthase (TS),[51] Cytochrome P450 Taxadiene 5α-hydroxylase (T5αOH) and Taxus NADPH:cytochrome P450 reductase (TCPR)[46] were obtained from Taxus canadensis, Taxus brevifolia, Taxus cuspidate (Genbank accession codes: AF081514, U48796, AY289209 and AY571340). Genes were custom-synthesized using the plasmids and protocols reported by Kodumal et al.[52] (Supplementary details Appendix 1) to incorporate E. coli translation codon and removal of restriction sites for cloning purposes. Nucleotides corresponding to the 98 and 60 N-terminal amino acids of GGPPS and TS (plastid transit peptide) were removed and the translation insertion sequence Met was inserted.[17]

Construction of MEP Pathway (dxs-idi-idpDF operon).

dxs-idi-ispDF operon was initially constructed by cloning each of the genes from the genome of E. coli K12 MG1655 using the primers dxs(s), dxs(a), idi(s), idi(a), ispDF(s) and ispDFI(a) under pET21C+ plasmid with T7 promoter (p20T7MEP).[53] Using the primers dxsidiispDFNcoI (s) and dxsidiispDFKpnI(a) dxs-idi-ispDF operon was sub-cloned into and pTrcHis2B (Invitrogen) plasmid after digested with NcoI and KpnI for pTrcMEP plasmid (p20TrcMEP). p20TrcMEP plasmid digested with MluI and PmeI and cloned into MluI and PmeI digested pACYC184-melA (P2A) plasmid to construct p10TrcMEP plasmid. pTrcMEP plasmid digested with BstZ17I and ScaI and cloned into PvuII digested pCL1920 plasmid to construct p5TrcMEP plasmid. For constructing p20T5MEP plasmid initially the dxs-idi-ispDF operon was cloned into pQE plasmid with T5 promoter (pQE-MEP) using the primers dxsidiispD-FNcoI (s) and dxsidiispDFXhoI(a). A fraction of the operon DNA with T5 promoter was amplified using the primers T5AgeI(s) and T5NheI(a) from pQEMEP plasmid. The DNA fragment was digested with AgeI/NheI and cloned into the p20T7MEP plasmid digested with SGrAI/NheI enzymes.

Construction of Taxadiene Pathway (GT and TG operons).

The downstream taxadiene pathways (GT and TG operon) were constructed by cloning PCR fragments of GGPPS and TS into the NocI-EcoRI and EcoRI-SalI sites of pTrcHIS2B plasmid to create p20TrcGT and p20TrcTG using the primers GGPPSNcoI(s), GGPPSEcoRI(a), TSEcoRI(s), TS salI (a), TSNcoI(s) TSEcoRI(a) GGPPSEcoRI(s) and GGPPSSalI(a). For constructing p20T5GT, initially the operon was amplified with primers GGPPSNcoI(s) and TSXhoI(a) and cloned into a pQE plasmid under T5 promoter digested with NcoI/XhoI. Further the sequence was digested with XbaI and XhoI and cloned into the pTrc plasmid backbone amplified using the primers pTrcSaI(s) and pTrcXba(a). p10T7TG was constructed by subcloning the NcoI/SalI digested TG operon from p20TrcTG into NcoI/SalI digested pACYC-DUET1 plasmid. p5T7TG was constructed by cloning the BspEI/XbaI digested fragment to the XbaI/BspEI digested DNA amplified from pCL1920 plasmid using pCLBspEI(s) and pCLXbaI(a) primers.

Construction of Chromosomal Integration MEP Pathway Plasmids

For constructing the plasmids with FRP-Km-FRP cassette for amplifying the sequence for integration, p20T7MEP and p20T5MEP was digested with XhoI/ScaI. FRP-Km-FRP cassette was amplified from the Km cassette with FRP sequence from pkD13 plasmid using the primers KmFRPXhoI(s) and KmFRPScaI(a). The amplified DNA was digested with XhoI/ScaI and cloned into the XhoI/ScaI digested p20T7MEP and p20T5MEP plasmid (p20T7MEPKmFRP and p20T5MEPKmFRP). Similarly the p20TrcMEP plasmid was digested with SacI/ScaI and the amplified DNA using the primers KmFRPSacI(s) and KmFRPScaI(a) was digested, cloned into the p20TrcMEP plasmid (p20TrcMEPKm-FRP).

Chromosomal Integration of the MEP Pathway Cassette (LacIq-MEP-FRP-Km-FRP) Cassette The MEP pathways constructed under the promoters T7, T5 and Trc were localized to the ara operon region in the chromosome with the Kan marker. The PCR fragments were amplified from p20T7MEPKmFRP, p20T5MEPKmFRP and p20TrcMEPKm-FRP using the primers IntT7T5(s), IntTrc(s) and Int(a) and then electroporated into E. coli MG1655 recA-end- and E. coli MG1655 recA-end-EDE3 cells for chromosomal integration through the λ Red recombination technique.[54] The site specific localization was confirmed and the Km marker was removed through the action of the FLP recombinase after successful gene integration.

Construction of Taxadiene 5α-ol Pathway

The transmembrane region (TM) of the taxadiene 5α-ol hydroxylase (T5αOH) and Taxus Cytochrome P450 reductase (TCPR) was identified using PredictProtein software (www.predictprotein.org).[55] For transmembrane engineering selective truncation at 8, 24 and 42 amino acid residues on the N-terminal transmembrane region of taxadiene 5α-ol hydroxylase (T5αOH) and 74 amino acid region in the TCPR was performed. The removal of the 8, 24 and 42 residue N-terminal amino acids of taxadiene 5α-ol hydroxylase (T5αOH), incorporation of one amino acid substituted bovine 17a hydroxylase N-terminal 8 residue peptide MALLLAVF (SEQ ID NO:51) to the N-terminal truncated T5αOH sequences[44] and GSTGS peptide linker was carried out using the primer CYP17At8AANdeI(s), CYP17At24AANdeI(s), CYP17At42AANdeI(s) and CYPLinkBamHI(a). Using these primers each modified DNA was amplified, NdeI/BamHI digested and cloned into NdeI/BamHI digested pACYC DUET1 plasmid to construct p10At8T5αOH, p10At24T5αOH and p10At42T5αOH plasmids. 74 amino acid truncated TCPR (tTCPR) sequence was amplified using primers CPRBamHI(s) and CPRSalI(a). The amplified tTCPR sequence and the plasmids, p10At8T5αOH, p10At24T5αOH and p10At42T5αOH, was digested with BamHI/SalI and cloned to construct the plasmids p10At8T5αOH-tTCPR, p10At24T5αOH-tTCPR and p10At42T5αOH-tTCPR.

Culture Growth for Screening the Taxadiene and Taxadiene-5α-ol Analysis

Single transformants of pre-engineered *E. coli* strains harboring the appropriate plasmid with upstream (MEP), downstream taxadiene pathway and taxadiene 5α-ol were cultivated for 18 h at 30° C. in Luria-Bertani (LB) medium (supplemented with appropriate antibiotics, 100 mg/mL carbenecilin, 34 mg/mL chloramphenicol, 25 mg/L kanamycin or 50 mg/L spectinomycin). For small scale cultures to screen the engineered strains, these preinnoculum were used to seed fresh 2-mL rich media (5 g/L yeast extract, 10 g/L Trypton, 15 g/L, glucose, 10 g/L NaCl, 100 mM HEPS, 3 mL/L Antifoam B, pH 7.6, 100 ug/mL Carbenicillin and 34 ug/mL chloramphenicol), at a starting $A_{600}$ of 0.1. The culture was maintained with appropriate antibiotics and 100 mM IPTG for gene induction at 22° C. for 5 days.

Bioreactor Experiments for the Taxadiene 5α-ol Producing Strain.

The Bioflo bioreactor (New Brunswick) was assembled as to manufacturer's instructions. One liter of rich media with 1% glycerol (v/v) was inoculated with 50 mL of 8h culture ($A_{600}$ of ~2.2) of the strain 26-At24T5αOH-tTCPR grown in LB medium containing the antibiotics (100 mg/mL carbenicillin, 34 mg/mL chloramphenicol) at the same concentrations. 1 L-bioreactors with biphasic liquid-liquid fermentation using 20% v/v dodecane. Oxygen was supplied as filtered air at 0.5 v/v/m and agitation was adjusted to maintain dissolved oxygen levels above 50%. pH of the culture was controlled at 7.0 using 10% NaOH. The temperature of the culture in the fermentor was controlled at 30° C. until the cells were grown into an optical density of approximately 0.8, as measured at a wavelength of 600 nm (OD600). The temperature of the fermentor was reduced to 22° C. and the cells were induced with 0.1 mM IPTG. Dodecane was added aseptically to 20% (v/v) of the media volume. During the course of the fermentation the concentration of glycerol and acetate accumulation was monitored with constant time intervals. During the fermentation as the glycerol concentration depleted below 0.5 g/L, glycerol (3 g/L) was introduced into the bioreactor.

The fermentation was further optimized using a fed batch cultivation with a defined feed medium containing 0.5% yeast extract and 20% (v/v) dodecane (13.3 g/L $KH_2PO_4$, 4 g/L $(NH_4)_2HPO_4$, 1.7 g/L citric acid, 0.0084 g/L EDTA, 0.0025 g/L $CoCl_2$, 0.015 g/L $MnCl_2$, 0.0015 g/L $CuCl_2$, 0.003 g/L $H_3BO_3$, 0.0025 g/L $Na_2MoO_4$, 0.008 g/L $Zn(CH_3COO)_2$, 0.06 g/L Fe(III) citrate, 0.0045 g/L thiamine, 1.3 g/L $MgSO_4$, 10 g/L glycerol, 5 g/L yeast extract, pH 7.0). The same medium composition was used for the fermentation of strains 17 and 26 with appropriate antibiotics (strain 17: 100 µg/mL carbenicillin and 50 µg/mL spectinomycin; strain 26: 50 µg/mL spectinomycin).

For the taxadien-5α-ol producing strain, one liter of complex medium with 1% glycerol (v/v) was inoculated with 50 mL of an 8h culture (OD of ~2.2) of strain 26-At24T5αOH-tTCPR grown in LB medium containing 50 µg/mL spectinomycin and 34 µg/mL chloramphenicol). Oxygen was supplied as filtered air at 0.5 (vvm) and agitation was adjusted to maintain dissolved oxygen levels above 30%. The pH of the culture was controlled at 7.0 using 10% NaOH. The temperature of the culture in the fermentor was controlled at 30° C. until the cells were grown into an optical density of approximately 0.8, as measured at a wavelength of 600 nm (OD600). The temperature of the fermentor was reduced to 22° C. and the pathway was induced with 0.1 mM IPTG. Dodecane was added aseptically to 20% (v/v) of the media volume. During the course of the fermentation, the concentration of glycerol and acetate accumulation was monitored with constant time intervals. During the fermentation as the glycerol concentration depleted 0.5-1 g/L, 3 g/L of glycerol was introduced into the bioreactor.

GC-MS Analysis of Taxadiene and Taxadiene-5α-ol

For analysis of taxadiene accumulation from small scale culture, 1.5 mL of the culture was vortexed with 1 mL hexane for 30 min. The mixture was centrifuged to separate the organic layer. For bioreactor 1 uL of the dodecane layer was diluted to 200 uL using hexane. 1 uL of the hexane layer was analyzed by GC-MS (Varian saturn 3800 GC attached to a Varian 2000 MS). The sample was injected into a HP5ms column (30m×250 uM×0.25 uM thickness) (Agilent Technologies USA). Helium (ultra purity) at a flow rate 1.0 ml/min was used as a carrier gas. The oven temperature was first kept constant at 50° C. for 1 min, and then increased to 220° C. at the increment of 10° C./min, and finally held at this temperature for 10 min. The injector and transfer line temperatures were set at 200° C. and 250° C., respectively.

Standard compounds from biological or synthetic sources for taxadiene and taxadiene 5α-ol was not commercially available. Thus we performed fermentations of taxadiene producing *E. coli* in a 2 L bioreactor to extract pure material. Taxadiene was extracted by solvent extraction using hexane, followed by multiple rounds of silica column chromatography to obtain the pure material for constructing a standard curve for GC-MS analysis. We have compared the GC and MS profile of the pure taxadiene with the reported literature to confirm the authenticity of the compound[60]. In order to check the purity we have performed 1HNMR of taxadiene. Since the accumulation of taxadiene-5α-ol was very low level we used taxadiene as a measure to quantify the production of this molecule and authentic mass spectral fragmentation characteristics from previous reports[42].

qPCR Measurements for Transcriptional Analysis of Engineered Strains

Transcriptional gene expression levels of each gene were detected by qPCR on mRNA isolated from the appropriate strains. To prevent degradation, RNA was stabilized before cell lysis using RNAprotect bacterial reagent (Qiagen). Subsequently, total RNA was isolated using RNeasy mini kit (Qiagen) combined with nuclease based removal of genomic DNA contaminants. cDNA was amplified using iScript cDNA synthesis kit (Biorad). qPCR was carried out on a Bio-Rad iCycler using the iQ SYBR Green Supermix (Biorad). The level of expression of rrsA gene, which is not subject to variable expression, was used for normalization of qPCR values.[56] Table 3 has primers used for qPCR. For each primer pair, a standard curve was constructed with mRNA of *E. coli* as the template.

Figure 1B:
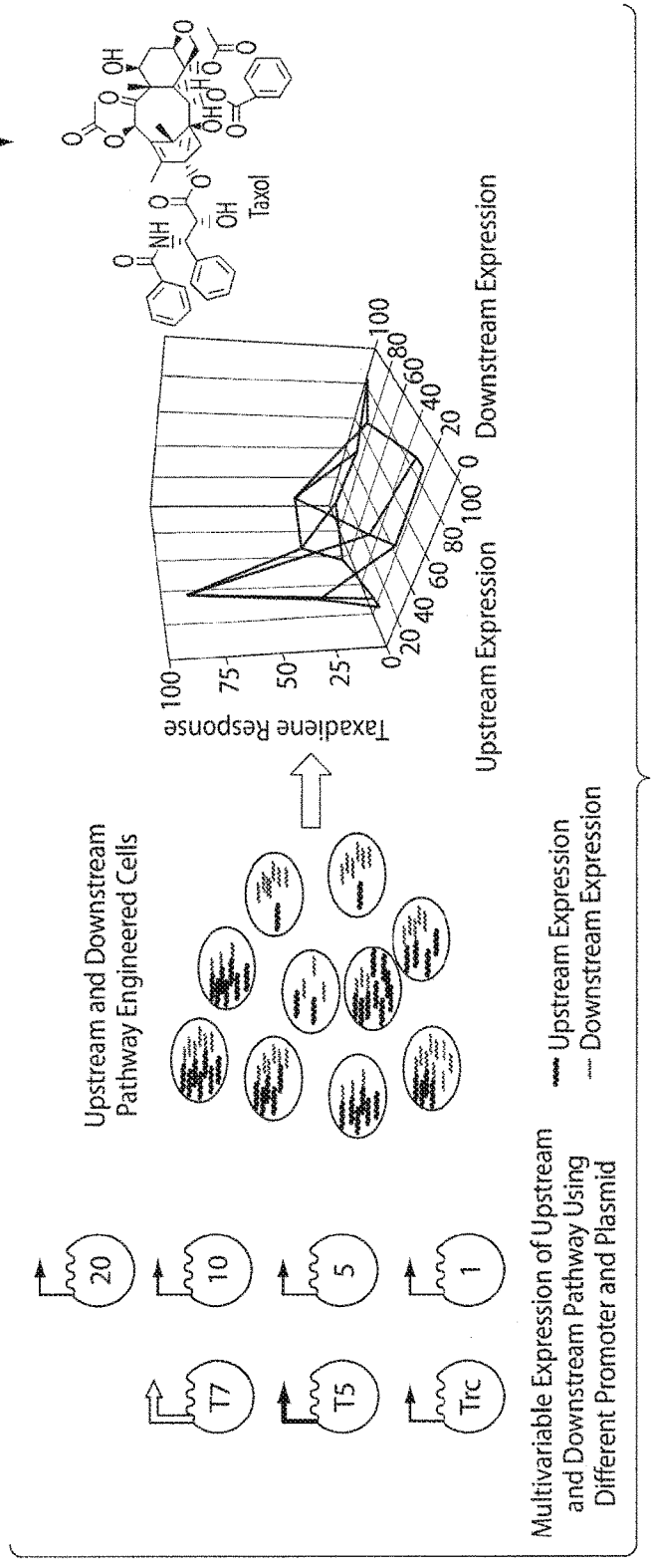
Figure 2A:
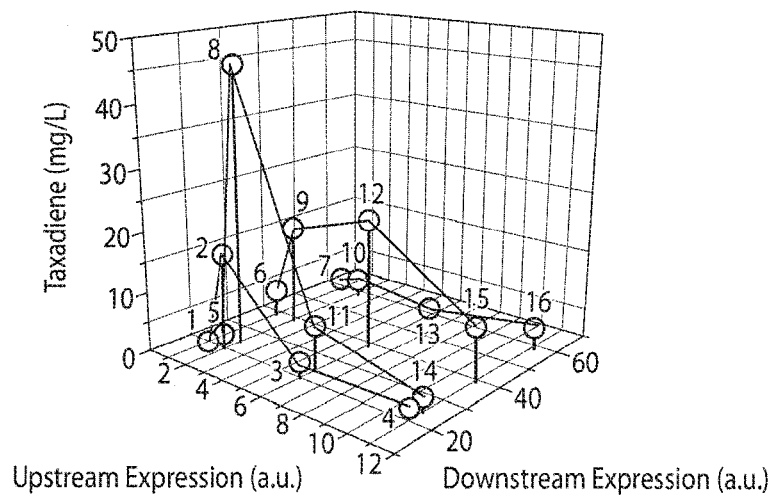
Figure 2B:
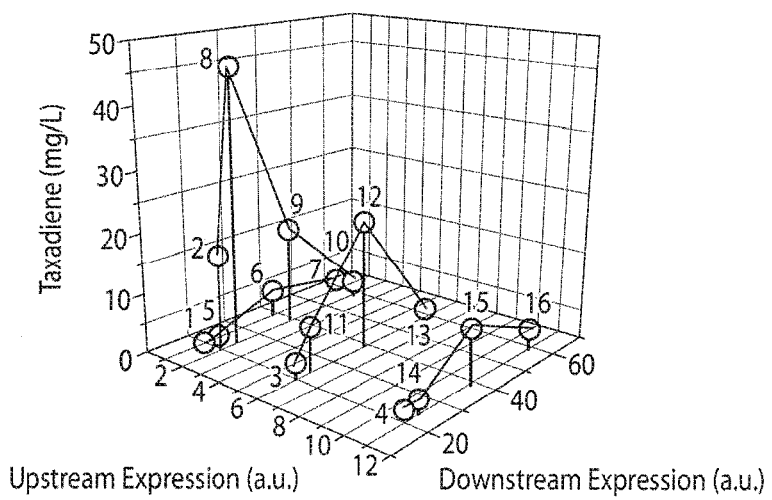
Figure 2C:
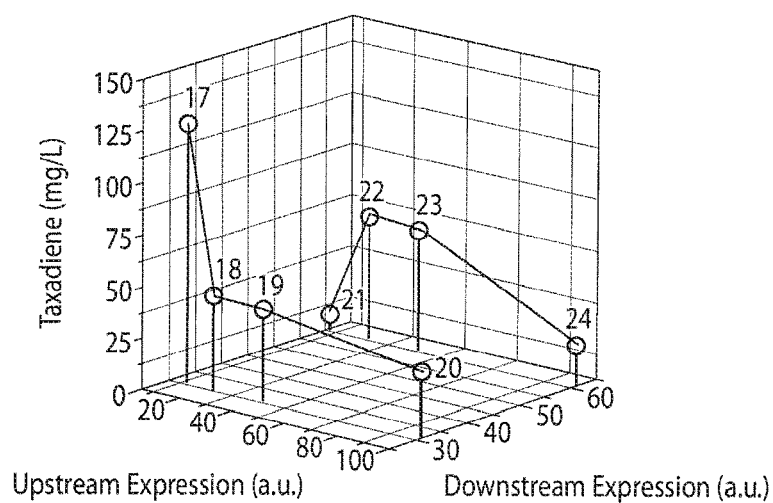
Figure 2D:
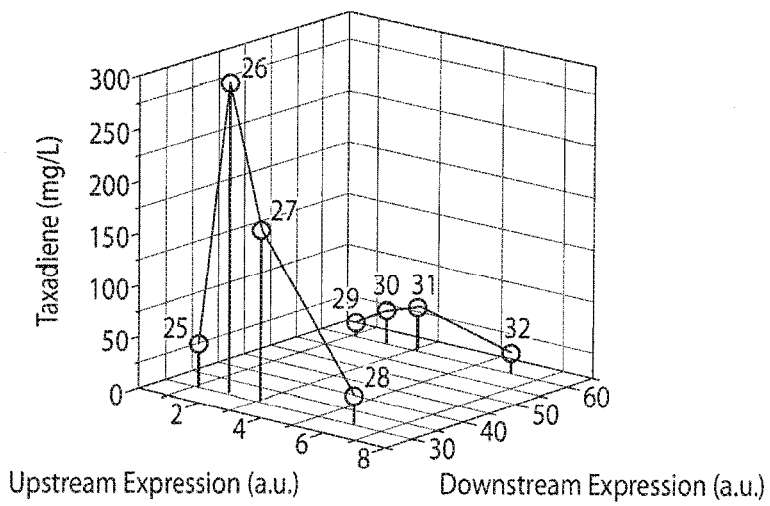

Example 1: Taxadiene Accumulation Exhibits Strong Non-Linear Dependence on the Relative Strengths of the Upstream MEP and Downstream Synthetic Taxadiene Pathways FIG. 1B depicts the various ways by which promoters and gene copy numbers were combined to modulate the relative flux (or strength) through the upstream and downstream pathways of taxadiene synthesis. A total of 16 strains were constructed in order to de-bottleneck the MEP pathway, as well as optimally balance it with the downstream taxadiene pathway. FIGS. 2A, 2B summarize the results of taxadiene accumulation in each of these strains, with FIG. 2A accentuating the dependence of taxadiene accumulation on the upstream pathway for constant values of the downstream pathway, and FIG. 2B the dependence on the downstream pathway for constant upstream pathway strength (see also Table 1 for the calculation of the upstream and downstream pathway expression from the reported promoter strengths and plasmid copy numbers[33-36]). Clearly, there are maxima exhibited with respect to both upstream and downstream pathway expression. For constant downstream pathway expression (FIG. 2A), as the upstream pathway expression increases from very low levels, taxadiene production is increased initially due to increased supply of precursors to the overall pathway. However, after an intermediate value, further upstream pathway increases cannot be accommodated by the capacity of the downstream pathway. This pathway imbalance leads to the accumulation of an intermediate (see below) that may be either inhibitory to cells or simply indicate flux diversion to a competing pathway, ultimately resulting in taxadiene accumulation reduction.

For constant upstream pathway expression (FIG. 2B), a maximum is similarly observed with respect to the level of downstream pathway expression. This is attributed to an initial limitation of taxadiene production by low expression levels of the downstream pathway, which is thus rate limiting with respect to taxadiene production. At high levels of downstream pathway expression we are likely seeing the negative effect of high copy number on cell physiology, hence, a maximum exists with respect to downstream pathway expression. These results demonstrate that dramatic changes in taxadiene accumulation can be obtained from changes within a narrow window of expression levels for the upstream and downstream pathways. For example, a strain containing an additional copy of the upstream pathway on its chromosome under Trc promoter control (Strain 8, FIG. 2A) produced 2000 fold more taxadiene than one overexpressing only the synthetic downstream pathway (Strain 1, FIG. 2A). Furthermore, changing the order of the genes in the downstream synthetic operon from GT (GPPS-TS) to TG (TS-GPPS) resulted in 2-3-fold increase (strains 1-4 compared to 5, 8, 11 and 14). The observed results show that the key to taxadiene overproduction is ample downstream pathway capacity and careful balancing between the upstream precursor pathway with the downstream synthetic taxadiene pathway. Altogether, the engineered strains established that the MEP pathway flux can be substantial, if a wide range of expression levels for the endogenous upstream and synthetic downstream pathway are searched simultaneously.

Example 2: Chromosomal Integration and Fine Tuning of the Upstream and Downstream Pathways Further Enhances Taxadiene Production To provide ample downstream pathway strength while minimizing the plasmid-borne metabolic burden[37], two new sets of 4 strains each were engineered (strains 25-28 and 29-32) in which the downstream pathway was placed under the control of a strong promoter (T7) while keeping a relatively low number of 5 and 10 copies, respectively. It can be seen (FIG. 2C) that, while the taxadiene maximum is maintained at high downstream strength (strains 21-24), a monotonic response is obtained at the low downstream pathway strength (strains 17-20, FIG. 2C). This observation prompted the construction of two additional sets of 4 strains each that maintained the same level of downstream pathway strength as before but expressed very low levels of the upstream pathway (strains 25-28 and 29-32, FIG. 2D). Additionally, the operon of the upstream pathway of the latter strain set was chromosomally integrated. It can be seen that not only is the taxadiene maximum recovered, albeit at very low upstream pathway levels, but a much greater taxadiene maximum is attained (300 mg/L). We believe this significant increase can be attributed to a decrease in cell's metabolic burden. This was achieved by 1) eliminating plasmid dependence through integration of the pathway into the chromosome and 2) attaining a fine balance between the upstream and downstream pathway expression.

Figure 7:
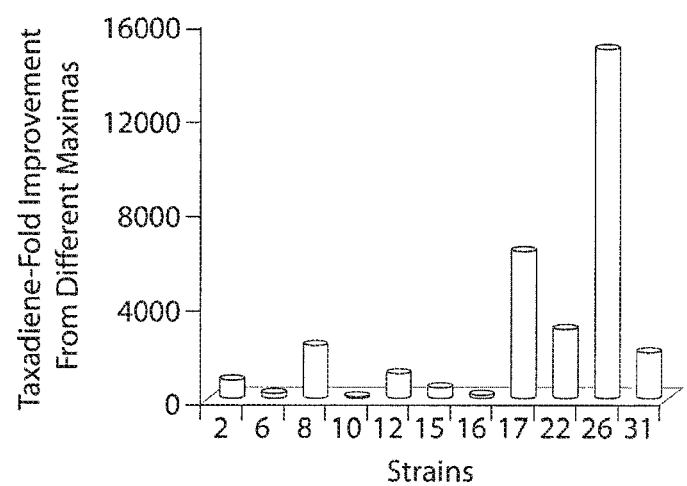
FIG. 7. Fold improvements in taxadiene production from the modular pathway expression search. Taxadiene response in fold improvements from all the observed maximas from FIGS. 2A, B and C compared to strain 1. The 2.5 fold differences between two highest maximas (strain 17 and 26) and 23 fold (strain 26 and 10) with lowest one indicates that missing an optimal response results in significantly lower titers.

The 32 recombinant constructs allowed us to adequately probe the modular pathway expression space and amplify ~15000 fold improvement in taxadiene production. This is by far the highest production of terpenoids from *E. coli* MEP isoprenoid pathway reported (FIG. 3A). Additionally, the observed fold improvements in terpenoid production are significantly higher than those of reported combinatorial metabolic engineering approaches that searched an extensive genetic space comprising up to a billion combinatorial variants of the isoprenoid pathway.[30] This suggests that pathway optimization depends far more on fine balancing of the expression of pathway modules than multi-source combinatorial gene optimization. The multiple maxima exhibited in the phenotypic landscape of FIG. 1 underscores the importance of probing the expression space at sufficient resolution to identify the region of optimum overall pathway performance. FIG. 7 depicts the fold improvements in taxadiene production from the modular pathway expression search.

Figure 8A:
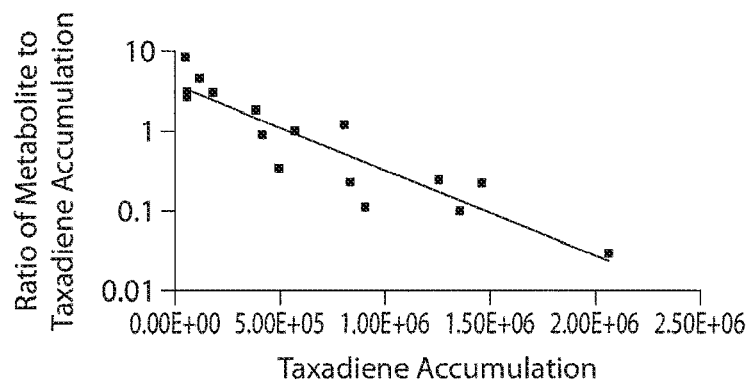
FIGS. 8A-8C. Metabolite FIG. 8A demonstrates between taxadiene to metabolite accumulation. The metabolite accumulation from the engineered strain is anti-proportionally related to the taxadiene production in an exponential manner. The correlation coefficient for this relation was determined to 0.92
Figure 8B:
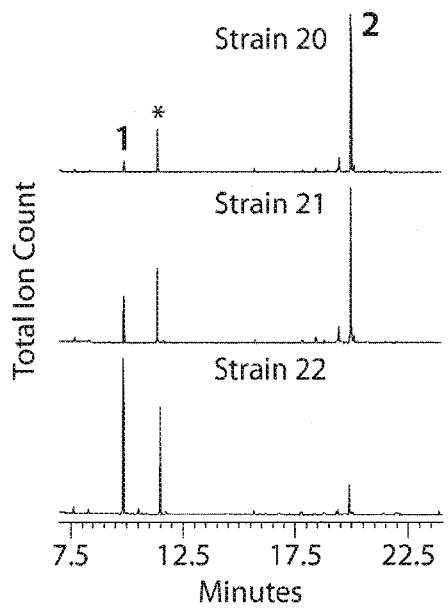
Figure 8C:
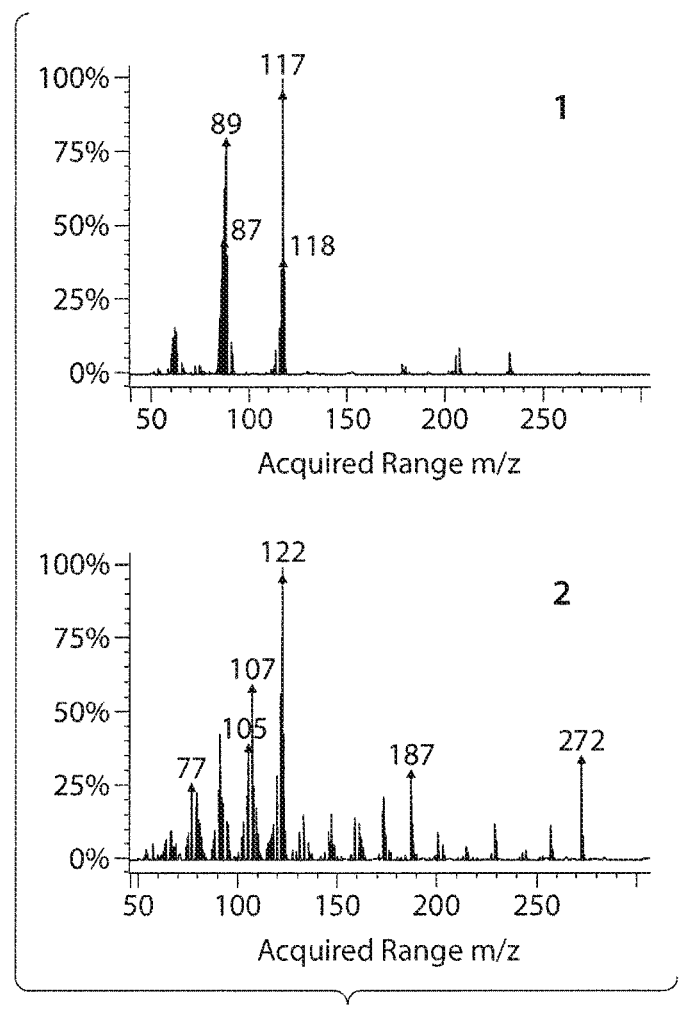

Example 3: Metabolite Inversely Correlates with Taxadiene Production and Identification of Metabolite Metabolomic analysis of the previous engineered strains identified an, as yet, unknown, metabolite byproduct that correlated strongly with pathway expression levels and taxadiene production (FIG. 3 and FIG. 8). Although the chemical identity of the metabolite was unknown, we hypothesized that it is an isoprenoid side-product, resulting from pathway diversion and has been anti-correlated as a direct variable to the taxadiene production (FIG. 3 and FIG. 8) from the engineered strains. A critical attribute of our optimal strains is the fine balancing that alleviates the accumulation of this metabolite, resulting in higher taxadiene production. This balancing can be modulated at different levels from chromosome, or different copy number plasmids, using different promoters, with significantly different taxadiene accumulation.

Figure 15B:
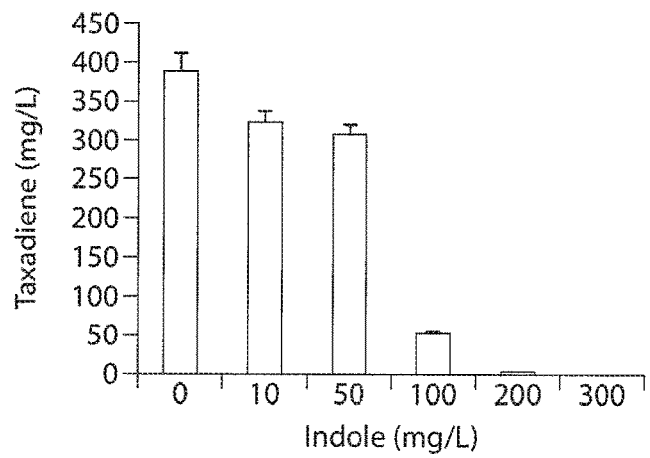
Figure 15C:
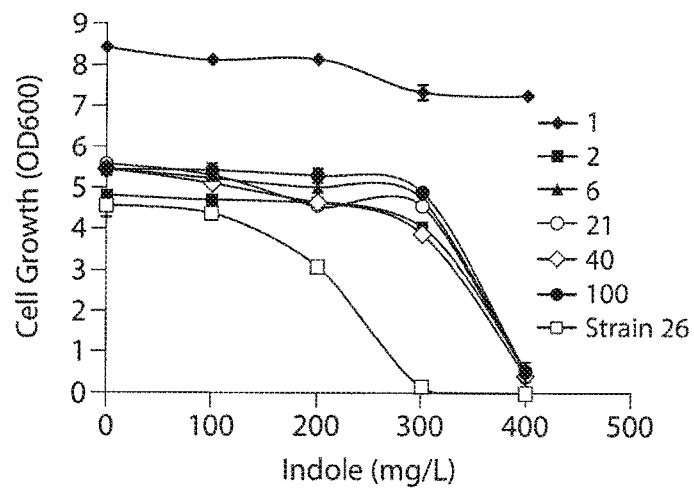
Figure 16A:
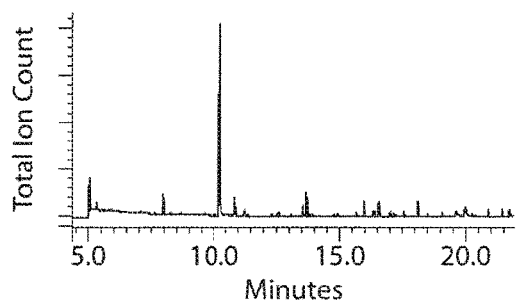
FIGS. 16A-16G. Unknown metabolite identified as indole.
Figure 16B:
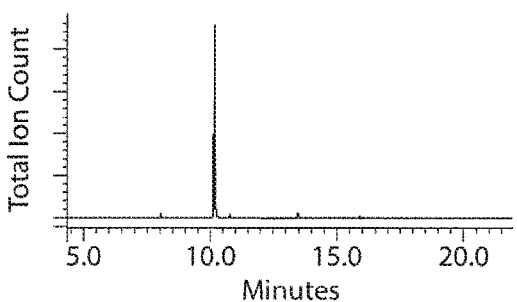
Figure 16C:
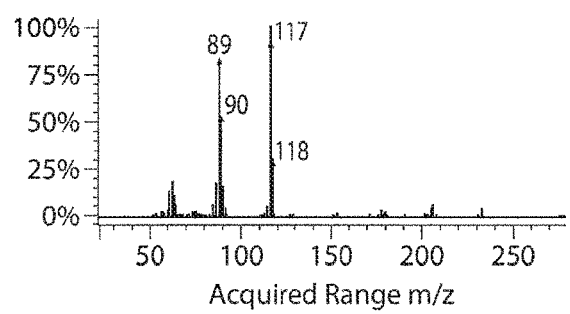
Figure 16D:
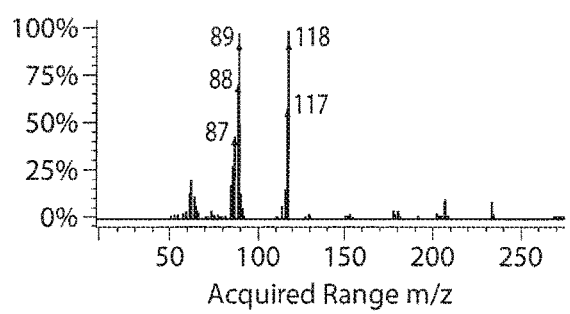
Figure 16E:
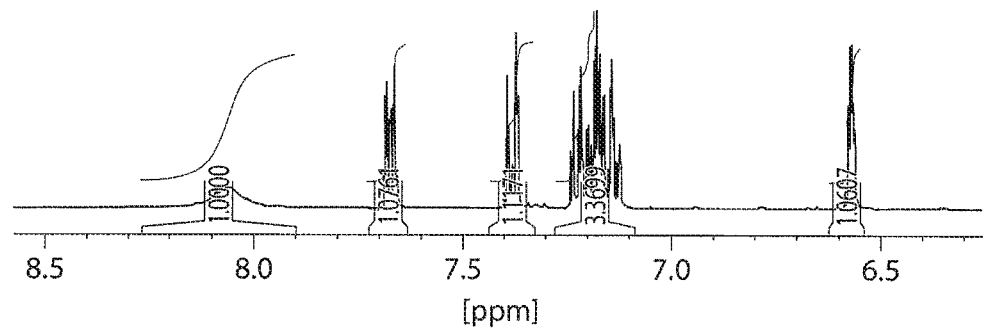
Figure 16F:
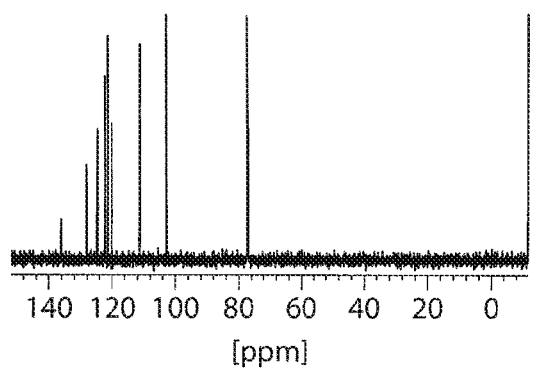
Figure 16G:
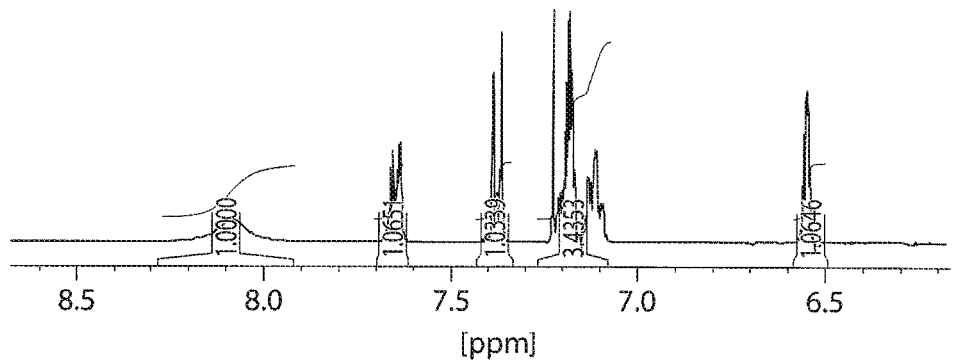

Subsequently the corresponding peak in the gas chromatography-mass spectrometry (GC-MS) chromatogram was identified as indole by GC-MS, $^1$H and $^{13}$C nuclear magnetic resonance (NMR) spectroscopy studies (FIG. 16). We found that taxadiene synthesis by strain 26 is severely inhibited by exogenous indole at indole levels higher than ~100 mg/L (FIG. 15B). Further increasing the indole concentration also inhibited cell growth, with the level of inhibition being very strain dependent (FIG. 15C). Although the biochemical mechanism of indole interaction with the isoprenoid pathway is presently unclear, the results in FIG. 15 suggest a possible synergistic effect between indole and terpenoid compounds of the isoprenoid pathway in inhibiting cell growth. Without knowing the specific mechanism, it appears strain 26 has mitigated the indole's effect, which we carried forward for further study.

Example 4: Cultivation of Engineered Strains

In order to explore the taxadiene producing potential under controlled conditions for the engineered strains, fed batch cultivations of the three highest taxadiene accumulating strains (~60 mg/L from strain 22; ~125 mg/L from strain 17; ~300 mg/L from strain 26) were carried out in 1 L-bioreactors (FIG. 17). The fed batch cultivation studies were carried out as liquid-liquid two-phase fermentation using a 20% (v/v) dodecane overlay. The organic solvent was introduced to prevent air stripping of secreted taxadiene from the fermentation medium, as indicated by preliminary findings. In defined media with controlled glycerol feeding, taxadiene productivity increased to 174±5 mg/L (SD), 210±7 mg/L (SD), and 1020±80 mg/L (SD), respectively for strains 22, 17 and 26 (FIG. 17A). Additionally, taxadiene production significantly affected the growth phenotype, acetate accumulation and glycerol consumption (FIG. 17B-17D).

Figure 17A:
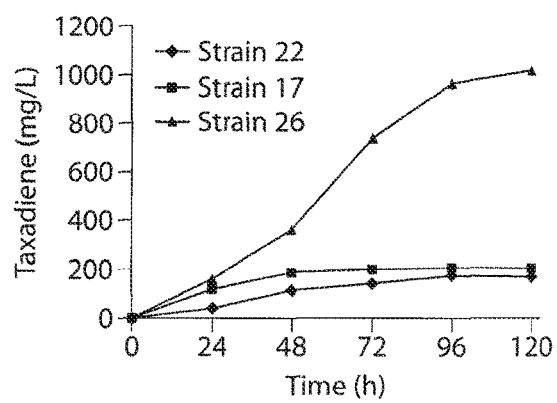
FIGS. 17A-17D. Fed batch cultivation of engineered strains in 1 L-bioreactor.
Figure 17B:
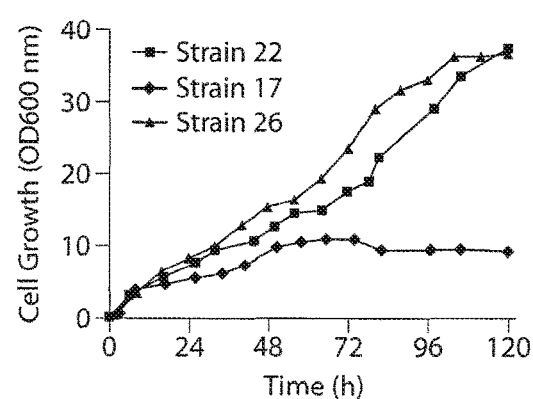
Figure 17C:
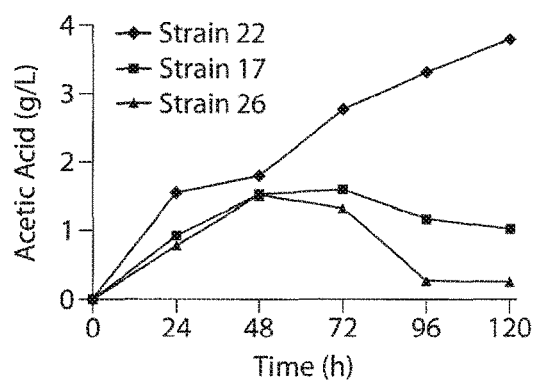
Figure 17D:
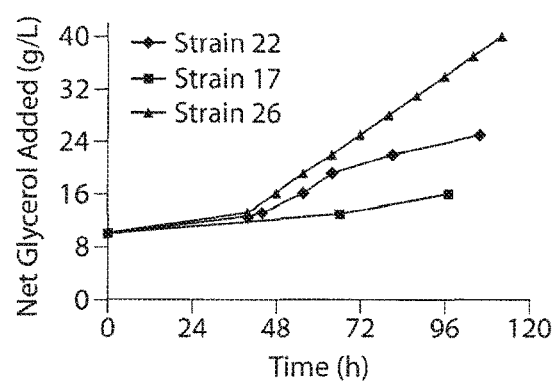

FIG. 17C shows that acetate accumulates in all strains initially, however after ~60 hrs acetate decreases in strains 17 and 26 while it continues to increase in strain 22. This phenomenon highlights the differences in central carbon metabolism between high MEP flux strains (26 and 17) and low MEP flux strain (22). Additionally, this observation is another illustration of the good physiology that characterizes a well-balanced,-functioning strain. Acetic acid, as product of overflow metabolism, is initially produced by all strains due to the high initial glycerol concentrations used in these fermentations and corresponding high glycerol pathway flux. This flux is sufficient for supplying also the MEP pathway, as well as the other metabolic pathways in the cell. At ~48 hrs, the initial glycerol is depleted, and the cultivation switches to a fed-batch mode, during which low but constant glycerol levels are maintained. This results in a low overall glycerol flux, which, for strains with high MEP flux (strains 26 and 17), is mostly diverted to the MEP pathway while minimizing overflow metabolism. As a result acetic acid production is reduced or even totally eliminated. Regarding the decline in acetic acid concentration, it is possible that acetic acid assimilation may have happened to some extent, although this was not further investigated from a flux analysis standpoint. Some evaporation and dilution due to glycerol feed are further contributing to the observed acetic acid concentration decline. In contrast, for strains with low MEP flux (strain 22), flux diversion to the MEP pathway is not very significant, so that glycerol flux still supplies all the necessary carbon and energy requirements. Overflow metabolism continues to occur leading to acetate secretion.

Clearly the high productivity and more robust growth of strain 26 allowed very high taxadiene accumulation. Further improvements should be possible through optimizing conditions in the bioreactor, balancing nutrients in the growth medium, and optimizing carbon delivery.

Figure 4A:
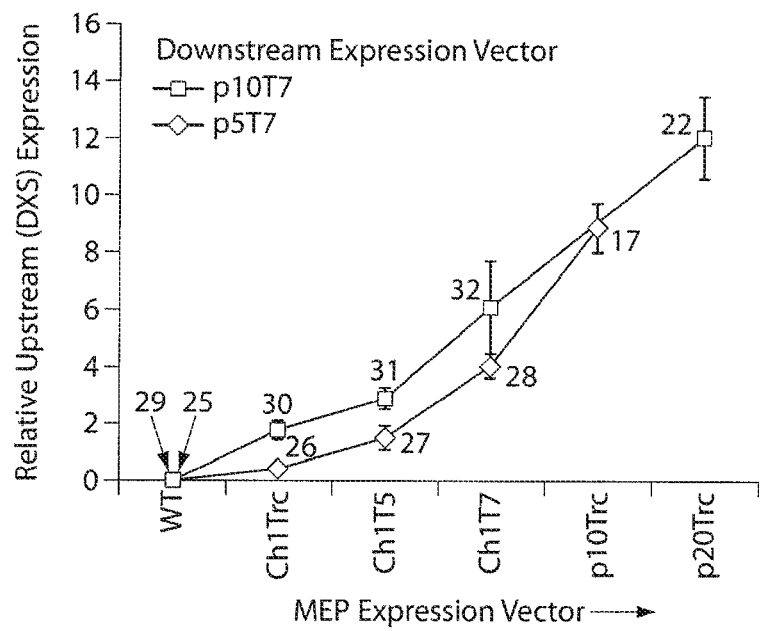
FIGS. 4A-4D. Upstream and downstream pathway transcriptional gene expression levels and changes in cell physiology of engineered strains. Relative expression of the first genes in the operon of upstream (DXS) and downstream (TS) pathway is quantified by qPCR. Similar expression profiles were observed with the genes in the downstream of the operons. The corresponding strain numbers are shown in the graph.
Figure 4B:
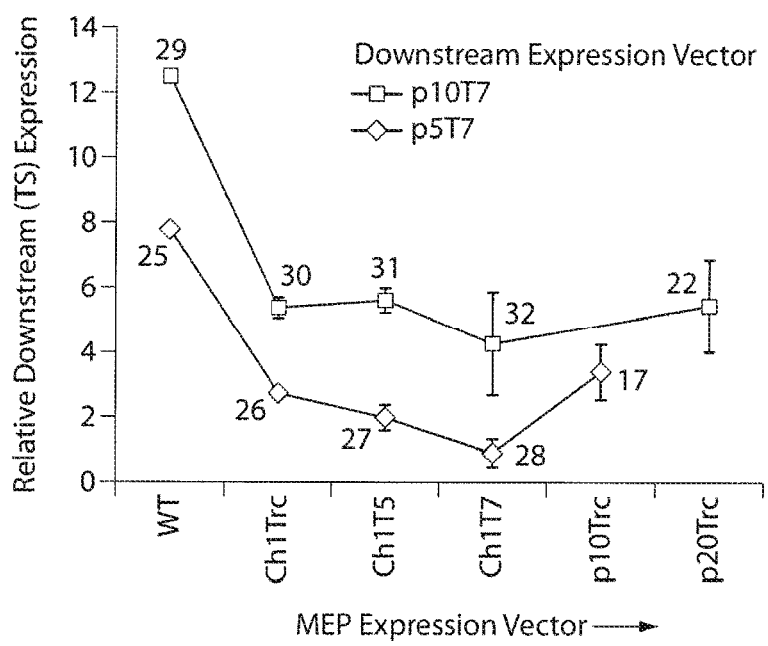
Figure 14A:
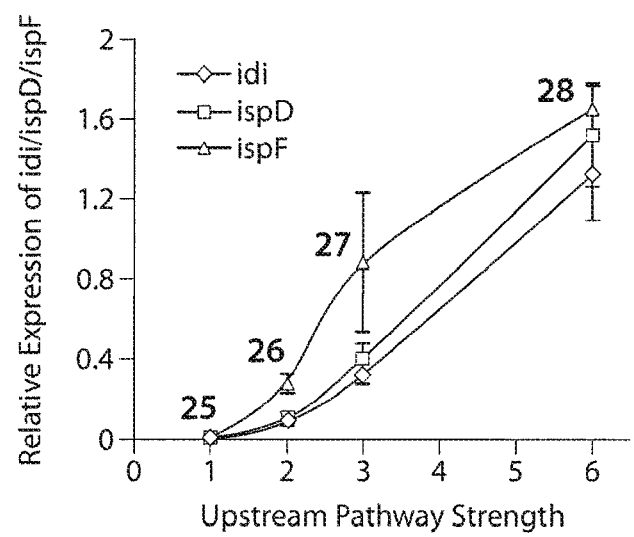
FIGS. 14A and 14B. Pathway strength correlates to transcriptional gene expression levels.
Figure 14B:
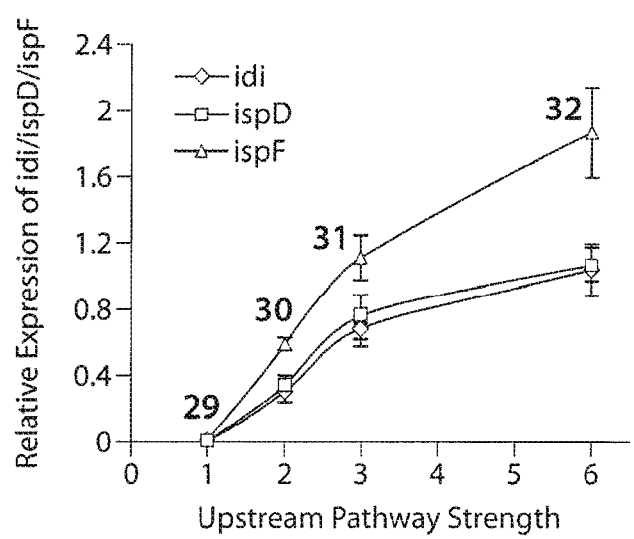

Example 5: Upstream and Downstream Pathway Expression Levels and Cell Growth Reveal Underlying Complexity For a more detailed understanding of the engineered balance in pathway expression, we quantified the transcriptional gene expression levels of dxs (upstream pathway) and TS (downstream pathway) for the highest taxadiene producing strains and neighboring strains from FIGS. 2C and 2D (strains 17, 22 and 25-32) (FIGS. 4A, 4B). As we hypothesized, expression of the upstream pathway increased monotonically with promoter strength and copy number for the MEP vector from: native promoter, Trc, T5, T7, and 10 copy and 20 copy plasmids, as seen in the DXS expression (FIG. 4A). Thus we found that dxs expression level correlates well with the upstream pathway strength. Similar correlations were found for the other genes of the upstream pathway, idi, ispD and ispF (FIGS. 14A, 14B). In the downstream gene expression, a ~2 fold improvement was quantified after transferring the pathway from 5 to 10 copy plasmid (25-28 series and 29-32 series) (FIG. 4B).

Figure 4C:
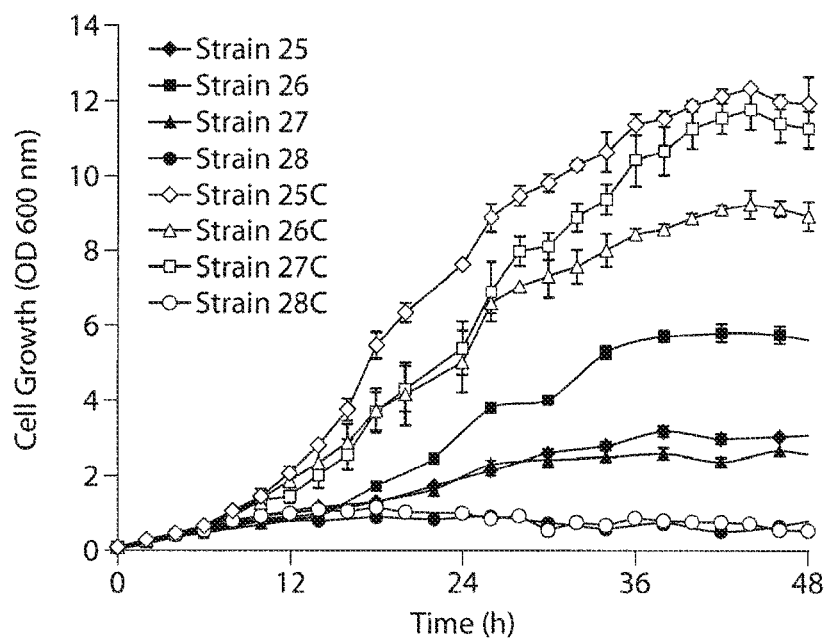
Figure 4D:
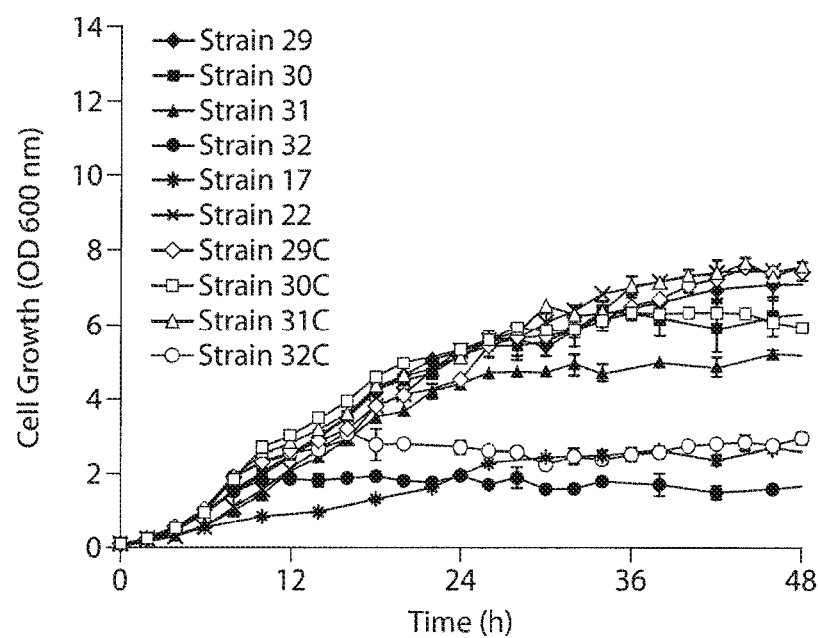

While promoter and copy number effects influenced the gene expressions, secondary effects on the expression of the other pathway were also prominent. FIG. 4A shows that for the same dxs expression cassettes, by increasing the copy number of the TS plasmid from 5 to 10, dxs expression was increased. Interestingly, the 5 copy TS plasmid (strains 25-28 series) contained substantially higher taxadiene yields (FIG. 2D) and less growth (FIGS. 4C, 4D) than the 10 copy TS plasmid. Control plasmids that did not contain the taxadiene heterologous pathway, grew two fold higher densities, implying growth inhibition in the strains 25-28 series is directly related to the taxadiene metabolic pathway and the accumulation of taxadiene and its direct intermediates (FIG. 4C). However the strain 29-32 series only showed modest increases in growth yield when comparing the empty control plasmids to the taxadiene expressing strains (FIG. 4D). This interplay between growth, taxadiene production, and expression level can also be seen with the plasmid-based upstream expression vectors (strain 17 and 22). Growth inhibition was much larger in the 10 copy, high taxadiene producing strain (strain 17) compared to the 20 copy, lower taxadiene producing strain (strain 22) (FIG. 4D). Therefore product toxicity and carbon diversion to the heterologous pathway are likely to impede growth, rather than plasmid-maintenance.

Also unexpected was the profound effect of the upstream expression vector on downstream expression. FIG. 4B would have two straight lines, if there was no cross talk between the pathways. However, ~3 fold changes in TS expression are observed for different MEP expression vectors. This is likely due to significant competition for resources (raw material and energy) that are withdrawn from the host metabolism for overexpression of both the four upstream and two downstream genes.[38] Compared to the control strain 25c, a 4 fold growth inhibition was observed with strain 25 indicated that high overexpression of synthetic taxadiene pathway induced toxicity altering the growth phenotype compared to the overexpression of native pathway (FIG. 4C). However, as upstream expression increased, downstream expression was reduced, inadvertently in our case, to desirable levels to balance the upstream and downstream pathways, minimizing growth inhibition (strain 26).

At the extreme of protein overexpression, T7 promoter-driven MEP pathway resulted in severe growth inhibition, due to the synthesis of four proteins at high level (strains 28 and 32). Expression of the TS genes by T7 does not appear to have as drastic effect by itself. The high rates of protein synthesis from the T7 induced expression (FIGS. 4A, 4B) could lead to the down regulation of the protein synthesis machinery including components of housekeeping genes from early growth phase impairs the cell growth and lower the increase in biomass.[39,40] We hypothesized that our observed complex growth phenotypes are cumulative effects of (1) toxicity induced by activation of isoprenoid/taxadiene metabolism, and (2) and the effects of high recombinant protein expression. Altogether our multivariate-modular pathway engineering approach generated unexpected diversity in terpenoid metabolism and its correlation to the pathway expression and cell physiology. Rational design of microbes for secondary metabolite production will require an understanding of pathway expression that goes beyond a linear/independent understanding of promoter strengths and copy numbers. However, simple, multivariate approaches, as employed here, can introduce the necessary diversity to both (1) find high producers, and (2) provide a landscape for the systematic investigation of higher order effects that are dominant, yet underappreciated, in metabolic pathway engineering.

Example 6: Engineering Taxol P450-Based Oxidation Chemistry in *E. coli*

A central feature in the biosynthesis of Taxol is oxygenation at multiple positions of the taxane core structure, reactions that are considered to be mediated by cytochrome P450-dependent monooxygenases.[41] After completion of the committed cyclization step of the pathway, the parent olefin, taxa-4(5),11(12)-diene, is next hydroxylated at the C5 position by a cytochrome P450 enzyme, representing the first of eight oxygenation steps (of the taxane core) on route to Taxol (FIG. 6).[42] Thus, a key step towards engineering Taxol-producing microbes is the development of P450-based oxidation chemistry in vivo. The first oxygenation step is catalyzed by a cytochrome P450, taxadiene 5α-hydroxylase, an unusual monooxygenase catalyzing the hydroxylation reaction along with double bond migration in the diterpene precursor taxadiene (FIG. 5A). We report the first successful extension of the synthetic pathway from taxadiene to taxadien-5α-ol and present the first examples of in vivo production of any functionalized Taxol intermediates in *E. coli*.

In general, functional expression of plant cytochrome P450 is challenging[43] due to the inherent limitations of bacterial platforms, such as the absence of electron transfer machinery, cytochrome P450 reductases, and translational incompatibility of the membrane signal modules of P450 enzymes due to the lack of an endoplasmic reticulum. Recently, through transmembrane (TM) engineering and the generation of chimera enzymes of P450 and CPR reductases, some plant P450's have been expressed in *E. coli* for the biosynthesis of functional molecules.[22,44] Still, every plant cytochrome p450 is unique in its transmembrane signal sequence and electron transfer characteristics from its reductase counterpart.[45] Our initial studies were focused on optimizing the expression of codon-optimized synthetic taxadiene 5α-hydroxylase by N-terminal transmembrane engineering and generating chimera enzymes through translational fusion with the CPR redox partner from the *Taxus* species, *Taxus* cytochrome P450 reductase (TCPR) (FIG. 5B).[42,44,46] One of the chimera enzymes generated, At24T5αOH-tTCPR, was highly efficient in carrying out the first oxidation step with more than 98% taxadiene conversion to taxadien-5α-ol and the byproduct 5(12)-Oxa-3(11)-cyclotaxane (OCT) (FIG. 9A).

Compared to the other chimeric P450s, At24T5αOH-tTCPR yielded two-fold higher (21 mg/L) production of taxadien-5α-ol. As well, the weaker activity of At8T5αOH-tTCPR and At24T5αOH-tTCPR resulted in accumulation of a recently characterized byproduct, a complex structural rearrangement of taxadiene into the cyclic ether 5(12)-Oxa-3(11)-cyclotaxane (OCT) (FIG. 9).[47] The byproduct accumulated at approximately equal amounts as the desired product taxadien-5α-ol. The OCT formation was mediated by an unprecedented Taxus cytochrome P450 reaction sequence involving oxidation and subsequent cyclizations.[47] Thus, it seems likely that by protein engineering of the taxadiene 5α-hydroxylases, termination of the reaction before cyclization will prevent the accumulation of such undesirable byproduct and channeling the flux to taxadien-5α-ol could be achieved.

Figure 5D:
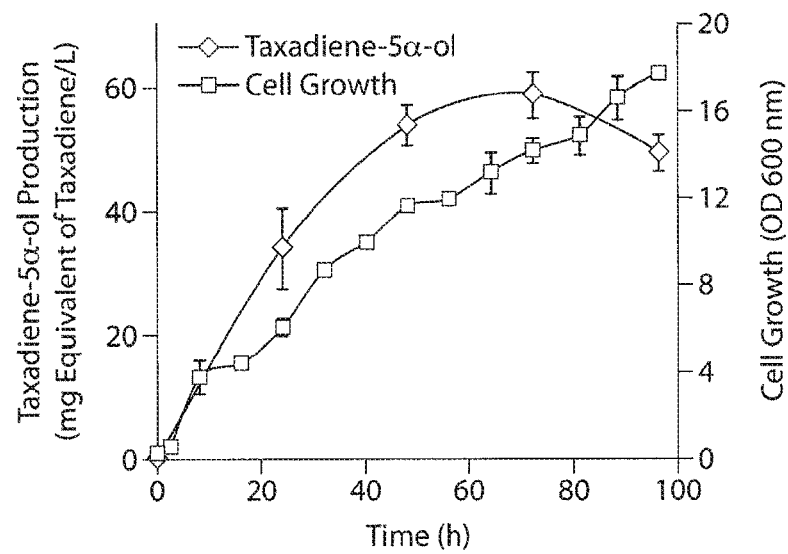

The productivity of strain 26-At24T5αOH-tTCPR was significantly reduced relatively to that of taxadiene production by the parent strain 26 (~300 mg/L) with a concomitant increase in the accumulation of the previously described uncharacterized metabolite. No taxadiene accumulation was observed. Apparently, the introduction of an additional medium copy plasmid (10 copy, p10T7) bearing the At24T5αOH-tTCPR construct disturbed the carefully engineered balance in the upstream and downstream pathway of strain 26. Small scale fermentations were carried out in bioreactors to quantify the alcohol production by strain 26-At24T5αOH-tTCPR. The time course profile of taxadien-5α-ol accumulation (FIG. 5D) indicates alcohol production of up to 58±3 mg/L with an equal amount of the OCT byproduct produced. The observed alcohol production was ~2400 fold higher than previous production in *S. cerevisiae*.[17] Further increases of taxadien-5α-ol production are likely possible through pathway optimization and protein engineering.

The multivariate-modular approach of pathway optimization has yielded very high producing strains of a critical Taxol precursor. Furthermore, the recombinant constructs have been equally effective in redirecting flux towards the synthesis of other complex pharmaceutical compounds, such as mono-, sesqui- and di-terpene (geraniol, linalool, amorphadiene and levopimaradiene) products engineered from the same pathway (unpublished results). Thus, our pathway engineering opens new avenues to bio-synthesize natural products, especially in the context of microbially-derived terpenoids for use as chemicals and fuels from renewable resources. By focusing on the universal terpenoid precursors IPP and DMAPP, it was possible to, first, define the critical pathway modules and then modulate expression such as to optimally balance the pathway modules for seamless precursor conversion and minimal intermediate accumulation. This approach seems to be more effective than combinatorial searches of large genetic spaces and also does not depend on a high throughput screen.

The MEP-pathway is energetically balanced and thus overall more efficient in converting either glucose or glycerol to isoprenoids. Yet, during the past 10 years, many attempts at engineering the MEP-pathway in *E. coli* to increase the supply of the key precursors IPP and DMAPP for carotenoid[28, 47], sesquiterpenoid[23] and diterpenoid[61] overproduction met with limited success. This inefficiency was attributed to unknown regulatory effects associated specifically with the expression of the MEP-pathway in *E. coli*[23]. Here we provide evidence that such limitations are correlated with the accumulation of the metabolite indole, owing to the non-optimal expression of the pathway, which inhibits the isoprenoid pathway activity. Taxadiene overproduction (under conditions of indole formation suppression), establishes the MEP-pathway as a very efficient route for biosynthesis of pharmaceutical and chemical products of the isoprenoid family. One simply needs to carefully balance the modular pathways as suggested by our multivariate-modular pathway engineering approach.

For successful microbial production of Taxol, demonstration of the chemical decoration of the taxadiene core by P450 based oxidation chemistry is essential.[41] Cytochrome P450 monooxygenases constitute about one half of the 19 distinct enzymatic steps in the Taxol biosynthetic pathway. Characteristically, these genes show unusual high sequence similarity with each other (>70%) but low similarity (<30%) with other plant P450s.[14] Due to the apparent similarity among Taxol monooxygenases, expressing the proper activity for carrying out the specific P450 oxidation chemistry was a particular challenge. Through TM engineering and construction of an artificial chimera enzyme with redox partner (TCPR), the Taxol cytochrome P450, taxadiene 5α-hydroxylase, was functionally expressed in *E. coli* and shown to efficiently convert taxadiene to the corresponding alcohol product in vivo. Previous in vitro studies have described the mechanism of converting taxadiene to taxadien-5α-ol by native taxadiene 5α-hydroxylase enzyme, but have not discussed the same conversion in vivo.[42] This oxygenation and rearrangement reaction involves hydrogen abstraction from C20 position of the taxadiene to form an allylic radical intermediate, followed by regio- and stereo-specific oxygen insertion at C5 position to yield the alcohol derivative (FIG. 5A). The observed modest abundance of the enzyme in Taxus cells, and the low $k_{cat}$ values suggested that the 5a-hydroxylation step of Taxol biosynthesis is slow relative to the downstream oxygenations and acylations in the Taxol pathway.[41] Thus, engineering this step is key to Taxol synthesis, especially in the context of functional engineering of Taxol P450's in prokaryotic host such as *E. coli*. In addition, this step was limiting in previous efforts of constructing the pathway in yeast.[17] The engineered construct in this study demonstrated >98% conversion of taxadiene in vivo with product accumulation to ~60 mg/L, a 2400 fold improvement over previous heterologous expression in yeast. This study has therefore succeeded not only in synthesizing significantly greater amounts of key Taxol intermediates but also provides the basis for the synthesis of subsequent metabolites in the pathway by similar P450 chemistry.

Prior studies on structure-activity relationship on Taxol have shown that alterations made either by removal or addition of some of its functional groups did not change materially the activity of the Taxo.[1, 48] Such studies, however, were limited due to the restricted ability to introduce changes by chemical synthesis. Availability of a microbial path for Taxol synthesis will drastically expand the space of chemical modifications that can be examined, thus increasing the probability of identifying more potent drug candidates. This offers exciting new opportunities for drug development, especially when considering that such drug candidates will also be associated with an efficient production route.

In the past few decades, Taxol has spawned more interest within the scientific communities and general public than any other natural product drug candidate.[10] A major supply crisis is predicted from the projected increase in the use of Taxol or Taxol analogs for cancer chemotherapy, requiring new production routes, such as engineering of Taxol biosynthetic machinery in microbes.[8] While a few endophytic fungi of Taxus species have been isolated capable of producing Taxol naturally, these microbial systems have yet to demonstrate suitability for sustainable production of the drug.[49] The results reported here represent a disruptive step towards a microbially-derived Taxol or Taxol precursor, by removing the bottlenecks in the committed precursor pathway. Furthermore, the assembly of a synthetic pathway offers new possibilities to tailor Taxol analogs by selectively engineering the pathway, thereby altering the taxane structure. These developments raise optimism for a microbial route for the cost-effective production of Taxol or suitable Taxol precursors.

TABLE 1

Ranking of upstream and downstream pathway expression in arbitrary units (a.u.). The MEP pathway and GGPP synthase/taxadiene synthase pathway expression levels were estimated using published values of promoter strengths and copy number. Promoter strengths were calculated as trc = 1, T5 = 1.96, T7 = 4.97, based on Brosius et. al. and Brunner et. al.[33,34] Gene copy number was assigned by published copy numbers for origin of replication for the different plasmids used, and one copy was used for integrations.[35-37] Total expression was calculated as the product of promoter strength and gene copy number. Native expression of the MEP pathway was arbitrarily assigned a value of one, and changing the operon order of GGPP synthase and taxadiene was assumed to affect taxadiene synthase expression by 20%.[35] These estimates of total expression guided engineering efforts. E—*E. coli* K12 MG1655 with two deletions ΔrecAΔendA; EDE3—K12 MG1655 ΔrecAΔendA with a T7 RNA polymerase (DE3) integrated; MEP—dxs-idi-ispDF operon; GT—GPPS-TS operon; TG—TS-GPPS operon; Ch1—1 copy in chromosome; Trc—trc promoter; T5—T5 promoter; T7—T7 promoter; p5—~5 copy plasmid (pSC101);, p10—~10 copy plasmid (p15A); and p20—~20 copy plasmid (pBR322).

| Strain | | Upstream MEP | | | | Downstream GT or TG | | | Taxadiene (mg/L) | |
|---|---|---|---|---|---|---|---|---|---|---|
| # | Pathway engineering | Construct (in addition to native copy)$ | Copies | Promoter | Expression Strength* (a.u.) | Construct | Copies GT/TG | Promoter | Expression Strength (a.u)# | Mean | SD |
| 1 | Ep20TrcGT | N/A | 0 | 0 | 1* | pBR322 | 20 | 1.00 | 20 | 0.02 | 0.01 |
| 2 | ECh1TrcMEPp20TrcGT | Chr.$ | 1 | 1 | 2 | pBR322 | 20 | 1.00 | 20 | 16.00 | 1.59 |
| 3 | Ep5TrcMEPp20TrcGT | pSC101 | 5 | 1 | 6 | pBR322 | 20 | 1.00 | 20 | 2.55 | 0.21 |
| 4 | Ep10TrcMEPp20TrcGT | p15A | 10 | 1 | 11 | pBR322 | 20 | 1.00 | 20 | 1.93 | 0.323 |
| 5 | Ep20TrcTG | N/A | 0 | 0 | 1 | pBR322 | 20 | 1.20 | 24 | 0.19 | 0.01 |

TABLE 1-continued

Ranking of upstream and downstream pathway expression in arbitrary units (a.u.). The MEP pathway and GGPP synthase/taxadiene synthase pathway expression levels were estimated using published values of promoter strengths and copy number. Promoter strengths were calculated as trc = 1, T5 = 1.96, T7 = 4.97, based on Brosius et. al. and Brunner et. al.[33,34] Gene copy number was assigned by published copy numbers for origin of replication for the different plasmids used, and one copy was used for integrations.[35-37] Total expression was calculated as the product of promoter strength and gene copy number. Native expression of the MEP pathway was arbitrarily assigned a value of one, and changing the operon order of GGPP synthase and taxadiene was assumed to affect taxadiene synthase expression by 20%.[35] These estimates of total expression guided engineering efforts. E—*E coli* K12 MG1655 with two deletions ΔrecAΔendA; EDE3—K12 MG1655 ΔrecAΔendA with a T7 RNA polymerase (DE3) integrated; MEP—dxs-idi-ispDF operon; GT—GPPS-TS operon; TG—TS-GPPS operon; Ch1—1 copy in chromosome; Trc—trc promoter; T5—T5 promoter; T7—T7 promoter; p5—~5 copy plasmid (pSC101);, p10—~10 copy plasmid (p15A); and p20—~20 copy plasmid (pBR322).

| | | Upstream MEP | | | | Downstream GT or TG | | | Taxadiene (mg/L) | |
|---|---|---|---|---|---|---|---|---|---|---|
| Strain # | Pathway engineering | Construct (in addition to native copy)$ | Copies | Promoter | Expression Strength* (a.u.) | Construct | Copies GT/TG | Promoter | Expression Strength (a.u)# | Mean | SD |
| 6 | Ep20T5GT | N/A | 0 | 0 | 1 | pBR322 | 20 | 1.96 | 39 | 4.36 | 0.533 |
| 7 | Ep20T5GTTrcT | N/A | 0 | 0 | 1 | pBR322 | 20 | 2.96 | 59 | 1.74 | 0.265 |
| 8 | ECh1TrcMEPp20TrcTG | Chr. | 1 | 1 | 2 | pBR322 | 20 | 1.20 | 24 | 45.44 | 2.28 |
| 9 | ECh1TrcMEPp20T5GT | Chr. | 1 | 1 | 2 | pBR322 | 20 | 1.96 | 39 | 16.52 | 0.84 |
| 10 | ECh1TrcMEPp20T5GT-TrcT | Chr. | 1 | 1 | 2 | pBR322 | 20 | 2.96 | 59# | 2.52 | 0.30 |
| 11 | Ep5TrcMEPp20TrcTG | pSC101 | 5 | 1 | 6 | pBR322 | 20 | 1.20 | 24 | 7.41 | 0.63 |
| 12 | Ep5TrcMEPp20T5GT | pSC101 | 5 | 1 | 6 | pBR322 | 20 | 1.96 | 39 | 21.23 | 5.86 |
| 13 | Ep5TrcMEPp20T5TG-TrcT | pSC101 | 5 | 1 | 6 | pBR322 | 20 | 2.96 | 59 | 1.40 | 0.10 |
| 14 | Ep10TrcMEPp20TrcTG | p15A | 10 | 1 | 11 | pBR322 | 20 | 1.20 | 24 | 2.36 | 0.29 |
| 15 | Ep10TrcMEPp20T5GT | p15A | 10 | 1 | 11 | pBR322 | 20 | 1.96 | 39 | 8.91 | 2.94 |
| 16 | Ep10TrcMEPp20T5GT-TrcT | p15A | 10 | 1 | 11 | pBR322 | 20 | 2.96 | 59 | 3.40 | 0.39 |
| 17 | EDE3p10TrcMEPp5T7TG | p15A | 10 | 1 | 11 | pSC101 | 5 | 5.96 | 31 | 125.00 | 8.37 |
| 18 | EDE3p20TrcMEPp5T7TG | pBR322 | 20 | 1 | 21 | pSC101 | 5 | 5.96 | 31 | 58.00 | 3.07 |
| 19 | EDE3p20T5MEPp5T7TG | pBR322 | 20 | 1.96 | 40 | pSC101 | 5 | 5.96 | 31 | 44.00 | 2.88 |
| 20 | EDE3p20T7MEPp5T7TG | pBR322 | 20 | 4.97 | 100 | pSC101 | 5 | 5.96 | 31 | 32.00 | 6.63 |
| 21 | EDE3p5TrcMEPp10T7TG | pSC101 | 5 | 1 | 6 | p15A | 10 | 5.96 | 61 | 7.00 | 1.40 |
| 22 | EDE3p20TrcMEPp10T7TG | pBR322 | 20 | 1 | 21 | p15A | 10 | 5.96 | 61 | 59.00 | 5.57 |
| 23 | EDE3p20T5MEPp10T7TG | pBR322 | 20 | 1.96 | 40 | p15A | 10 | 5.96 | 61 | 58.00 | 5.68 |
| 24 | EDE3p20T7MEPp10T7TG | pBR322 | 20 | 4.97 | 100 | p15A | 10 | 5.96 | 61 | 20.00 | 0.73 |
| 25 | EDE3p5T7TG | N/A | 0 | 0 | 1 | pSC101 | 5 | 5.96 | 31 | 19.00 | 8.23 |
| 26 | EDE3Ch1TrcMEPp5T7TG | Chr. | 1 | 1 | 2 | pSC101 | 5 | 5.96 | 31 | 297.00 | 10.21 |
| 27 | EDE3Ch1T5MEPp5T7TG | Chr | 1 | 1.96 | 3 | pSC101 | 5 | 5.96 | 31 | 163.00 | 10.84 |
| 28 | EDE3Ch1T7MEPp5T7TG | Chr | 1 | 4.97 | 6 | pSC101 | 5 | 5.96 | 31 | 26.00 | 0.32 |
| 29 | EDE3p10T7TG | N/A | 0 | 0 | 1 | p15A | 10 | 5.96 | 61 | 8.00 | 0.39 |
| 30 | EDE3Ch1TrcMEPp10T7TG | Chr | 1 | 1 | 2 | p15A | 10 | 5.96 | 61 | 30.00 | 1.59 |
| 31 | EDE3Ch1T5MEPp10T7TG | Chr | 1 | 1.96 | 3 | p15A | 10 | 5.96 | 61 | 40.00 | 0.56 |
| 32 | EDE3Ch1T7MEPp10T7TG | Chr | 1 | 4.97 | 6 | p15A | 10 | 5.96 | 61 | 17.00 | 0.41 |

*A value of 1 was given to account for the native copies of the MEP pathway.
$MEP construct is localized in the chromosome.
p20T5GT-TrcT - An additional copy of gene T under separate promoter control (Trc) together operon GT (under T5 promoter) on the same plasmid. For the calculation strength, we have added the value as equivalent two separate operons (TrcT + T5GT = (20 × 1.96 + 20 × 1 = 59)) since our studies shows that expression of T was limited compared to G.

TABLE 2

Detail of all the plasmids constructed for the study

| No | Plasmid | Origin of replication | Antibiotic marker |
|---|---|---|---|
| 1 | p20T7MEP | pBR322 | Amp |
| 2 | p20TrcMEP | pBR322 | Amp |
| 3 | p20T5MEP | pBR322 | Amp |
| 4 | p20T7MEPKmFRP | pBR322 | Km |
| 5 | p20T5MEPKmFRP | pBR322 | Km |
| 6 | p20TrcMEPKm-FRP | pBR322 | Km |
| 7 | p10TrcMEP | p15A | Cm |
| 8 | p5TrcMEP | SC101 | Spect |
| 9 | p20TrcGT | pBR322 | Amp |
| 10 | p20TrcTG | pBR322 | Amp |
| 11 | p20T5GT | pBR322 | Amp |
| 12 | p10T7TG | p15A | Cm |
| 13 | p5T7TG | SC101 | Spect |
| 14 | p10At8T5αOH-tTCPR | p15A | Cm |
| 15 | p10At24T5αOH-tTCPR | p15A | Cm |
| 16 | p10At42T5αOH-tTCPR | p15A | Cm |

TABLE 3

Details of the primer used for the cloning of plasmids, chromosomal delivery of the MEP pathway and qPCR measurements.

| SEQ ID NO | Primer Name | Sequences |
|---|---|---|
| 1 | dxsNdeI(s) | CGGCATATGAGTTTTGATATTGCCAAATACCCG |
| 2 | dxsNheI(a) | CGGCTAGCTTATGCCAGCCAGGCCTTGATTTTG |
| 3 | idiNheI(s) | CGCGGCTAGCGAAGGAGATATACATATGCAAACGGAACACGTCATTTTATTG |
| 4 | idiEcoRI(a) | CGGAATTCGCTCACAACCCCGGCAAATGTCGG |
| 5 | ispDFEcoRI(s) | GCGAATTCGAAGGAGATATACATATGGCAACCACTCATTTGGATGTTTG |
| 6 | ispDFXhoI(a) | GCGCTCGAGTCATTTTGTTGCCTTAATGAGTAGCGCC |
| 7 | dxsidiispDFNcoI(s) | TAAACCATGGGTTTTGATATTGCCAAATACCCG |
| 8 | dxsidiispDFKpnI(a) | CGGGGTACCTCATTTTGTTGCCTTAATGAGTAGCGC |
| 9 | dxsidiispDFXhoI(a) | CGGCTCGAGTCATTTTGTTGCCTTAATGAGTAGCGC |
| 10 | T5AgeI(s) | CGTAACCGGTGCCTCTGCTAACCATGTTCATGCCTTC |
| 11 | T5NheI(a) | CTCCTTCGCTAGCTTATGCCAGCC |
| 52 | GGPPSNcoI(s) | CGTACCATGGTTGATTTCAATGAATATATGAAAAGTAAGGC |
| 12 | GGPPSEcoRI(a) | CGTAGAATTCACTCACAACTGACGAAACGCAATGTAATC |
| 13 | TXSEcoRI(s) | CGTAGAATTCAGAAGGAGATATACATATGGCTAGCTCTACGGGTACG |
| 14 | TXSsalI(a) | GATGGTCGACTTAGACCTGGATTGGATCGATGTAAAC |
| 15 | TXSNcoI(s) | CGTACCATGGCTAGCTCTACGGGTACG |
| 16 | TXSEcoRI(a) | CGTAGAATTCTTAGACCTGGATTGGATCGATGTAAAC |
| 17 | GGPPSEcoRI(s) | CGTAGAATTCAGAAGGAGATATACATATGTTTGATTTCAATGAATATATGAAAAGTAAGGC |
| 18 | GGPPSSalI(a) | GATGGTCGACTCACAACTGACGAAACGCAATGTAATC |
| 19 | TSXhoI(a) | GATGCTCGAGTTAGACCTGGATTGGATCGATGTAAAC |
| 20 | pTrcSal(s) | GCCGTCGACCATCATCATCATCATC |
| 21 | pTrcXba(a) | GCAGTCTAGAGCCAGAACCGTTATGATGTCGGCGC |
| 22 | pCLBspEI(s) | CGTGTCCGGAGCATCTAACGCTTGAGTTAAGCCGC |
| 23 | pCLXbaI(a) | GCAGTCTAGAGGAAACCTGTCGTGCCAGCTGC |
| 24 | KmFRPXhoI(s) | GACGCTCGAGGAGCAATAACTAGCATAACCCCTTGGGGCCTCTAAACGGGTCTTGAGGGGTTTTTTGCTTGTGTAGGCTGGAGCTGCTTCG |
| 25 | KmFRPScaI(a) | GACGAGTACTGAACGTCGGAATTGATCCGTCGAC |
| 26 | KmFRPSacI(s) | GACGGAGCTCGAGCAATAACTAGCATAACCCCTTGGGGCCTCTAAACGGGTCTTGAGGGGTTTTTTGCTTGTGTAGGCTGGAGCTGCTTCG |
| 27 | IntT7T5(s) | ATGACGATTTTGATAATTATGAAGTGTGGTTTGTCATTGCATTAATTGCGTTGCGCTCACTG |
| 28 | IntTrc(s) | ATGACGATTTTGATAATTATGAAGTGTGGTTTGTCATTGGCATCCGCTTACAGACAAGCTGTG |
| 29 | Int(a) | TTAGCGACGAAACCCGTAATACACTTCGTTCCAGCGCAGCCGACGTCGGAATTGATCCGTCGAC |

TABLE 3-continued

Details of the primer used for the cloning of plasmids, chromosomal delivery of the MEP pathway and qPCR measurements.

| SEQ ID NO | Primer Name | Sequences |
|---|---|---|
| 30 | CYP17At8AANdeI (s) | CGTACATATGGCTCTGTTATTAGCAGTTTTTGTGGCGAAA TTTAACGAAGTAACCCAGC |
| 31 | CYP17At24AANdeI (s) | CGTACATATGGCTCTGTTATTAGCAGTTTTTTTTAGCATC GCTTTGAGTGCAATTG |
| 32 | CYP17At42AANdeI (s) | CGTACATATGGCTCTGTTATTAGCAGTTTTTTTTCGCTCG AAACGTCATAGTAGCCTG |
| 33 | CYPLinkBamHI (a) | CGCGGGATCCGGTGCTGCCCGGACGAGGGAACAGTTTGA TTGAAAACCC |
| 34 | CPRBamHI (s) | CGCGGGATCCCGCCGTGGTGGAAGTGATACACAG |
| 35 | CPRSalI (a) | CGCGGTCGACTTACCAAATATCCCGTAAGTAGCGTCCAT C |
| 36 | DXS qPCR (s) | A T T C A A A A G C T T C C G G T C C T |
| 37 | DXS qPCR (a) | A T C T G G C G A C A T T C G T T T T C |
| 38 | TS qPCR (s) | G A C G A A C T G T C A C C C G A T T T |
| 39 | TS qPCR (a) | G C T T C G C G G G T A G T A G A C A G |
| 40 | rrsA qPCR (s) | A G G C C T T C G G G T T G T A A A G T |
| 41 | rrsa qPCR (a) | A T T C C G A T T A A C G C T T G C A C |

TABLE 4

Protein and Codon optimized nucleotide sequences.

GGPP synthase (SEQ ID NO: 42)
MFDFNEYMKSKAVAVDAALDKAIPLEYPEKIHESMRYSLLAGGKRVRPALCIAACE
LVGGSQDLAMPTACAMEMIHTMSLIHDDLPCMDNDDFRRGKPTNHKVFGEDTAVL
AGDALLSFAFEHIAVATSKTVPSDRTLRVISELGKTIGSQGLVGGQVVDITSEGDANV
DLKTLEWIHIHKTAVLLECSVVSGGILGGATEDEIARIRRYARCVGLLFQVVDDILDV
TKSSEELGKTAGKDLLTDKATYPKLMGLEKAKEFAAELATRAKEELSSFDQIKAAPL
LGLADYIAFRQN (SEQ ID NO: 43)
ATGTTTGATTTCAATGAATATATGAAAAGTAAGGCTGTTGCGGTAGACGCGGCTC
TGGATAAAGCGATTCCGCTGGAATATCCCGAGAAGATTCACGAATCGATGCGCT
ACTCCCTGTTAGCAGGAGGGAAACGCGTTCGTCCGGCATTATGCATCGCGGCCTG
TGAACTCGTCGGCGGTTCACAGGACTTAGCAATGCCAACTGCTTGCGCAATGGA
AATGATTCACACAATGAGCCTGATTCATGATGATTTGCCTTGCATGGACAACGAT
GACTTTCGGCGCGGTAAACCTACTAATCATAAGGTTTTTGGCGAAGATACTGCAG
TGCTGGCGGGCGATGCGCTGCTGTCGTTTGCCTTCGAACATATCGCCGTCGCGAC
CTCGAAAACCGTCCCGTCGGACCGTACGCTTCGCGTGATTTCCGAGCTGGGAAAG
ACCATCGGCTCTCAAGGACTCGTGGGTGGTCAGGTAGTTGATATCACGTCTGAGG
GTGACGCGAACGTGGACCTGAAAACCCTGGAGTGGATCCATATTCACAAAACGG
CCGTGCTGCTGGAATGTAGCGTGGTGTCAGGGGGGATCTTGGGGGGCGCCACGG
AGGATGAAATCGCGCGTATTCGTCGTTATGCCCGCTGTGTTGGACTGTTATTTCA
GGTGGTGGATGACATCCTGGATGTCACAAAATCCAGCGAAGAGCTTGGCAAGAC
CGCGGGCAAAGACCTTCTGACGGATAAGGCTACATACCCGAAATTGATGGGCTT
GGAGAAAGCCAAGGAGTTCGCAGCTGAACTTGCCACGCGGGCGAAGGAAGAAC
TCTCTTCTTTCGATCAAATCAAAGCCGCGCCACTGCTGGGCCTCGCCGATTACAT
TGCGTTTCGTCAGAAC Taxadiene synthase (SEQ ID NO: 44)
MSSSTGTSKVVSETSSTIVDDIPRLSANYHGDLWHHNVIQTLETPFRESSTYQERADE
LVVKIKDMFNALGDGDISPSAYDTAWVARLATISSDGSEKPRFPQALNWVFNNQLQ
DGSWGIESHFSLCDRLLNTTNSVIALSVWKTGHSQVQQGAEFIAENLRLLNEEDELSP
DFQIIFPALLQKAKALGINLPYDLPFIKYLSTTREARLTDVSAAADNIPANMLNALEGL TABLE 4-continued Protein and Codon optimized nucleotide sequences.

EEVIDWNKIMRFQSKDGSFLSSPASTACVLMNTGDEKCFTFLNNLLDKFGGCVPCM
YSIDLLERLSLVDNIEHLGIGRHFKQEIKGALDVYYRHWSERGIGWGRDSLVPDLNTT
ALGLRTLRMHGYNVSSDVLNNFKDENGRFFSSAGQTHVELRSVVNLFRASDLAFPD
ERAMDDARKFAEPYLREALATKISTNTKLFKEIEYVVEYPWHMSIPRLEARSYIDSYD
DNYVWQRKTLYRMPSLSNSKCLELAKLDFNIVQSLHQEELKLLTRWWKESGMADI
NFTRHRVAEVYFSSATFEPEYSATRIAFTKIGCLQVLFDDMADIFATLDELKSFTEGV
KRWDTSLLHEIPECMQTCFKVWFKLMEEVNNDVVKVQGRDMLAHIRKPWELYFNC
YVQEREWLEAGYIPTFEEYLKTYAISVGLGPCTLQPILLMGELVKDDVVEKVHYPSN
MFELVSLSWRLTNDTKTYQAEKARGQQASGIACYMKDNPGATEEDAIKHICRVVDR
ALKEASFEYFKPSNDIPMGCKSFIFNLRLCVQIFYKFIDGYGIANEEIKDYIRKVYIDPI
QV (SEQ ID NO: 45)
ATGTCTAGCTCTACGGGTACGTCTAAAGTCGTGAGTGAAACCTCATCGACGATCG
TGGACGATATTCCACGCTTGTCGGCGAACTATCATGGAGATCTGTGGCATCATAA
CGTCATTCAGACATTGGAAACCCCGTTTCGCGAAAGTAGCACCTACCAGGAACG
GGCAGATGAATTAGTCGTGAAAATCAAAGATATGTTTAATGCATTAGGAGATGG
AGACATCTCGCCCAGCGCATATGATACGGCGTGGGTGGCTCGGTTGGCCACGATT
AGCTCCGATGGCAGTGAAAAGCCGCGTTTCCCGCAGGCGCTGAACTGGGTGTTT
AATAATCAATTGCAGGATGGCAGCTGGGGCATTGAATCTCACTTTAGCCTCTGTG
ACCGGTTACTCAACACGACAAACTCCGTAATTGCGTTGTCAGTTTGGAAAACGGG
CCATAGCCAGGTTCAACAGGGCGCGGAATTTATCGCTGAAATCTGCGCCTGCTG
AACGAGGAGGACGAACTGTCACCCGATTTTCAGATTATTTTTCCGGCTTTACTCC
AGAAAAGCCAAAGCCTTAGGCATCAACCTGCCATATGATCTGCCGTTCATCAAGTA
TCTGTCTACTACCCGCGAAGCCCGTCTCACTGACGTCTCTGCGGCGGCGGACAAT
ATTCCAGCGAACATGCTGAACGCACTGGAAGGGCTGGAAGAGGTTATCGACTGG
AATAAAATCATGCGCTTCCAAAGCAAGGACGGTAGCTTCTTAAGCAGCCCAGCA
TCTACTGCTTGTGTTCTGATGAATACCGGAGACGAAAAGTGCTTTACGTTTCTGA
ACAATCTGCTGGACAAATTTGGGGGTTGTGTTCCTTGTATGTATTCCATTGATCTG
TTGGAACGTCTGTCGCTGGTCGATAACATTGAACACTTAGGTATCGGCCGCCACT
TCAAACAAGAAATCAAGGGGCGTTGATTATGTATACCGTCATTGGAGCGAGC
GTGGTATTGGTTGGGGCGCGATAGCTTGGTACCTGATCTGAACACCACTGCTTT
GGGACTGCGCACTCTTCGTATGCACGGATACAACGTTAGTTCCGATGTCCTCAAT
AATTTCAAGGACGAGAACGGCCGTTTTTTCAGCTCGGCCGGTCAGACGCATGTTG
AACTGCGGTCCGTAGTCAATCTCTTTCGCGCTAGTGATCTGGCCTTCCCCGACGA
GCGCGCTATGGACGATGCACGGAAGTTTGCCGAGCCGTATCTCCGCGAAGCCCT
GGCCACCAAAATTTCAACCAACACCAAGCTTTTCAAAGAAATTGAGTATGTAGT
AGAGTATCCGTGGCATATGTCTATTCCGCGCCTGGAAGCCCGCTCGTATATCGAT
TCTTACGATGACAATTATGTGTGGCAACGCAAAACACTGTACCGTATGCCCAGCC
TGTCAAATAGTAAGTGTCTGGAGCTGGCAAACTGGATTTCAACATTGTGCAATC
CCTGCACCAAGAAGAGCTGAAATTACTGACTCGCTGGTGGAAGGAATCCGGCAT
GGCAGACATCAATTTTACGCGTCACCGTGTTGCAGAGGTGTACTTCTCCTCGGCG
ACCTTTGAGCCGGAGTATTCGGCCACACGTATTGCATTTACCAAGATTGGCTGCC
TTCAGGTGCTTTTTGACGATATGGCGGATATTTTTGCGACATTGATGAGCTTAA
ATCATTTACCGAAGGCGTGAAGCGTTGGGATACCTCTCTGTTGCATGAAATCCCC
GAATGTATGCAGACCTGCTTCAAAGTTTGGTTCAAACTGATGGAAGAAGTGAAC
AACGACGTCGTGAAAGTTCAGGGTCGTGATATGTTAGCACACATCCGCAAGCCG
TGGGAACTCTATTTCAATTGCTATGTGCAGGAGCGTGAATGGTTAGAAGCGGGT
ACATTCCTACCTTCGAAGAGTACTTAAAAACCTATGCCATTTCCGTCGGTTTAGG
CCCGTGCACTCTGCAGCCTATCTTGCTGATGGGTGAGCTGGTAAAGGATGATGTG
GTGGAAAAAGTTCACTACCCGTCGAATATGTTTGAACTGGTAAGTCTGAGTTGGC
GTCTGACAAACGACACCAAAACGTACCAGGCAGAAAAGGCACGTGGGCAACAG
GCAAGCGGTATCGCGTGTTATATGAAGGATAATCCGGGCGCTACTGAGGAAGAT
GCCATTAAGCATATCTGCCGTGTTGTGGATCGCGCTCTTAAAGAAGCGTCATTCG
AATATTTTAAACCTAGTAATGATATTCCGATGGGTTGTAAGTCATTCATTTTCAAT
CTTCGCCTGTGCGTGCAAATTTTTTACAAATTTATTGACGGCTACGGAATCGCCA
ACGAAGAAATCAAAGACTATATTCGTAAAGTTTACATCGATCCAATCCAGGTC

Cytochrome P450 Taxadiene 5a-hydroxylase (T5αOH)

(SEQ ID NO: 46)
MDALYKSTVAKFNEVTQLDCSTESFSIALSAIAGILLLLLLFRSKRHSSLKLPPGKLGIP
FIGESFIFLRALRSNSLEQFFDERVKKFGLVFKTSLIGHPTVVLCGPAGNRLILSNEEKL
VQMSWPAQFMKLMGENSVATRRGEDHIVMRSALAGFFGPGALQSYIGKMNTEIQS
HINEKWKGKDEVNVLPLVRELVFNISAILFFNIYDKQEQDRLHKLLETILVGSFALPID
LPGFGFHRALQGRAKLNKIMLSLIKKRKEDLQSGSATATQDLLSVLLTFRDDKGTPL
TNDEILDNFSSLLHASYDTTTSPMALIFKLLSSNPECYQKVVQEQLEILSNKEEGEEIT
WKDLKAMKYTWQVAQETLRMFPPVFGTFRKAITDIQYDGYTIPKGWKLLWTTYST
HPKDLYFNEPEKFMPSRFDQEGKHVAPYTFLPFGGGQRSCVGWEFSKMEILLFVHHF
VKTFSSYTPVDPDEKISGDPLPPLSKGFSIKLFPRP (SEQ ID NO: 47)
ATGGATGCCCTCTATAAGTCTACCGTGGCGAAATTTAACGAAGTAACCCAGCTGG
ATTGCAGCACTGAGTCATTTAGCATCGCTTTGAGTGCAATTGCCGGGATCTTGCT
GTTGCTCCTGCTGTTTCGCTCGAAACGTCATAGTAGCCTGAAATTACCTCCGGGC
AAACTGGGCATTCCGTTTATCGGTGAGTCCTTTATTTTTTTGCGCGCGCTGCGCAG
CAATTCTCTGGAACAGTTCTTTGATGAACGTGTGAAGAAGTTCGGCCTGGTATTT

TABLE 4-continued

Protein and Codon optimized nucleotide sequences.

```
AAAACGTCCCTTATCGGTCACCCGACGGTTGTCCTGTGCGGGCCCGCAGGTAATC
GCCTCATCCTGAGCAACGAAGAAAAGCTGGTACAGATGTCCTGGCCGGCGCAGT
TTATGAAGCTGATGGGAGAGAACTCAGTTGCGACCCGCCGTGGTGAAGATCACA
TTGTTATGCGCTCCGCGTTGGCAGGCTTTTTCGGCCCGGGAGCTCTGCAATCCTAT
ATCGGCAAGATGAACACGGAAATCCAAAGCCATATTAATGAAAAGTGGAAAGG
GAAGGACGAGGTTAATGTCTTACCCCTGGTGCGGGAACTGGTTTTTAACATCAGC
GCTATTCTGTTCTTTAACATTTACGATAAGCAGGAACAAGACCGTCTGCACAAGT
TGTTAGAAACCATTCTGGTAGGCTCGTTTGCCTTACCAATTGATTTACCGGGTTTC
GGGTTTCACCGCGCTTTACAAGGTCGTGCAAAACTCAATAAAATCATGTTGTCGC
TTATTAAAAACGTAAAGAGGACTTACAGTCGGGATCGGCCACCGCGACGCAGG
ACCTGTTGTCTGTGCTTCTGACTTTCCGTGATGATAAGGGCACCCCGTTAACCAA
TGACGAAATCCTGGACAACTTTAGCTCACTGCTTCACGCCTCTTACGACACCACG
ACTAGTCCAATGGCTCTGATTTTCAAATTACTGTCAAGTAACCCTGAATGCTATC
AGAAAGTCGTGCAAGAGCAACTCGAGATTCTGAGCAATAAGGAAGAAGGTGAA
GAAATTACCTGGAAAGATCTTAAGGCCATGAAATACACGTGCAGGTTGCGCAG
GAGACACTTCGCATGTTTCCACCGGTGTTCGGGACCTTCCGCAAAGCGATCACGG
ATATTCAGTATGACGGATACACAATCCCGAAAGGTTGGAAACTGTTGTGGACTA
CCTATAGCACTCATCCTAAGGACCTTTACTTCAACGAACCGGAGAAATTTATGCC
TAGTCGTTTCGATCAGGAAGGCAAACATGTTGCGCCCTATACCTTCCTGCCCTTT
GGAGGCGGTCAGCGGAGTTGTGTGGGTTGGGAGTTCTCTAAGATGGAGATTCTC
CTCTTCGTGCATCATTTCGTGAAAACATTTTCGAGCTATACCCCGGTCGATCCCG
ATGAAAAATTTCCGGCGATCCACTGCCGCCGTTACCGAGCAAAGGGTTTTCAAT
CAAACTGTTCCCTCGTCCG
```

Taxus NADPH: cytochrome P450 reductase (TCPR)

(SEQ ID NO: 48)
```
MQANSNTVEGASQGKSLLDISRLDHIFALLLNGKGGDLGAMTGSALILTENSQNLMI
LTTALAVLVACVFFFVWRRGGSDTQKPAVRPTPLVKEEDEEEDDSAKKKVTIFFGT
QTGTAEGFAKALAEEAKARYEKAVFKVVDLDNYAADDEQYEEKLKKEKLAFFMLA
TYGDGEPTDNAARFYKWFLEGKEREPWLSDLTYGVFGLGNRQYEHFNKVAKAVDE
VLIEQGAKRLVPVGLGDDDQCIEDDFTAWREQVWPELDQLLRDEDDEPTSATPYTA
AIPEYRVEIYDSVVSVYEETHALKQNGQAVYDIHHPCRSNVAVRRELHTPLSDRSCIH
LEFDISDTGLIYETGDHVGVHTENSIETVEEAAKLLGYQLDTIFSVHGDKEDGTPLGG
SSLPPPFPGPCTLRTALARYADLLNPPRKAAFLALAAHASDPAEAERLKFLSSPAGKD
EYSQWVTASQRSLLEIMAEFPSAKPPLGVFFAAIAPRLQPRYYSISSSPRFAPSRIHVTC
ALVYGPSPTGRIHKGVCSNWMKNSLPSEETHDCSWAPVFVRQSNFKLPADSTTPIVM
VGPGTGFAPFRGFLQERAKLQEAGEKLGPAVLFFGCRNRQMDYIYEDELKGYVEKG
ILTNLIVAFSREGATKEYVQHKMLEKASDTWSLIAQGGYLYVCGDAKGMARDVHR
TLHTIVQEQESVDSSKAEFLVKKLQMDGRYLRDIW
```

(SEQ ID NO: 49)
```
ATGCAGGCGAATTCTAATACGGTTGAAGGCGCGAGCCAAGGCAAGTCTCTTCTG
GACATTAGTCGCCTCGACCATATCTTCGCCCTGCTGTTGAACGGGAAAGGCGGAG
ACCTTGGTGCGATGACCGGGTCGGCCTTAATTCTGACGGAAAATAGCCAGAACTT
GATGATTCTGACCACTGCGCTGGCCGTTCTGGTCGCTTGCGTTTTTTTTTTCGTTT
GGCGCCGTGGTGGAAGTGATACACAGAAGCCCGCCGTACGTCCCACACCTCTTG
TTAAAGAAGAGGACGAAGAAGAAGAAGATGATAGCGCCAAGAAAAAGGTCACA
ATATTTTTTGGCACCCAGACCGGCACCGCCGAAGGTTTCGCAAAGGCCTTAGCTG
AGGAAGCAAAGGCACGTTATGAAAAGGCGGTATTTAAAGTCGTGGATTTGGATA
ACTATGCAGCGGATGACGAACAGTACGAAGAGAAGTTGAAAAAGGAAAAGCTA
GCGTTCTTCATGCTCGCCACCTACGGTGACGGCGAACCGACTGATAATGCCGCTC
GCTTTTATAAATGGTTCTCGAGGGTAAAGAGCGCGAGCCATGGTTGTCAGATCT
GACTTATGGCGTGTTTGGCTTAGGTAACCGTCAGTATGAACACTTTAACAAGGTC
GCGAAAGCGGTGGACGAAGTGCTCATTGAACAAGGCGCCAAACGTCTGGTACCG
GTAGGGCTTGGTGATGATGATCAGTGCATTGAGGACGACTTCACTGCCTGGAGA
GAACAAGTGTGGCCTGAGCTGGATCAGCTCTTACGTGATGAAGATGACGAGCCG
ACGTCTGCGACCCCGTACACGGCGGCTATTCCAGAATACCGGGTGGAAATCTAC
GACTCAGTAGTGTCGGTCTATGAGGAAACCCATGCGCTGAAACAAAATGGACAA
GCCGTATACGATATCCACCACCCGTGTCGCAGCAACGTGGCGGTACGTCGTGAG
CTGCATACCCCGCTGTCGGATCGTAGTTGTATTCATCTGGAATTCGATATTAGTG
ATACTGGGTTAATCTATGAGACGGGCGACCACGTTGGAGTTCATACCGAGAATTC
AATTGAAACCGTGGAAGAAGCAGCTAAACTGTTAGGTTACCAACTGGATACAAT
CTTCAGCGTGCATGGGGACAAGGAAGATGGAACACCATTGGGCGGGAGTAGCCT
GCCACCGCCGTTTCCGGGGCCCTGCACGCTGCGGACGGCGCTGGCACTGGCGC
GGACCTGCTGAACCCTCCGCGCAAAGCCGCCTTCCTGGCACTGGCCGCACACGC
GTCAGATCCGGCTGAAGCTGAACGCCTTAAATTTCTCAGTTCTCCAGCCGGAAAA
GACGAATACTCACAGTGGGTCACTGCGTCCCAACGCAGCCTCCTCGAGATTATGG
CCGAATTCCCCAGCGCGAAACCGCCGCTGGGAGTGTTTTCGCCGCAATAGCGCC
GCGCTTGCAACCTAGGTATTATAGCATCTCCTCCTCCCCGCGTTTCGCGCCGTCTC
GTATCCATGTAACGTGCGCGCTGGTCTATGGTCCTAGCCCTACGGGGCGATTCA
TAAAGGTGTGTGCAGCAACTGGATGAAGAATTCTTTGCCCTCCGAAGAAACCCA
CGATTGCAGCTGGGCACCGGTCTTTGTGCGCCAGTCAAACTTTAAACTGCCCGCC
GATTCGACGACGCCAATCGTGATGGTTGGACCTGGAACCGGCTTCGCTCCATTTC
GCGGCTTCCTTCAGGAACGCGCAAAACTGCAGGAAGCGGGCGAAAAATTGGGCC
CGGCAGTGCTGTTTTTTGGGTGCCGCAACCGCCAGATGGATTACATCTATGAAGA
TGAGCTTAAGGGTTACGTTGAAAAAGGTATTCTGACGAATCTGATCGTTGCATTT
TCACGAGAAGGCGCCACCAAAGAGTATGTTCAGCACAAGATGTTAGAGAAAGCC
```

TABLE 4-continued

Protein and Codon optimized nucleotide sequences.

```
TCCGACACGTGGTCTTTAATCGCCCAGGGTGGTTATCTGTATGTTTGCGGTGATG
CGAAGGGTATGGCCAGAGACGTACATCGCACCCTGCATACAATCGTTCAGGAAC
AAGAATCCGTAGACTCGTCAAAAGCGGAGTTTTTAGTCAAAAAGCTGCAAATGG
ATGGACGCTACTTACGGGATATTTGG
```

REFERENCES

1. Kingston, D. G. The shape of things to come: structural and synthetic studies of taxol and related compounds. Phytochemistry 68, 1844-54 (2007).
2. Wani, M. C., Taylor, H. L., Wall, M. E., Coggon, P. & McPhail, A. T. Plant antitumor agents. VI. The isolation and structure of taxol, a novel antileukemic and antitumor agent from Taxus brevifolia. J Am Chem Soc 93, 2325-7 (1971).
3. Suffness M, W. M. Discovery and developement of taxol. (ed. (ed), S. M.) (CRC Press, Boca Raton, 1995).
4. Nicolaou, K. C. et al. Total synthesis of taxol. Nature 367, 630-4 (1994).
5. Holton, R. A. et al. First total synthesis of taxol. 2. Completion of the C and D rings. Journal of the American Chemical Society 116, 1599-1600 (1994).
6. Walji, A. M. & MacMillan, D. W. C. Strategies to Bypass the Taxol Problem. Enantioselective Cascade Catalysis, a New Approach for the Efficient Construction of Molecular Complexity. Synlett 18, 1477-1489 (2007).
7. Holton RA, B. R., Boatman PD. Semisynthesis of taxol and taxotere (ed. M, S.) (CRC Press, Boca Raton, 1995).
8. Frense, D. Taxanes: perspectives for biotechnological production. Applied microbiology and biotechnology 73, 1233-1240 (2007).
9. Roberts, S. C. Production and engineering of terpenoids in plant cell culture. Nature Chemical Biology 3, 387-395 (2007).
10. Goodman, J. & Walsh, V. The story of taxol: nature and politics in the pursuit of an anti-cancer drug (Cambridge University Press, Cambridge; New York, 2001).
11. Tyo, K. E., Alper, H. S. & Stephanopoulos, G. N. Expanding the metabolic engineering toolbox: more options to engineer cells. Trends Biotechnol 25, 132-7 (2007).
12. Ajikumar, P. K. et al. Terpenoids: opportunities for biosynthesis of natural product drugs using engineered microorganisms. Mol Pharm 5, 167-90 (2008).
13. Jennewein, S. & Croteau, R. Taxol: biosynthesis, molecular genetics, and biotechnological applications. Appl Microbiol Biotechnol 57, 13-9 (2001).
14. Jennewein, S., Wildung, M. R., Chau, M., Walker, K. & Croteau, R. Random sequencing of an induced Taxus cell cDNA library for identification of clones involved in Taxol biosynthesis. Proc Natl Acad Sci USA 101, 9149-54 (2004).
15. Croteau, R., Ketchum, R. E. B., Long, R. M., Kaspera, R. & Wildung, M. R. Taxol biosynthesis and molecular genetics. Phytochemistry Reviews 5, 75-97 (2006).
16. Walker, K. & Croteau, R. Taxol biosynthetic genes. Phytochemistry 58, 1-7 (2001).
17. Dejong, J. M. et al. Genetic engineering of taxol biosynthetic genes in Saccharomyces cerevisiae. Biotechnol Bioeng 93, 212-24 (2006).
18. Engels, B., Dahm, P. & Jennewein, S. Metabolic engineering of taxadiene biosynthesis in yeast as a first step towards Taxol (Paclitaxel) production. Metabolic engineering 10, 201-206 (2008).
19. Chang, M. C. Y. & Keasling, J. D. Production of isoprenoid pharmaceuticals by engineered microbes. Nature chemical biology 2, 674-681 (2006).
20. Khosla, C. & Keasling, J. D. Metabolic engineering for drug discovery and development. Nat Rev Drug Discov 2, 1019-25 (2003).
21. Alper, H., Miyaoku, K. & Stephanopoulos, G. Construction of lycopene-overproducing E. coli strains by combining systematic and combinatorial gene knockout targets. Nat Biotechnol 23, 612-6 (2005).
22. Chang, M. C., Eachus, R. A., Trieu, W., Ro, D. K. & Keasling, J. D. Engineering Escherichia coli for production of functionalized terpenoids using plant P450s. Nat Chem Biol 3, 274-7 (2007).
23. Martin, V. J., Pitera, D. J., Withers, S. T., Newman, J. D. & Keasling, J. D. Engineering a mevalonate pathway in Escherichia coli for production of terpenoids. Nat Biotechnol 21, 796-802 (2003).
24. Huang, Q., Roessner, C. A., Croteau, R. & Scott, A. I. Engineering Escherichia coli for the synthesis of taxadiene, a key intermediate in the biosynthesis of taxol. Bioorg Med Chem 9, 2237-42 (2001).
25. Kim, S. W. & Keasling, J. D. Metabolic engineering of the nonmevalonate isopentenyl diphosphate synthesis pathway in Escherichia coli enhances lycopene production. Biotechnol Bioeng 72, 408-15 (2001).
26. Farmer, W. R. & Liao, J. C. Improving lycopene production in Escherichia coli by engineering metabolic control. Nature Biotechnology 18, 533-537 (2000).
27. Farmer, W. R. & Liao, J. C. Precursor balancing for metabolic engineering of lycopene production in Escherichia coli. Biotechnology progress 17 (2001).
28. Yuan, L. Z., Rouviere, P. E., Larossa, R. A. & Suh, W. Chromosomal promoter replacement of the isoprenoid pathway for enhancing carotenoid production in E. coli. Metab Eng 8, 79-90 (2006).
29. Jin, Y. S. & Stephanopoulos, G. Multi-dimensional gene target search for improving lycopene biosynthesis in Escherichia coli. Metabolic Engineering 9, 337-347 (2007).
30. Wang, H. H. et al. Programming cells by multiplex genome engineering and accelerated evolution. Nature (2009).
31. Klein-Marcuschamer, D., Ajikumar, P. K. & Stephanopoulos, G. Engineering microbial cell factories for biosynthesis of isoprenoid molecules: beyond lycopene. Trends in Biotechnology 25, 417-424 (2007).
32. Sandmann, G. Combinatorial biosynthesis of carotenoids in a heterologous host: a powerful approach for the biosynthesis of novel structures. ChemBioChem 3 (2002).
33. Brosius, J., Erfle, M. & Storella, J. Spacing of the −10 and −35 regions in the tac promoter. Effect on its in vivo activity. J Biol Chem 260, 3539-41 (1985).
34. Brunner, M. & Bujard, H. Promoter recognition and promoter strength in the Escherichia coli system. Embo J 6, 3139-44 (1987).

35. Nishizaki, T., Tsuge, K., Itaya, M., Doi, N. & Yanagawa, H. Metabolic engineering of carotenoid biosynthesis in *Escherichia coli* by ordered gene assembly in *Bacillus subtilis*. Appl Environ Microbiol 73, 1355-61 (2007).
36. Sorensen, H. P. & Mortensen, K. K. Advanced genetic strategies for recombinant protein expression in *Escherichia coli*. J Biotechnol 115, 113-28 (2005).
37. Jones, K. L., Kim, S. W. & Keasling, J. D. Low-copy plasmids can perform as well as or better than high-copy plasmids for metabolic engineering of bacteria. Metab Eng 2, 328-38 (2000).
38. Hoffmann, F. & Rinas, U. Stress induced by recombinant protein production in *Escherichia coli*. Advances in Biochemical Engineering Biotechnology 89, 73-92 (2005).
39. Hoffmann, F., Weber, J. & Rinas, U. Metabolic adaptation of *Escherichia coli* during temperature-induced recombinant protein production: 1. Readjustment of metabolic enzyme synthesis. Biotechnology and bioengineering 80 (2002).
40. Chang, D. E., Smalley, D. J. & Conway, T. Gene expression profiling of *Escherichia coli* growth transitions: an expanded stringent response model. Molecular microbiology 45, 289-306 (2002).
41. Kaspera, R. & Croteau, R. Cytochrome P450 oxygenases of Taxol biosynthesis. Phytochemistry Reviews 5, 433-444 (2006).
42. Jennewein, S., Long, R. M., Williams, R. M. & Croteau, R. Cytochrome p450 taxadiene 5alpha-hydroxylase, a mechanistically unusual monooxygenase catalyzing the first oxygenation step of taxol biosynthesis. Chem Biol 11, 379-87 (2004).
43. Schuler, M. A. & Werck-Reichhart, D. F UNCTIONAL G ENOMICS OF P450 S. Annual Review of Plant Biology 54, 629-667 (2003).
44. Leonard, E. & Koffas, M. A. G. Engineering of artificial plant cytochrome P450 enzymes for synthesis of isoflavones by *Escherichia coli*. Applied and Environmental Microbiology 73, 7246 (2007).
45. Nelson, D. R. Cytochrome P450 and the individuality of species. Archives of Biochemistry and Biophysics 369, 1-10 (1999).
46. Jennewein, S. et al. Coexpression in yeast of Taxus cytochrome P450 reductase with cytochrome P450 oxygenases involved in Taxol biosynthesis. Biotechnol Bioeng 89, 588-98 (2005).
47. Rontein, D. et al. CYP725A4 from yew catalyzes complex structural rearrangement of taxa-4(5),11(12)-diene into the cyclic ether 5(12)-oxa-3(11)-cyclotaxane. J Biol Chem 283, 6067-75 (2008).
48. Shigemori, H. & Kobayashi, J. Biological activity and chemistry of taxoids from the Japanese yew, Taxus cuspidata. J Nat Prod 67, 245-56 (2004).
49. Xu, F., Tao, W., Cheng, L. & Guo, L. Strain improvement and optimization of the media of taxol-producing fungus Fusarium maire. Biochemical Engineering Journal 31, 67-73 (2006).
50. Hefner, J., Ketchum, R. E. & Croteau, R. Cloning and functional expression of a cDNA encoding geranylgeranyl diphosphate synthase from Taxus canadensis and assessment of the role of this prenyltransferase in cells induced for taxol production. Arch Biochem Biophys 360, 62-74 (1998).
51. Wildung, M. R. & Croteau, R. A cDNA clone for taxadiene synthase, the diterpene cyclase that catalyzes the committed step of taxol biosynthesis. J Biol Chem 271, 9201-4 (1996).
52. Kodumal, S. J. et al. Total synthesis of long DNA sequences: synthesis of a contiguous 32-kb polyketide synthase gene cluster. Proceedings of the National Academy of Sciences 101, 15573-15578 (2004).
53. Tyo, K. E. J., Ajikumar, P. K. & Stephanopoulos, G. Stabilized gene duplication enables long-term selection-free heterologous pathway expression. Nature Biotechnology (2009).
54. Datsenko, K. A. & Wanner, B. L. 6640-6645 (National Acad Sciences, 2000).
55. Rost, B., Yachdav, G. & Liu, J. The predictprotein server. Nucleic acids research 32, W321 (2004).
56. Shalel-Levanon, S., San, K. Y. & Bennett, G. N. Effect of ArcA and FNR on the expression of genes related to the oxygen regulation and the glycolysis pathway in *Escherichia coli* under microaerobic growth conditions. Biotechnology and bioengineering 92 (2005).
57. Heinig, U. & Jennewein, S. Taxol: A complex diterpenoid natural product with an evolutionarily obscure origin. African Journal of Biotechnology 8, 1370-1385 (2009).
58. Walji, A. M. & MacMillan, D. W. C. Strategies to Bypass the Taxol Problem. Enantioselective Cascade Catalysis, a New Approach for the Efficient Construction of Molecular Complexity. Synlett 18, 1477-1489 (2007).
59. Chau, M., Jennewein, S., Walker, K. & Croteau, R. Taxol biosynthesis: Molecular cloning and characterization of a cytochrome P450 taxoid 7 beta-hydroxylase. Chem Biol 11, 663-72 (2004).
60. Williams, D. C. et al. Heterologous expression and characterization of a "Pseudomature" form of taxadiene synthase involved in paclitaxel (Taxol) biosynthesis and evaluation of a potential intermediate and inhibitors of the multistep diterpene cyclization reaction. Arch Biochem Biophys 379, 137-46 (2000).
61. Morrone D. et al. Increasing diterpene yield with a modular metabolic engineering system in *E. coli*: comparison of MEV and MEP isoprenoid precursor pathway engineering. Appl Microbiol Biotechnol. 85(6):1893-906 (2010)

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the specific purpose mentioned herein.

What is claimed is:

1. A method for making a product containing patchouli alcohol, or derivative thereof, the method comprising:
providing an *Escherichia coli* (*E. coli*) that produces isopentyl pyrophosphate (IPP) and dimethylallyl pyrophosphate (DMAPP) through an upstream methylerythritol pathway (MEP) and converts the IPP and DMAPP to patchouli alcohol through a recombinantly expressed downstream synthesis pathway comprising farnesyl diphosphate synthase and patchoulol synthase; and
culturing the *E. coli* to produce the patchouli alcohol, or derivative thereof, wherein the accumulation of indole in the culture is controlled to below 100 mg/L to thereby increase production of patchouli alcohol or derivative; and incorporating the patchouli alcohol, or derivative thereof, into a product.

2. The method of claim 1, wherein the product is a fragrance product, a cosmetic, a cleaning product, or a soap.

3. The method of claim 1, wherein the product is an insecticide, pesticide, or pest control agent.

4. The method of claim 1, wherein accumulation of indole in the culture is controlled by balancing the upstream MEP pathway with the downstream terpenoid synthesis pathway.

5. The method of claim 1, further comprising measuring the amount or concentration of indole continuously or intermittently.

6. The method of claim 1, wherein accumulation of indole in the culture is maintained to below 50 mg/L.

7. The method of claim 1, wherein accumulation of indole in the culture is maintained to below 10 mg/L.

8. The method of claim 1, wherein the patchouli alcohol or derivative is produced at 10 mg/L or more.

9. The method of claim 1, wherein the patchouli alcohol or derivative is produced at 100 mg/L or more.

10. The method of claim 1, wherein the *E. coli* has additional copies of one or more of the dxs, idi, ispD, and ispF genes of the MEP pathway.

11. The method of claim 10, wherein the *E. coli* has a heterologous dxs-idi-ispDF operon.

12. The method of claim 1, wherein the *E. coli* further expresses a P450 enzyme.

13. A method for making patchouli alcohol, or derivative thereof, the method comprising:
providing an *Escherichia coli* (*E. coli*) that produces isopentyl pyrophosphate (IPP) and dimethylallyl pyrophosphate (DMAPP) through an upstream methylerythritol pathway (MEP) and converts the IPP and DMAPP to patchouli alcohol or derivative through a recombinantly expressed downstream synthesis pathway comprising farnesyl diphosphate synthase and patchoulol synthase; and
culturing the *E. coli* to produce the patchouli alcohol, or derivative thereof, wherein the accumulation of indole in the culture is controlled to below 100 mg/L to thereby increase terpenoid production; and recovering the patchouli alcohol, or derivative thereof.

14. The method of claim 13, wherein accumulation of indole in the culture is controlled by balancing the upstream MEP pathway with the downstream terpenoid synthesis pathway.

15. The method of claim 13, further comprising, measuring the amount or concentration of indole continuously or intermittently.

16. The method of claim 13, wherein accumulation of indole in the culture is maintained to below 50 mg/L.

17. The method of claim 13, wherein accumulation of indole in the culture is maintained to below 10 mg/L.

18. The method of claim 13, wherein the patchouli alcohol or derivative is produced at 10 mg/L or more.

19. The method of claim 13, wherein the patchouli alcohol or derivative is produced at 100 mg/L or more.

20. The method of claim 13, wherein the *E. coli* has additional copies of one or more of the dxs, idi, ispD and ispF genes of the MEP pathway.

21. The method of claim 13, wherein the *E. coli* has a heterologous dxs-idi-ispDF operon.

22. The method of claim 13, wherein the *E. coli* further expresses a P450 enzyme.

* * * * *

SEQUENCE LISTING

<160> NUMBER OF SEQ ID NOS: 52

<210> SEQ ID NO 1
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 1
cggcatatga gttttgatat tgccaaatac ccg                33

<210> SEQ ID NO 2
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 2
cggctagctt atgccagcca ggccttgatt ttg                33

<210> SEQ ID NO 3
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 3
cgcggctagc gaaggagata tacatatgca aacggaacac gtcattttat tg                52

<210> SEQ ID NO 4
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 4
cggaattcgc tcacaacccc ggcaaatgtc gg                32

<210> SEQ ID NO 5
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 5
gcgaattcga aggagatata catatggcaa ccactcattt ggatgtttg                49

<210> SEQ ID NO 6
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 6
gcgctcgagt cattttgttg ccttaatgag tagcgcc                37

<210> SEQ ID NO 7
<211> LENGTH: 33
<212> TYPE: DNA
<213> ORGANISM: Artificial Sequence

```
<220> FEATURE:
<223> OTHER INFORMATION: Synthetic Oligonucleotide

<400> SEQUENCE: 7
taaaccatgg gttttgatat tgccaaatac ccg                          33

<210> SEQ ID NO 8
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 8
cggggtacct cattttgttg ccttaatgag tagcgc                       36

<210> SEQ ID NO 9
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 9
cggctcgagt cattttgttg ccttaatgag tagcgc                       36

<210> SEQ ID NO 10
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 10
cgtaaccggt gcctctgcta accatgttca tgccttc                      37

<210> SEQ ID NO 11
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 11
ctccttcgct agcttatgcc agcc                                    24

<210> SEQ ID NO 12
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 12
cgtagaattc actcacaact gacgaaacgc aatgtaatc                    39

<210> SEQ ID NO 13
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 13
cgtagaattc agaaggagat atacatatgg ctagctctac gggtacg           47
```

<210> SEQ ID NO 14
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 14
gatggtcgac ttagacctgg attggatcga tgtaaac                    37

<210> SEQ ID NO 15
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 15
cgtaccatgg ctagctctac gggtacg                               27

<210> SEQ ID NO 16
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 16
cgtagaattc ttagacctgg attggatcga tgtaaac                    37

<210> SEQ ID NO 17
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 17
cgtagaattc agaaggagat atacatatgt ttgatttcaa tgaatatatg aaaagtaagg    60
c                                                                  61

<210> SEQ ID NO 18
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 18
gatggtcgac tcacaactga cgaaacgcaa tgtaatc                    37

<210> SEQ ID NO 19
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 19
gatgctcgag ttagacctgg attggatcga tgtaaac                    37

<210> SEQ ID NO 20
<211> LENGTH: 25
<212> TYPE: DNA
<213> ORGANISM: Artificial Sequence

```
<220> FEATURE:
<223> OTHER INFORMATION: Synthetic Oligonucleotide

<400> SEQUENCE: 20
gccgtcgacc atcatcatca tcatc                                          25

<210> SEQ ID NO 21
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 21
gcagtctaga gccagaaccg ttatgatgtc ggcgc                               35

<210> SEQ ID NO 22
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 22
cgtgtccgga gcatctaacg cttgagttaa gccgc                               35

<210> SEQ ID NO 23
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 23
gcagtctaga ggaaacctgt cgtgccagct gc                                  32

<210> SEQ ID NO 24
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 24
gacgctcgag gagcaataac tagcataacc ccttggggcc tctaaacggg tcttgagggg    60 tttttttgctt gtgtaggctg gagctgcttc g                                  91

<210> SEQ ID NO 25
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 25
gacgagtact gaacgtcgga attgatccgt cgac                                34

<210> SEQ ID NO 26
<211> LENGTH: 91
<212> TYPE: DNA
<213> ORGANISM: Artificial Sequence
<220> FEATURE:
<223> OTHER INFORMATION: Synthetic Oligonucleotide

<400> SEQUENCE: 26
```
gacggagctc gagcaataac tagcataacc ccttggggcc tctaaacggg tcttgagggg    60 tttttttgctt gtgtaggctg gagctgcttc g                                 91

<210> SEQ ID NO 27
<211> LENGTH: 63
<212> TYPE: DNA
<213> ORGANISM: Artificial Sequence
<220> FEATURE:
<223> OTHER INFORMATION: Synthetic Oligonucleotide

<400> SEQUENCE: 27
atgacgattt ttgataatta tgaagtgtgg tttgtcattg cattaattgc gttgcgctca    60
ctg                                                                 63

<210> SEQ ID NO 28
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 28
atgacgattt ttgataatta tgaagtgtgg tttgtcattg gcatccgctt acagacaagc    60
tgtg                                                                64

<210> SEQ ID NO 29
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 29
ttagcgacga aacccgtaat acacttcgtt ccagcgcagc cgacgtcgga attgatccgt    60
cgac                                                                64

<210> SEQ ID NO 30
<211> LENGTH: 59
<212> TYPE: DNA
<213> ORGANISM: Artificial Sequence
<220> FEATURE:
<223> OTHER INFORMATION: Synthetic Oligonucleotide

<400> SEQUENCE: 30
cgtacatatg gctctgttat tagcagtttt tgtggcgaaa tttaacgaag taacccagc    59

<210> SEQ ID NO 31
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 31
cgtacatatg gctctgttat tagcagtttt ttttagcatc gctttgagtg caattg        56

<210> SEQ ID NO 32
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 32
cgtacatatg gctctgttat tagcagtttt ttttcgctcg aaacgtcata gtagcctg     58

<210> SEQ ID NO 33
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 33
cgcgggatcc ggtgctgccc ggacgaggga acagtttgat tgaaaaccc     49

<210> SEQ ID NO 34
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 34
cgcgggatcc cgccgtggtg aagtgatac acag     34

<210> SEQ ID NO 35
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 35
cgcggtcgac ttaccaaata tcccgtaagt agcgtccatc     40

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
attcaaaagc ttccggtcct     20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
atctggcgac attcgttttc     20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
gacgaactgt cacccgattt     20

<210> SEQ ID NO 39
<211> LENGTH: 20
<212> TYPE: DNA

<213> ORGANISM: Artificial Sequence
<220> FEATURE:
<223> OTHER INFORMATION: Synthetic Oligonucleotide

<400> SEQUENCE: 39
gcttcgcggg tagtagacag                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
aggccttcgg gttgtaaagt                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
attccgatta acgcttgcac                                              20

<210> SEQ ID NO 42
<211> LENGTH: 296
<212> TYPE: PRT
<213> ORGANISM: Artificial Sequence
<220> FEATURE:
<223> OTHER INFORMATION: Synthetic Polypeptide

<400> SEQUENCE: 42

Met Phe Asp Phe Asn Glu Tyr Met Lys Ser Lys Ala Val Ala Val Asp
1               5                   10                  15

Ala Ala Leu Asp Lys Ala Ile Pro Leu Glu Tyr Pro Glu Lys Ile His
            20                  25                  30

Glu Ser Met Arg Tyr Ser Leu Leu Ala Gly Gly Lys Arg Val Arg Pro
        35                  40                  45

Ala Leu Cys Ile Ala Ala Cys Glu Leu Val Gly Gly Ser Gln Asp Leu
    50                  55                  60

Ala Met Pro Thr Ala Cys Ala Met Glu Met Ile His Thr Met Ser Leu
65                  70                  75                  80

Ile His Asp Asp Leu Pro Cys Met Asp Asn Asp Asp Phe Arg Arg Gly
                85                  90                  95

Lys Pro Thr Asn His Lys Val Phe Gly Glu Asp Thr Ala Val Leu Ala
            100                 105                 110

Gly Asp Ala Leu Leu Ser Phe Ala Phe Glu His Ile Ala Val Ala Thr
        115                 120                 125

Ser Lys Thr Val Pro Ser Asp Arg Thr Leu Arg Val Ile Ser Glu Leu
    130                 135                 140

Gly Lys Thr Ile Gly Ser Gln Gly Leu Val Gly Gly Gln Val Val Asp
145                 150                 155                 160

Ile Thr Ser Glu Gly Asp Ala Asn Val Asp Leu Lys Thr Leu Glu Trp
                165                 170                 175

Ile His Ile His Lys Thr Ala Val Leu Leu Glu Cys Ser Val Val Ser
            180                 185                 190

Gly Gly Ile Leu Gly Gly Ala Thr Glu Asp Glu Ile Ala Arg Ile Arg

```
                195                 200                 205
Arg Tyr Ala Arg Cys Val Gly Leu Leu Phe Gln Val Val Asp Asp Ile
    210                 215                 220

Leu Asp Val Thr Lys Ser Ser Glu Glu Leu Gly Lys Thr Ala Gly Lys
225                 230                 235                 240

Asp Leu Leu Thr Asp Lys Ala Thr Tyr Pro Lys Leu Met Gly Leu Glu
                245                 250                 255

Lys Ala Lys Glu Phe Ala Ala Glu Leu Ala Thr Arg Ala Lys Glu Glu
                260                 265                 270

Leu Ser Ser Phe Asp Gln Ile Lys Ala Ala Pro Leu Leu Gly Leu Ala
                275                 280                 285

Asp Tyr Ile Ala Phe Arg Gln Asn
                290                 295

<210> SEQ ID NO 43
<211> LENGTH: 888
<212> TYPE: DNA
<213> ORGANISM: Artificial Sequence
<220> FEATURE:
<223> OTHER INFORMATION: Synthetic Polynucleotide

<400> SEQUENCE: 43
atgtttgatt tcaatgaata tatgaaaagt aaggctgttg cggtagacgc ggctctggat       60
aaagcgattc cgctggaata tcccgagaag attcacgaat cgatgcgcta ctccctgtta      120
gcaggaggga aacgcgttcg tccggcatta tgcatcgcgg cctgtgaact cgtcggcggt      180
tcacaggact tagcaatgcc aactgcttgc gcaatggaaa tgattcacac aatgagcctg      240
attcatgatg atttgccttg catggacaac gatgactttc ggcgcggtaa acctactaat      300
cataaggttt ttggcgaaga tactgcagtg ctggcgggcg atgcgctgct gtcgtttgcc      360
ttcgaacata tcgccgtcgc gacctcgaaa accgtcccgt cggaccgtac gcttcgcgtg      420
atttccgagc tgggaaagac catcggctct caaggactcg tgggtggtca ggtagttgat      480
atcacgtctg agggtgacgc gaacgtggac ctgaaaaccc tggagtggat ccatattcac      540
aaaacggccg tgctgctgga atgtagcgtg gtgtcagggg ggatcttggg gggcgccacg      600
gaggatgaaa tcgcgcgtat tcgtcgttat gcccgctgtg ttggactgtt atttcaggtg      660
gtggatgaca tcctggatgt cacaaaaatc cagcgaagagc ttggcaagac gcgggcaaa      720 gaccttctga cggataaggc tacatacccg aaattgatgg gcttggagaa agccaaggag      780
ttcgcagctg aacttgccac gcgggcgaag gaagaactct cttctttcga tcaaatcaaa      840
gccgcgccac tgctgggcct cgccgattac attgcgtttc gtcagaac               888

<210> SEQ ID NO 44
<211> LENGTH: 802
<212> TYPE: PRT
<213> ORGANISM: Artificial Sequence
<220> FEATURE:
<223> OTHER INFORMATION: Synthetic Polypeptide

<400> SEQUENCE: 44

Met Ser Ser Ser Thr Gly Thr Ser Lys Val Val Ser Glu Thr Ser Ser
1               5                   10                  15

Thr Ile Val Asp Asp Ile Pro Arg Leu Ser Ala Asn Tyr His Gly Asp
                20                  25                  30

Leu Trp His His Asn Val Ile Gln Thr Leu Glu Thr Pro Phe Arg Glu
                35                  40                  45
```

-continued

```
Ser Ser Thr Tyr Gln Glu Arg Ala Asp Glu Leu Val Lys Ile Lys
    50                  55                  60
Asp Met Phe Asn Ala Leu Gly Asp Gly Asp Ile Ser Pro Ser Ala Tyr
 65                  70                  75                  80
Asp Thr Ala Trp Val Ala Arg Leu Ala Thr Ile Ser Ser Asp Gly Ser
                 85                  90                  95
Glu Lys Pro Arg Phe Pro Gln Ala Leu Asn Trp Val Phe Asn Asn Gln
            100                 105                 110
Leu Gln Asp Gly Ser Trp Gly Ile Glu Ser His Phe Ser Leu Cys Asp
        115                 120                 125
Arg Leu Leu Asn Thr Thr Asn Ser Val Ile Ala Leu Ser Val Trp Lys
130                 135                 140
Thr Gly His Ser Gln Val Gln Gln Gly Ala Glu Phe Ile Ala Glu Asn
145                 150                 155                 160
Leu Arg Leu Leu Asn Glu Glu Asp Glu Leu Ser Pro Asp Phe Gln Ile
                165                 170                 175
Ile Phe Pro Ala Leu Leu Gln Lys Ala Lys Ala Leu Gly Ile Asn Leu
            180                 185                 190
Pro Tyr Asp Leu Pro Phe Ile Lys Tyr Leu Ser Thr Thr Arg Glu Ala
        195                 200                 205
Arg Leu Thr Asp Val Ser Ala Ala Asp Asn Ile Pro Ala Asn Met
210                 215                 220
Leu Asn Ala Leu Glu Gly Leu Glu Glu Val Ile Asp Trp Asn Lys Ile
225                 230                 235                 240
Met Arg Phe Gln Ser Lys Asp Gly Ser Phe Leu Ser Ser Pro Ala Ser
                245                 250                 255
Thr Ala Cys Val Leu Met Asn Thr Gly Asp Glu Lys Cys Phe Thr Phe
            260                 265                 270
Leu Asn Asn Leu Leu Asp Lys Phe Gly Gly Cys Val Pro Cys Met Tyr
        275                 280                 285
Ser Ile Asp Leu Leu Glu Arg Leu Ser Leu Val Asp Asn Ile Glu His
    290                 295                 300
Leu Gly Ile Gly Arg His Phe Lys Gln Glu Ile Lys Gly Ala Leu Asp
305                 310                 315                 320
Tyr Val Tyr Arg His Trp Ser Glu Arg Gly Ile Gly Trp Gly Arg Asp
                325                 330                 335
Ser Leu Val Pro Asp Leu Asn Thr Thr Ala Leu Gly Leu Arg Thr Leu
            340                 345                 350
Arg Met His Gly Tyr Asn Val Ser Ser Asp Val Leu Asn Asn Phe Lys
        355                 360                 365
Asp Glu Asn Gly Arg Phe Phe Ser Ser Ala Gly Gln Thr His Val Glu
    370                 375                 380
Leu Arg Ser Val Val Asn Leu Phe Arg Ala Ser Asp Leu Ala Phe Pro
385                 390                 395                 400
Asp Glu Arg Ala Met Asp Asp Ala Arg Lys Phe Ala Glu Pro Tyr Leu
                405                 410                 415
Arg Glu Ala Leu Ala Thr Lys Ile Ser Thr Asn Thr Lys Leu Phe Lys
            420                 425                 430
Glu Ile Glu Tyr Val Val Glu Tyr Pro Trp His Met Ser Ile Pro Arg
        435                 440                 445
Leu Glu Ala Arg Ser Tyr Ile Asp Ser Tyr Asp Asp Asn Tyr Val Trp
    450                 455                 460
Gln Arg Lys Thr Leu Tyr Arg Met Pro Ser Leu Ser Asn Ser Lys Cys
```

| | | | | | | | | | | | | | | |
|---|---|---|---|---|---|---|---|---|---|---|---|---|---|---|
| | 465 | | | | 470 | | | | 475 | | | | 480 | |
| Leu | Glu | Leu | Ala | Lys | Leu | Asp | Phe | Asn | Ile | Val | Gln | Ser | Leu | His | Gln |
| | | | | 485 | | | | | 490 | | | | | 495 | |
| Glu | Glu | Leu | Lys | Leu | Leu | Thr | Arg | Trp | Trp | Lys | Glu | Ser | Gly | Met | Ala |
| | | | 500 | | | | | 505 | | | | | 510 | | |
| Asp | Ile | Asn | Phe | Thr | Arg | His | Arg | Val | Ala | Glu | Val | Tyr | Phe | Ser | Ser |
| | | 515 | | | | | 520 | | | | | 525 | | | |
| Ala | Thr | Phe | Glu | Pro | Glu | Tyr | Ser | Ala | Thr | Arg | Ile | Ala | Phe | Thr | Lys |
| | 530 | | | | | 535 | | | | | 540 | | | | |
| Ile | Gly | Cys | Leu | Gln | Val | Leu | Phe | Asp | Asp | Met | Ala | Asp | Ile | Phe | Ala |
| 545 | | | | | 550 | | | | | 555 | | | | | 560 |
| Thr | Leu | Asp | Glu | Leu | Lys | Ser | Phe | Thr | Glu | Gly | Val | Lys | Arg | Trp | Asp |
| | | | | 565 | | | | | 570 | | | | | 575 | |
| Thr | Ser | Leu | Leu | His | Glu | Ile | Pro | Glu | Cys | Met | Gln | Thr | Cys | Phe | Lys |
| | | | 580 | | | | | 585 | | | | | 590 | | |
| Val | Trp | Phe | Lys | Leu | Met | Glu | Glu | Val | Asn | Asn | Asp | Val | Val | Lys | Val |
| | | 595 | | | | | 600 | | | | | 605 | | | |
| Gln | Gly | Arg | Asp | Met | Leu | Ala | His | Ile | Arg | Lys | Pro | Trp | Glu | Leu | Tyr |
| | 610 | | | | | 615 | | | | | 620 | | | | |
| Phe | Asn | Cys | Tyr | Val | Gln | Glu | Arg | Glu | Trp | Leu | Glu | Ala | Gly | Tyr | Ile |
| 625 | | | | | 630 | | | | | 635 | | | | | 640 |
| Pro | Thr | Phe | Glu | Glu | Tyr | Leu | Lys | Thr | Tyr | Ala | Ile | Ser | Val | Gly | Leu |
| | | | | 645 | | | | | 650 | | | | | 655 | |
| Gly | Pro | Cys | Thr | Leu | Gln | Pro | Ile | Leu | Leu | Met | Gly | Glu | Leu | Val | Lys |
| | | | 660 | | | | | 665 | | | | | 670 | | |
| Asp | Asp | Val | Val | Glu | Lys | Val | His | Tyr | Pro | Ser | Asn | Met | Phe | Glu | Leu |
| | | 675 | | | | | 680 | | | | | 685 | | | |
| Val | Ser | Leu | Ser | Trp | Arg | Leu | Thr | Asn | Asp | Thr | Lys | Thr | Tyr | Gln | Ala |
| | 690 | | | | | 695 | | | | | 700 | | | | |
| Glu | Lys | Ala | Arg | Gly | Gln | Gln | Ala | Ser | Gly | Ile | Ala | Cys | Tyr | Met | Lys |
| 705 | | | | | 710 | | | | | 715 | | | | | 720 |
| Asp | Asn | Pro | Gly | Ala | Thr | Glu | Glu | Asp | Ala | Ile | Lys | His | Ile | Cys | Arg |
| | | | | 725 | | | | | 730 | | | | | 735 | |
| Val | Val | Asp | Arg | Ala | Leu | Lys | Glu | Ala | Ser | Phe | Glu | Tyr | Phe | Lys | Pro |
| | | | 740 | | | | | 745 | | | | | 750 | | |
| Ser | Asn | Asp | Ile | Pro | Met | Gly | Cys | Lys | Ser | Phe | Ile | Phe | Asn | Leu | Arg |
| | | 755 | | | | | 760 | | | | | 765 | | | |
| Leu | Cys | Val | Gln | Ile | Phe | Tyr | Lys | Phe | Ile | Asp | Gly | Tyr | Gly | Ile | Ala |
| | 770 | | | | | 775 | | | | | 780 | | | | |
| Asn | Glu | Glu | Ile | Lys | Asp | Tyr | Ile | Arg | Lys | Val | Tyr | Ile | Asp | Pro | Ile |
| 785 | | | | | 790 | | | | | 795 | | | | | 800 |
| Gln | Val | | | | | | | | | | | | | | |

<210> SEQ ID NO 45
<211> LENGTH: 2406
<212> TYPE: DNA
<213> ORGANISM: Artificial Sequence
<220> FEATURE:
<223> OTHER INFORMATION: Synthetic Polynucleotide

<400> SEQUENCE: 45

```
atgtctagct ctacgggtac gtctaaagtc gtgagtgaaa cctcatcgac gatcgtggac      60
gatattccac gcttgtcggc gaactatcat ggagatctgt ggcatcataa cgtcattcag     120
acattggaaa ccccgtttcg cgaaagtagc acctaccagg aacgggcaga tgaattagtc     180
```

```
gtgaaaatca aagatatgtt taatgcatta ggagatggag acatctcgcc cagcgcatat    240
gatacggcgt gggtggctcg gttggccacg attagctccg atggcagtga aaagccgcgt    300
ttcccgcagg cgctgaactg ggtgtttaat aatcaattgc aggatggcag ctggggcatt    360
gaatctcact ttagcctctg tgaccggtta ctcaacacga caaactccgt aattgcgttg    420
tcagtttgga aaacgggcca tagccaggtt caacagggcg cggaatttat cgctgaaaat    480
ctgcgcctgc tgaacgagga ggacgaactg tcacccgatt ttcagattat ttttccggct    540
ttactccaga aagccaaagc cttaggcatc aacctgccat atgatctgcc gttcatcaag    600
tatctgtcta ctacccgcga agcccgtctc actgacgtct ctgcggcggc ggacaatatt    660
ccagcgaaca tgctgaacgc actggaaggg ctggaagagg ttatcgactg gaataaaatc    720
atgcgcttcc aaagcaagga cggtagcttc ttaagcagcc cagcatctac tgcttgtgtt    780
ctgatgaata ccggagacga aaagtgcttt acgtttctga caatctgct ggacaaattt    840 gggggttgtg ttccttgtat gtattccatt gatctgttgg aacgtctgtc gctggtcgat    900
aacattgaac acttaggtat cggccgccac ttcaaacaag aaatcaaggg ggcgttggat    960
tatgtatacc gtcattggag cgagcgtggt attggttggg ggcgcgatag cttggtacct   1020
gatctgaaca ccactgcttt gggactgcgc actcttcgta tgcacggata caacgttagt   1080
tccgatgtcc tcaataattt caaggacgag aacggccgtt ttttcagctc ggccggtcag   1140
acgcatgttg aactgcggtc cgtagtcaat ctctttcgcg ctagtgatct ggccttcccc   1200
gacgagcgcg ctatggacga tgcacggaag tttgccgagc cgtatctccg cgaagccctg   1260
gccaccaaaa tttcaaccaa caccaagctt ttcaaagaaa ttgagtatgt agtagagtat   1320
ccgtggcata tgtctattcc gcgcctggaa gcccgctcgt atatcgattc ttacgatgac   1380
aattatgtgt ggcaacgcaa aacactgtac cgtatgccca gcctgtcaaa tagtaagtgt   1440
ctggagctgg cgaaactgga tttcaacatt gtgcaatccc tgcaccaaga agagctgaaa   1500
ttactgactc gctggtggaa ggaatccggc atggcagaca tcaatttac gcgtcaccgt   1560 gttgcagagg tgtacttctc ctcggcgacc tttgagccgg agtattcggc cacacgtatt   1620
gcatttacca agattggctg ccttcaggtg ctttttgacg atatggcgga tattttttgcg   1680 acacttgatg agcttaaatc atttaccgaa ggcgtgaagc gttgggatac ctctctgttg   1740
catgaaatcc ccgaatgtat gcagacctgc ttcaaagttt ggttcaaact gatggaagaa   1800
gtgaacaacg acgtcgtgaa agttcagggt cgtgatatgt tagcacacat ccgcaagccg   1860
tgggaactct atttcaattg ctatgtgcag gagcgtgaat ggttagaagc gggctacatt   1920
cctaccttcg aagagtactt aaaaacctat gccatttccg tcggtttagg cccgtgcact   1980
ctgcagccta tcttgctgat gggtgagctg gtaaaggatg atgtggtgga aaagttcac    2040 tacccgtcga atatgtttga actggtaagt ctgagttggc gtctgacaaa cgacaccaaa   2100
acgtaccagc agaaaaggc acgtgggcaa caggcaagcg gtatcgcgtg ttatatgaag   2160
gataatccgg gcgctactga ggaagatgcc attaagcata tctgccgtgt tgtggatcgc   2220
gctcttaaag aagcgtcatt cgaatatttt aaacctagta atgatattcc gatgggttgt   2280
aagtcattca ttttcaatct tcgcctgtgc gtgcaaattt tttacaaatt tattgacggc   2340
tacggaatcg ccaacgaaga aatcaaagac tatattcgta aagtttacat cgatccaatc   2400
caggtc                                                              2406
```

<210> SEQ ID NO 46

<211> LENGTH: 499
<212> TYPE: PRT
<213> ORGANISM: Artificial Sequence
<220> FEATURE:
<223> OTHER INFORMATION: Synthetic Polypeptide

<400> SEQUENCE: 46

```
Met Asp Ala Leu Tyr Lys Ser Thr Val Ala Lys Phe Asn Glu Val Thr
1               5                   10                  15

Gln Leu Asp Cys Ser Thr Glu Ser Phe Ser Ile Ala Leu Ser Ala Ile
            20                  25                  30

Ala Gly Ile Leu Leu Leu Leu Leu Phe Arg Ser Lys Arg His Ser
        35                  40                  45

Ser Leu Lys Leu Pro Pro Gly Lys Leu Gly Ile Pro Phe Ile Gly Glu
    50                  55                  60

Ser Phe Ile Phe Leu Arg Ala Leu Arg Ser Asn Ser Leu Glu Gln Phe
65                  70                  75                  80

Phe Asp Glu Arg Val Lys Lys Phe Gly Leu Val Phe Lys Thr Ser Leu
                85                  90                  95

Ile Gly His Pro Thr Val Val Leu Cys Gly Pro Ala Gly Asn Arg Leu
            100                 105                 110

Ile Leu Ser Asn Glu Glu Lys Leu Val Gln Met Ser Trp Pro Ala Gln
        115                 120                 125

Phe Met Lys Leu Met Gly Glu Asn Ser Val Ala Thr Arg Arg Gly Glu
    130                 135                 140

Asp His Ile Val Met Arg Ser Ala Leu Ala Gly Phe Phe Gly Pro Gly
145                 150                 155                 160

Ala Leu Gln Ser Tyr Ile Gly Lys Met Asn Thr Glu Ile Gln Ser His
                165                 170                 175

Ile Asn Glu Lys Trp Lys Gly Lys Asp Glu Val Asn Val Leu Pro Leu
            180                 185                 190

Val Arg Glu Leu Val Phe Asn Ile Ser Ala Ile Leu Phe Phe Asn Ile
        195                 200                 205

Tyr Asp Lys Gln Glu Gln Asp Arg Leu His Lys Leu Leu Glu Thr Ile
    210                 215                 220

Leu Val Gly Ser Phe Ala Leu Pro Ile Asp Leu Pro Gly Phe Gly Phe
225                 230                 235                 240

His Arg Ala Leu Gln Gly Arg Ala Lys Leu Asn Lys Ile Met Leu Ser
                245                 250                 255

Leu Ile Lys Lys Arg Lys Glu Asp Leu Gln Ser Gly Ser Ala Thr Ala
            260                 265                 270

Thr Gln Asp Leu Leu Ser Val Leu Leu Thr Phe Arg Asp Asp Lys Gly
        275                 280                 285

Thr Pro Leu Thr Asn Asp Glu Ile Leu Asp Asn Phe Ser Ser Leu Leu
    290                 295                 300

His Ala Ser Tyr Asp Thr Thr Thr Ser Pro Met Ala Leu Ile Phe Lys
305                 310                 315                 320

Leu Leu Ser Ser Asn Pro Glu Cys Tyr Gln Lys Val Val Gln Glu Gln
                325                 330                 335

Leu Glu Ile Leu Ser Asn Lys Glu Glu Gly Glu Glu Ile Thr Trp Lys
            340                 345                 350

Asp Leu Lys Ala Met Lys Tyr Thr Trp Gln Val Ala Gln Glu Thr Leu
        355                 360                 365

Arg Met Phe Pro Pro Val Phe Gly Thr Phe Arg Lys Ala Ile Thr Asp
    370                 375                 380
```

```
Ile Gln Tyr Asp Gly Tyr Thr Ile Pro Lys Gly Trp Lys Leu Leu Trp
385                 390                 395                 400

Thr Thr Tyr Ser Thr His Pro Lys Asp Leu Tyr Phe Asn Glu Pro Glu
            405                 410                 415

Lys Phe Met Pro Ser Arg Phe Asp Gln Glu Gly Lys His Val Ala Pro
        420                 425                 430

Tyr Thr Phe Leu Pro Phe Gly Gly Gln Arg Ser Cys Val Gly Trp
        435                 440                 445

Glu Phe Ser Lys Met Glu Ile Leu Leu Phe Val His His Phe Val Lys
        450                 455                 460

Thr Phe Ser Ser Tyr Thr Pro Val Asp Pro Asp Glu Lys Ile Ser Gly
465                 470                 475                 480

Asp Pro Leu Pro Pro Leu Pro Ser Lys Gly Phe Ser Ile Lys Leu Phe
            485                 490                 495

Pro Arg Pro
```

<210> SEQ ID NO 47
<211> LENGTH: 1497
<212> TYPE: DNA
<213> ORGANISM: Artificial Sequence
<220> FEATURE:
<223> OTHER INFORMATION: Synthetic Polynucleotide

<400> SEQUENCE: 47

```
atggatgccc tctataagtc taccgtggcg aaatttaacg aagtaaccca gctggattgc      60
agcactgagt catttagcat cgctttgagt gcaattgccg ggatcttgct gttgctcctg     120
ctgtttcgct cgaaacgtca tagtagcctg aaattacctc cgggcaaact gggcattccg     180
tttatcggtg agtcctttat ttttttgcgc gcgctgcgca gcaattctct ggaacagttc     240
tttgatgaac gtgtgaagaa gttcggcctg gtatttaaaa cgtcccttat cggtcacccg     300
acggttgtcc tgtgcgggcc cgcaggtaat cgcctcatcc tgagcaacga agaaaagctg     360
gtacagatgt cctggccggc gcagtttatg aagctgatgg agagaactc agttgcgacc     420
cgccgtggtg aagatcacat tgttatgcgc tccgcgttgg caggcttttt cggcccggga     480
gctctgcaat cctatatcgg caagatgaac acggaaatcc aaagccatat taatgaaaag     540
tggaaaggga aggacgaggt taatgtctta cccctggtgc gggaactggt ttttaacatc     600
agcgctattc tgttctttaa catttacgat aagcaggaac aagaccgtct gcacaagttg     660
ttagaaacca ttctggtagg ctcgtttgcc ttaccaattg atttaccggg tttcgggttt     720
caccgcgctt tacaaggtcg tgcaaaactc aataaaatca tgttgtcgct tattaaaaaa     780
cgtaaagagg acttacagtc gggatcggcc accgcgacgc aggacctgtt gtctgtgctt     840
ctgactttcc gtgatgataa gggcaccccg ttaaccaatg acgaaatcct ggacaacttt     900
agctcactgc ttcacgcctc ttacgacacc cgactagtc aatggctct gattttcaaa     960
ttactgtcaa gtaaccctga tgctatcag aaagtcgtgc aagagcaact cgagattctg    1020
agcaataagg aagaaggtga gaaaattacc tggaaagatc ttaaggccat gaaatacacg    1080
tggcaggttg cgcaggagac acttcgcatg tttccaccgg tgttcgggac cttccgcaaa    1140
gcgatcacgg atattcagta tgacggatac acaatcccga aaggttggaa actgttgtgg    1200
actacctata gcactcatcc taaggacctt tacttcaacg aaccggagaa atttatgcct    1260
agtcgtttcg atcaggaagg caacatgtt gcgccctata ccttcctgcc ctttggaggc    1320
ggtcagcgga gttgtgtggg ttgggagttc tctaagatgg agattctcct cttcgtgcat    1380
```

```
catttcgtga aaacattttc gagctatacc ccggtcgatc ccgatgaaaa aatttccggc   1440
gatccactgc cgccgttacc gagcaaaggg ttttcaatca aactgttccc tcgtccg     1497
```

<210> SEQ ID NO 48
<211> LENGTH: 717
<212> TYPE: PRT
<213> ORGANISM: Artificial Sequence
<220> FEATURE:
<223> OTHER INFORMATION: Synthetic Polypeptide

<400> SEQUENCE: 48

```
Met Gln Ala Asn Ser Asn Thr Val Glu Gly Ala Ser Gln Gly Lys Ser
1               5                   10                  15

Leu Leu Asp Ile Ser Arg Leu Asp His Ile Phe Ala Leu Leu Leu Asn
            20                  25                  30

Gly Lys Gly Gly Asp Leu Gly Ala Met Thr Gly Ser Ala Leu Ile Leu
        35                  40                  45

Thr Glu Asn Ser Gln Asn Leu Met Ile Leu Thr Thr Ala Leu Ala Val
    50                  55                  60

Leu Val Ala Cys Val Phe Phe Val Trp Arg Arg Gly Gly Ser Asp
65                  70                  75                  80

Thr Gln Lys Pro Ala Val Arg Pro Thr Pro Leu Val Lys Glu Glu Asp
                85                  90                  95

Glu Glu Glu Glu Asp Asp Ser Ala Lys Lys Val Thr Ile Phe Phe
            100                 105                 110

Gly Thr Gln Thr Gly Thr Ala Glu Gly Phe Ala Lys Ala Leu Ala Glu
        115                 120                 125

Glu Ala Lys Ala Arg Tyr Glu Lys Ala Val Phe Lys Val Val Asp Leu
    130                 135                 140

Asp Asn Tyr Ala Ala Asp Asp Glu Gln Tyr Glu Glu Lys Leu Lys Lys
145                 150                 155                 160

Glu Lys Leu Ala Phe Phe Met Leu Ala Thr Tyr Gly Asp Gly Glu Pro
                165                 170                 175

Thr Asp Asn Ala Ala Arg Phe Tyr Lys Trp Phe Leu Glu Gly Lys Glu
            180                 185                 190

Arg Glu Pro Trp Leu Ser Asp Leu Thr Tyr Gly Val Phe Gly Leu Gly
        195                 200                 205

Asn Arg Gln Tyr Glu His Phe Asn Lys Val Ala Lys Ala Val Asp Glu
    210                 215                 220

Val Leu Ile Glu Gln Gly Ala Lys Arg Leu Val Pro Val Gly Leu Gly
225                 230                 235                 240

Asp Asp Asp Gln Cys Ile Glu Asp Asp Phe Thr Ala Trp Arg Glu Gln
                245                 250                 255

Val Trp Pro Glu Leu Asp Gln Leu Leu Arg Asp Glu Asp Asp Glu Pro
            260                 265                 270

Thr Ser Ala Thr Pro Tyr Thr Ala Ala Ile Pro Glu Tyr Arg Val Glu
        275                 280                 285

Ile Tyr Asp Ser Val Val Ser Val Tyr Glu Glu Thr His Ala Leu Lys
    290                 295                 300

Gln Asn Gly Gln Ala Val Tyr Asp Ile His Pro Cys Arg Ser Asn
305                 310                 315                 320

Val Ala Val Arg Arg Glu Leu His Thr Pro Leu Ser Asp Arg Ser Cys
                325                 330                 335

Ile His Leu Glu Phe Asp Ile Ser Asp Thr Gly Leu Ile Tyr Glu Thr
```

```
                    340                 345                 350
Gly Asp His Val Gly Val His Thr Glu Asn Ser Ile Glu Thr Val Glu
                355                 360                 365
Glu Ala Ala Lys Leu Leu Gly Tyr Gln Leu Asp Thr Ile Phe Ser Val
            370                 375                 380
His Gly Asp Lys Glu Asp Gly Thr Pro Leu Gly Gly Ser Ser Leu Pro
385                 390                 395                 400
Pro Pro Phe Pro Gly Pro Cys Thr Leu Arg Thr Ala Leu Ala Arg Tyr
                405                 410                 415
Ala Asp Leu Leu Asn Pro Pro Arg Lys Ala Ala Phe Leu Ala Leu Ala
                420                 425                 430
Ala His Ala Ser Asp Pro Ala Glu Ala Glu Arg Leu Lys Phe Leu Ser
            435                 440                 445
Ser Pro Ala Gly Lys Asp Glu Tyr Ser Gln Trp Val Thr Ala Ser Gln
        450                 455                 460
Arg Ser Leu Leu Glu Ile Met Ala Glu Phe Pro Ser Ala Lys Pro Pro
465                 470                 475                 480
Leu Gly Val Phe Phe Ala Ala Ile Ala Pro Arg Leu Gln Pro Arg Tyr
                485                 490                 495
Tyr Ser Ile Ser Ser Ser Pro Arg Phe Ala Pro Ser Arg Ile His Val
                500                 505                 510
Thr Cys Ala Leu Val Tyr Gly Pro Ser Pro Thr Gly Arg Ile His Lys
            515                 520                 525
Gly Val Cys Ser Asn Trp Met Lys Asn Ser Leu Pro Ser Glu Glu Thr
        530                 535                 540
His Asp Cys Ser Trp Ala Pro Val Phe Val Arg Gln Ser Asn Phe Lys
545                 550                 555                 560
Leu Pro Ala Asp Ser Thr Thr Pro Ile Val Met Val Gly Pro Gly Thr
                565                 570                 575
Gly Phe Ala Pro Phe Arg Gly Phe Leu Gln Glu Arg Ala Lys Leu Gln
                580                 585                 590
Glu Ala Gly Glu Lys Leu Gly Pro Ala Val Leu Phe Phe Gly Cys Arg
            595                 600                 605
Asn Arg Gln Met Asp Tyr Ile Tyr Glu Asp Glu Leu Lys Gly Tyr Val
        610                 615                 620
Glu Lys Gly Ile Leu Thr Asn Leu Ile Val Ala Phe Ser Arg Glu Gly
625                 630                 635                 640
Ala Thr Lys Glu Tyr Val Gln His Lys Met Leu Glu Lys Ala Ser Asp
                645                 650                 655
Thr Trp Ser Leu Ile Ala Gln Gly Gly Tyr Leu Tyr Val Cys Gly Asp
            660                 665                 670
Ala Lys Gly Met Ala Arg Asp Val His Arg Thr Leu His Thr Ile Val
        675                 680                 685
Gln Glu Gln Glu Ser Val Asp Ser Ser Lys Ala Glu Phe Leu Val Lys
    690                 695                 700
Lys Leu Gln Met Asp Gly Arg Tyr Leu Arg Asp Ile Trp
705                 710                 715

<210> SEQ ID NO 49
<211> LENGTH: 2151
<212> TYPE: DNA
<213> ORGANISM: Artificial Sequence
<220> FEATURE:
<223> OTHER INFORMATION: Synthetic Polynucleotide
```

<400> SEQUENCE: 49

```
atgcaggcga attctaatac ggttgaaggc gcgagccaag gcaagtctct tctggacatt      60
agtcgcctcg accatatctt cgccctgctg ttgaacggga aaggcggaga ccttggtgcg     120
atgaccgggt cggccttaat tctgacggaa aatagccaga acttgatgat tctgaccact     180
gcgctggccg ttctggtcgc ttgcgttttt tttttcgttt ggcgccgtgg tggaagtgat     240
acacagaagc ccgccgtacg tcccacacct cttgttaaag aagaggacga agaagaagaa     300
gatgatagcg ccaagaaaaa ggtcacaata tttttggca cccagaccgg caccgccgaa      360
ggtttcgcaa aggccttagc tgaggaagca aaggcacgtt atgaaaaggc ggtatttaaa     420
gtcgtggatt tggataacta tgcagcggat gacgaacagt acgaagagaa gttgaaaaag     480
gaaaagctag cgttcttcat gctcgccacc tacggtgacg gcgaaccgac tgataatgcc     540
gctcgctttt ataaatggtt tctcgagggt aaagagcgcg agccatggtt gtcagatctg     600
acttatggcg tgtttggctt aggtaaccgt cagtatgaac actttaacaa ggtcgcgaaa     660
gcggtggacg aagtgctcat tgaacaaggc gccaaacgtc tggtaccggt agggcttggt     720
gatgatgatc agtgcattga ggacgacttc actgcctgga gagaacaagt gtggcctgag     780
ctggatcagc tcttacgtga tgaagatgac gagccgacgc tgcgaccccc gtacacggcg     840
gctattccag ataccgggt ggaaatctac gactcagtag tgtcggtcta tgaggaaacc      900
catgcgctga acaaaatgg acaagccgta tacgatatcc accaccgtg tcgcagcaac       960
gtggcagtac gtcgtgagct gcataccccg ctgtcggatc gtagttgtat tcatctggaa    1020
ttcgatatta gtgatactgg gttaatctat gagacgggcg accacgttgg agttcatacc    1080
gagaattcaa ttgaaaccgt ggaagaagca gctaaactgt taggttacca actggataca    1140
atcttcagcg tgcatgggga caaggaagat ggaacaccat tgggcgggag tagcctgcca    1200
ccgccgtttc cggggccctg cacgctgcgg acggcgctgg cacgttacgc ggacctgctg    1260
aaccctccgc gcaaagccgc cttcctggca ctggccgcac acgcgtcaga tccggctgaa    1320
gctgaacgcc ttaaatttct cagttctcca gccggaaaag acgaatactc acagtgggtc    1380
actgcgtccc aacgcagcct cctcgagatt atggccgaat tccccagcgc gaaaccgccg    1440
ctgggagtgt ttttcgccgc aatagcgccg cgcttgcaac ctaggtatta tagcatctcc    1500
tcctccccgc gtttcgcgcc gtctcgtatc catgtaacgt gcgcgctggt ctatggtcct    1560
agccctacgg ggcgtattca taaaggtgtg tgcagcaact ggatgaagaa ttcttttgccc   1620
tccgaagaaa cccacgattg cagctgggca ccggtctttg tgcgccagtc aaactttaaa    1680
ctgcccgccg attcgacgac gccaatcgtg atggttggac ctggaaccgg cttcgctcca    1740
tttcgcgggct tccttcagga acgcgcaaaa ctgcaggaag cgggcgaaaa attgggcccg    1800
gcagtgctgt tttttgggtg ccgcaaccgc cagatggatt acatctatga agatgagctt    1860
aagggttacg ttgaaaaagg tattctgacg aatctgatcg ttgcattttc acgaaaggc     1920
gccaccaaag agtatgttca gcacaagatg ttagagaaag cctccgacac gtggtcttta    1980
atcgcccagg gtggttatct gtatgtttgc ggtgatgcga agggtatggc cagagacgta    2040
catcgcaccc tgcatacaat cgttcaggaa caagaatccg tagactcgtc aaaagcggag    2100
tttttagtca aaagctgca atggatgga cgctacttac gggatatttg g              2151
```

<210> SEQ ID NO 50
<211> LENGTH: 5
<212> TYPE: PRT
<213> ORGANISM: Artificial Sequence

```
<220> FEATURE:
<223> OTHER INFORMATION: Synthetic Polypeptide

<400> SEQUENCE: 50

Gly Ser Thr Gly Ser
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 51

Met Ala Leu Leu Leu Ala Val Phe
1               5

<210> SEQ ID NO 52
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 52
cgtaccatgg ttgatttcaa tgaatatatg aaaagtaagg c                    41
```